US011577056B2

(12) United States Patent
Rentschler et al.

(10) Patent No.: US 11,577,056 B2
(45) Date of Patent: Feb. 14, 2023

(54) MEDICAL DEVICES INCLUDING TEXTURED INFLATABLE BALLOONS

(71) Applicants: The Regents of the University of Colorado, Denver, CO (US); Aspero Medical, Inc., Boulder, CO (US)

(72) Inventors: Mark E. Rentschler, Boulder, CO (US); Randall N. Allard, Golden, CO (US)

(73) Assignees: ASPERO MEDICAL, INC., Boulder, CO (US); THE REGENTS OF THE UNIVERSITY OF COLORADO, Denver, CO (US)

(*) Notice: Subject to any disclaimer, the term of this patent is extended or adjusted under 35 U.S.C. 154(b) by 142 days.

(21) Appl. No.: 16/805,303

(22) Filed: Feb. 28, 2020

(65) Prior Publication Data

US 2020/0215310 A1     Jul. 9, 2020

Related U.S. Application Data

(63) Continuation-in-part of application No. 16/249,550, filed on Jan. 16, 2019, now Pat. No. 11,089,944.
(Continued)

(51) Int. Cl.
 *A61M 25/10* (2013.01)
 *A61B 1/00* (2006.01)

(52) U.S. Cl.
CPC ..... *A61M 25/1002* (2013.01); *A61B 1/00082* (2013.01); *A61M 25/1011* (2013.01);
(Continued)

(58) Field of Classification Search
CPC ................. A61M 25/1002; A61M 2025/1086
See application file for complete search history.

(56) References Cited

U.S. PATENT DOCUMENTS

| 4,364,392 A | 12/1982 | Strother et al. |
| 5,320,634 A * | 6/1994 | Vigil ............... A61B 17/320725 |
| | | 604/103.08 |

(Continued)

FOREIGN PATENT DOCUMENTS

| JP | 3799612 B2 | 7/2006 |
| JP | 2012-81130 A | 4/2012 |

(Continued)

OTHER PUBLICATIONS

Extended European Search Report, EP16871700.7, dated Jul. 5, 2019.
(Continued)

*Primary Examiner* — Katherine M Shi
*Assistant Examiner* — Mohammed S Adam
(74) *Attorney, Agent, or Firm* — Polsinelli PC

(57) ABSTRACT

Medical devices including balloons and balloons are provided that include an elongate body and an inflatable balloon defining a longitudinal axis, the inflatable balloon being attached to and partially surrounding at least a section of the elongate body. The medical device further includes a plurality of protrusions extending from the inflatable balloon. When the inflatable balloon is in an unstrained state, each of the plurality of protrusions extends in a first transverse direction relative to the longitudinal axis. In certain implementations, the inflatable balloon may also be configured to collapse such that, when in a collapsed state, an untextured portion of the inflatable balloon extends to a radius and the plurality of protrusions does not extend beyond the radius.

21 Claims, 40 Drawing Sheets

Related U.S. Application Data

(60) Provisional application No. 62/617,868, filed on Jan. 16, 2018.

(52) U.S. Cl.
CPC ... *A61M 25/1029* (2013.01); *A61M 2025/109* (2013.01); *A61M 2025/1015* (2013.01); *A61M 2025/1086* (2013.01)

(56) References Cited

U.S. PATENT DOCUMENTS

| | | | |
|---|---|---|---|
| 5,423,745 | A | 6/1995 | Todd |
| 5,749,889 | A | 5/1998 | Bacich et al. |
| 6,120,516 | A | 9/2000 | Selmon et al. |
| 6,258,099 | B1 | 7/2001 | Mareiro |
| 6,478,807 | B1 | 11/2002 | Foreman et al. |
| 6,562,049 | B1 | 5/2003 | Norlander et al. |
| 6,676,667 | B2 | 1/2004 | Mareiro et al. |
| 6,835,189 | B2 | 12/2004 | Musbach et al. |
| 6,841,213 | B2 | 1/2005 | Parsonage et al. |
| 7,306,616 | B2 | 12/2007 | Eidenschink et al. |
| 7,354,419 | B2 | 4/2008 | Davies, Jr. et al. |
| 7,459,192 | B2 | 12/2008 | Parsonage et al. |
| 7,776,078 | B2 | 8/2010 | Burgmeier et al. |
| 7,927,362 | B2 | 4/2011 | Shippy, III et al. |
| 7,963,942 | B2 | 6/2011 | Chen |
| 7,985,063 | B2 | 7/2011 | Schewe et al. |
| 8,048,028 | B2 | 11/2011 | Horn et al. |
| 8,048,093 | B2 | 11/2011 | Mapes et al. |
| 8,096,942 | B2 | 1/2012 | Yoshida et al. |
| 8,202,245 | B2 | 6/2012 | Weber et al. |
| 8,216,267 | B2 | 7/2012 | Pallazza |
| 8,353,868 | B2 | 1/2013 | Davies, Jr. et al. |
| 8,550,985 | B2 | 10/2013 | Weber et al. |
| 8,597,239 | B2 | 12/2013 | Gerrans et al. |
| 8,690,824 | B2 | 4/2014 | Holman et al. |
| 8,771,332 | B2 | 7/2014 | Johnson et al. |
| 8,852,146 | B2 | 10/2014 | Horn et al. |
| 8,876,763 | B2 | 11/2014 | Noddin |
| 8,945,047 | B2 | 2/2015 | McAuley et al. |
| 8,945,168 | B2 | 2/2015 | Davies, Jr. et al. |
| 9,067,045 | B2 | 6/2015 | Burton et al. |
| 9,295,808 | B2 | 3/2016 | De Kock et al. |
| 9,339,169 | B2 | 5/2016 | Rentschler et al. |
| 9,409,001 | B2 | 8/2016 | Aggerholm et al. |
| 9,415,193 | B2 | 8/2016 | Campbell et al. |
| 9,492,297 | B2 | 11/2016 | Pallazza |
| 9,521,945 | B2 | 12/2016 | Farhadi |
| 9,592,119 | B2 | 3/2017 | Tilson et al. |
| 9,717,615 | B2 | 8/2017 | Grandt |
| 9,730,726 | B2 | 8/2017 | Bacino et al. |
| 9,867,529 | B2 | 1/2018 | Farhadi |
| 9,901,715 | B2 | 2/2018 | Cully et al. |
| 9,993,626 | B2 | 6/2018 | Lysgaard |
| 10,166,374 | B2 | 1/2019 | Giasolli et al. |
| 10,173,038 | B2 | 1/2019 | Campbell et al. |
| 10,201,683 | B2 | 2/2019 | Schneider et al. |
| 10,335,581 | B2 | 7/2019 | Schneider et al. |
| 10,376,679 | B2 | 8/2019 | Cox et al. |
| 10,456,564 | B2 | 10/2019 | Terliuc et al. |
| 10,617,853 | B2 | 4/2020 | Campbell et al. |
| 2003/0028097 | A1 | 2/2003 | D'Amico et al. |
| 2004/0044351 | A1 | 3/2004 | Searle |
| 2004/0092870 | A1 | 5/2004 | Squire |
| 2004/0167496 | A1 | 8/2004 | Poole et al. |
| 2004/0254422 | A1 | 12/2004 | Singh |
| 2005/0119678 | A1* | 6/2005 | O'Brien ......... A61B 17/320758 606/159 |
| 2005/0137615 | A1 | 6/2005 | Mapes et al. |
| 2006/0235457 | A1 | 10/2006 | Belson |
| 2006/0287574 | A1 | 12/2006 | Chin |
| 2007/0106216 | A1 | 5/2007 | Noddin |
| 2007/0112250 | A1 | 5/2007 | Kura |
| 2008/0228139 | A1 | 9/2008 | Melsheimer |
| 2008/0269559 | A1 | 10/2008 | Miyamoto et al. |
| 2010/0022832 | A1 | 1/2010 | Makiyama |
| 2010/0030204 | A1* | 2/2010 | Stein ................ A61B 18/02 606/21 |
| 2010/0240955 | A1 | 9/2010 | Sinai et al. |
| 2010/0318094 | A1 | 12/2010 | Oishi et al. |
| 2011/0105840 | A1 | 5/2011 | Terliuc et al. |
| 2012/0259217 | A1 | 10/2012 | Gerrans et al. |
| 2012/0289772 | A1 | 11/2012 | O'Connell et al. |
| 2014/0276407 | A1 | 9/2014 | Devries et al. |
| 2015/0057657 | A1 | 2/2015 | Squire et al. |
| 2015/0088246 | A1 | 3/2015 | Astarci et al. |
| 2015/0105621 | A1 | 4/2015 | Farhadi |
| 2016/0058982 | A1 | 3/2016 | Aggerholm et al. |
| 2017/0035277 | A1 | 2/2017 | Kucharski et al. |
| 2017/0065155 | A1 | 3/2017 | Farhadi |
| 2017/0333075 | A1 | 11/2017 | Bacino et al. |
| 2017/0333686 | A1 | 11/2017 | Schneider et al. |
| 2018/0140804 | A1 | 5/2018 | Tsukamoto et al. |
| 2018/0256863 | A1 | 9/2018 | Lysgaard |
| 2018/0280666 | A1 | 10/2018 | Yamazaki |
| 2018/0304052 | A1 | 10/2018 | Schneider et al. |
| 2018/0368665 | A1 | 12/2018 | Rentschler et al. |
| 2019/0216297 | A1 | 7/2019 | Rentschler et al. |
| 2020/0276417 | A1 | 9/2020 | Rentschler et al. |
| 2021/0307589 | A1 | 6/2021 | Rentschler et al. |

FOREIGN PATENT DOCUMENTS

| | | |
|---|---|---|
| WO | WO 2008/127224 A1 | 10/2008 |
| WO | WO 2010/011843 A1 | 1/2010 |
| WO | WO 2014/190026 A1 | 11/2014 |
| WO | WO 2015/065163 A1 | 5/2015 |
| WO | WO 2016/158294 A1 | 10/2016 |
| WO | WO 2018/143254 A1 | 8/2018 |

OTHER PUBLICATIONS

International Search Report and Written Opinion, PCT/US2016/064915, dated Apr. 13, 2017.
International Search Report and Written Opinion, PCT/US2019/013832, dated Apr. 10, 2019.
Non-Final Office Action, U.S. Appl. No. 16/249,550, dated Jun. 26, 2020.
Extended European Search Report, EP19741681.1, dated Sep. 7, 2021.
Final Office Action, U.S. Appl. No. 16/249,550, dated Dec. 22, 2020.
International Search Report and Written Opinion, PCT/US2020/033258, dated Aug. 19, 2020.
Non-Final Office Action, U.S. Appl. No. 15/780,493, dated Sep. 1, 2020.
Notice of Reasons for Rejection, JP2020-5601 19 dated Sep. 6, 2021.
Notice of Allowance, U.S. Appl. No. 16/249,550, dated Apr. 21, 2021.
International Search Report and Written Opinion, PCT/US2022/024893, dated Jul. 5, 2022.

* cited by examiner

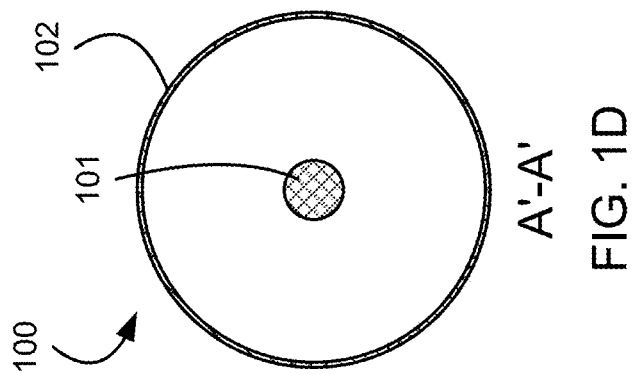
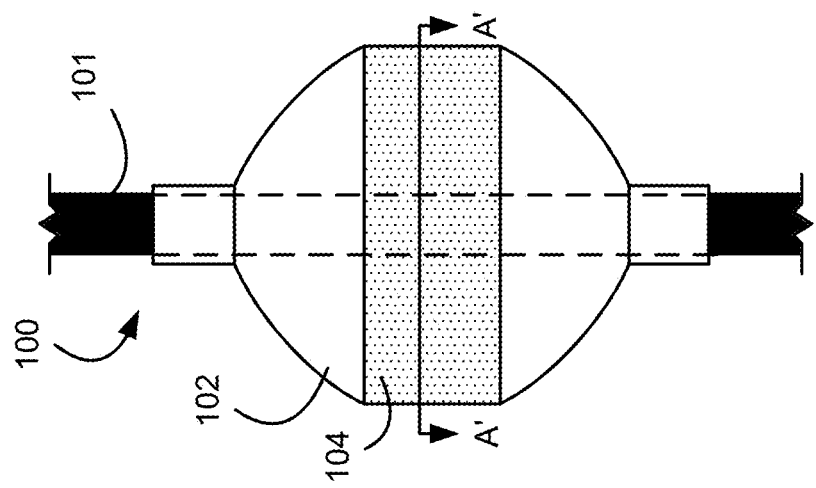
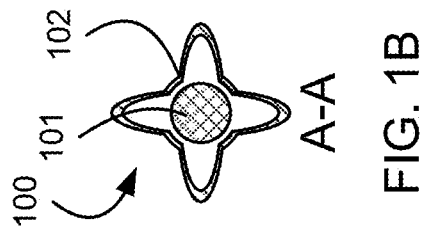
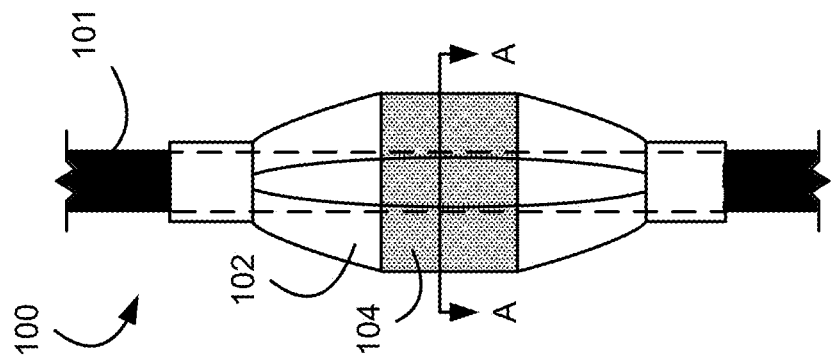

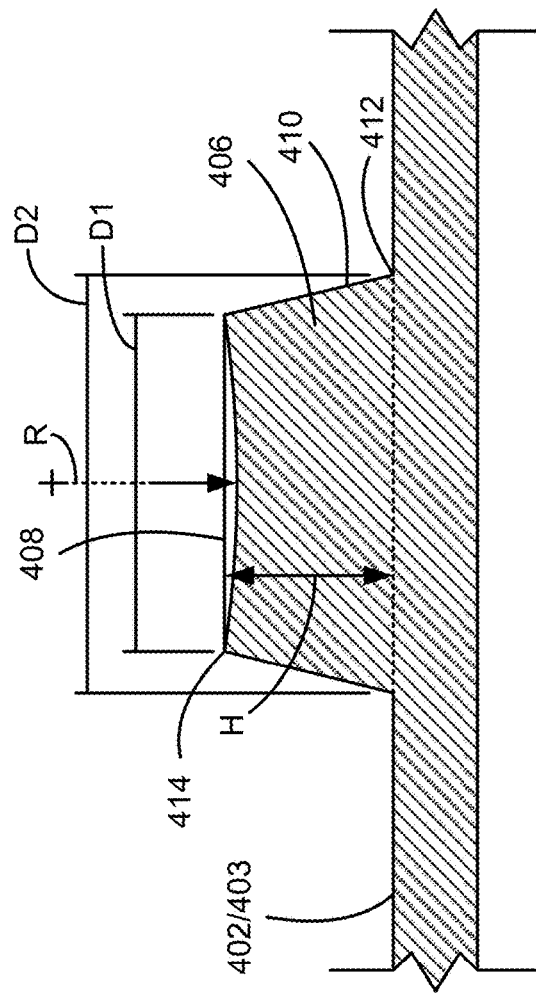
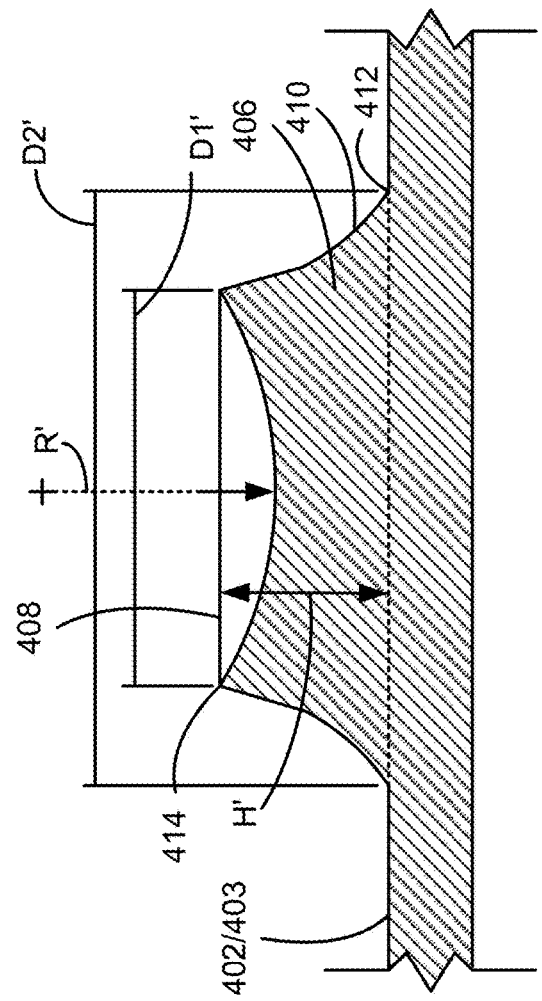
FIG. 6A
FIG. 6B

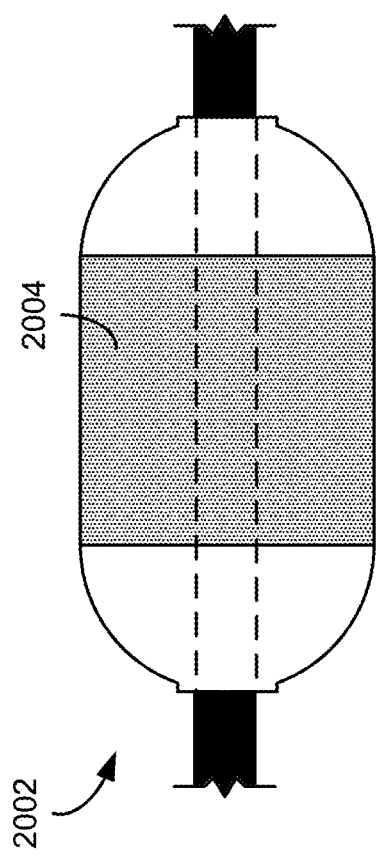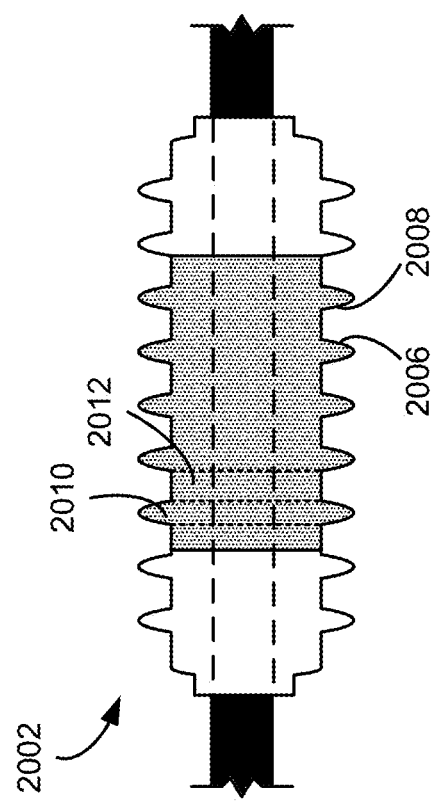
FIG. 20A
FIG. 20B

MEDICAL DEVICES INCLUDING TEXTURED INFLATABLE BALLOONS

CROSS-REFERENCE TO RELATED APPLICATION

This non-provisional utility application is a continuation-in-part of U.S. patent application Ser. No. 16/249,550, filed Jan. 16, 2019, and titled "MEDICAL DEVICES INCLUDING TEXTURED INFLATABLE BALLOONS," which claims priority under 35 U.S.C. § 119(e) from U.S. patent application Ser. No. 62/617,868, filed Jan. 16, 2018. The entire contents of each of the foregoing applications are incorporated herein by reference for all purposes.

STATEMENT REGARDING FEDERALLY SPONSORED RESEARCH DEVELOPMENT

This invention was made with government support under grant number 1636203 and 1827787 awarded by the National Science Foundation. The government has certain rights in the invention.

TECHNICAL FIELD

Aspects of the present disclosure are directed to balloons for use in medical procedures and, in particular, to balloons configured to selectively engage with a physiological lumen such that medical devices including the balloons may be selectively and variably engaged with the lumen.

BACKGROUND

Endoscopy is a procedure wherein a highly trained physician pushes a long flexible endoscope through a physiological lumen of a patient, such as, but not limited to the colon or small bowel. Conventional endoscopes often struggle to complete procedures that involve irregular anatomy or small bowel examination. These factors can lead to missed diagnoses of early state conditions, such as colorectal cancer, which is the third most deadly cancer in America, but which has a 93% survival rate when detected in its initial stages.

To complete many of these examinations, double balloon enteroscopy (DBE) is often used. The double balloon system comprises two balloons, one attached the front of the scope and one attached to a scope overtube. These balloons serve as anchoring points for the endoscope and provide extra support for the long flexible scope to be directed. When these anchoring balloons are inflated and deflated in succession, they aid in the advancement of the scope. When inflated, the balloons push against the wall of the colon, small bowel, or other physiological lumen, and grip the wall forming an anchor point, reducing movement while the scope pushes against the anchor point. DBE has been shown to be a very successful procedure for irregular anatomy patients and small bowel endoscopy.

Balloons commonly used in the art for DBE procedures are conventionally made of smooth latex-like materials. These materials have a low coefficient of friction, especially with the soft, mucous covered wall of the small bowel, colon, and other portions of the gastrointestinal (GI) tract. The low coefficient of friction can cause the balloon to slip prematurely, thus not allowing the scope to properly advance. Over-inflation of the balloons can increase friction with the wall of the small bowel or colon, but at the same time can also cause damage to the patient's GI tract.

There is thus a need in the art for novel devices that can be used to perform gastroenterology and other medical procedures. Such devices should increase the amount of successful completions of such procedures, and provide a more comfortable experience for the patient. By allowing for more colonoscopies to be completed fully, more cases of colorectal cancer would be found in early enough stages for successful treatment.

With these thoughts in mind among others, aspects of the devices and methods disclosed herein were conceived.

SUMMARY

In one aspect of the present disclosure, a medical device configured to be inserted into a physiological lumen of a patient is provided. The medical device includes an elongate body and an inflatable balloon defining a longitudinal axis, the inflatable balloon being attached to and partially surrounding at least a section of the elongate body. The medical device further includes a plurality of protrusions extending from the inflatable balloon. When the inflatable balloon is in an unstrained state, each of the plurality of protrusions extends in a first transverse direction relative to the longitudinal axis.

In certain implementations, the inflatable balloon is formed from at least one of low-density polyethylene, latex, polyether block amide, silicone, poly-siloxane, polyethylene terephthalate, nylon, and polyurethane.

In other implementations, each protrusion of the plurality of protrusions has a height from and including about 50 μm to and including about 5000 μm tall.

In certain implementations, each protrusion of the plurality of protrusions has a frustroconical shape. In other implementations, each protrusion of the plurality of protrusions has a pyramidal shape, which may be a flat-topped pyramid shape.

In still other implementations, each of the plurality of protrusions comprises a flat top surface, a side surface, and an edge formed between the flat top surface and the side surface, the edge having a radius from and including 5 μm to and including 500 μm.

In other implementations, the plurality of protrusions is a first plurality of protrusions and the medical device comprises a second plurality of protrusions extending from the inflatable balloon in a second transverse direction when the balloon is in an unstrained state, the second transverse direction being different than the first transverse direction.

In still other implementations, each protrusion of the plurality of protrusions includes a concave tip.

In other implementations, the inflatable balloon includes an untextured proximal end and an untextured distal end and the plurality of protrusions are disposed between the untextured proximal end and the untextured distal end.

In certain implementations, when in a collapsed state, an untextured portion of the inflatable balloon extends to a radius and the plurality of protrusions does not extend beyond the radius.

In still other implementations, the plurality of protrusions is arranged in at least one longitudinal row. In such implementations, each protrusion of the plurality of protrusions has a width and adjacent protrusions in the at least one longitudinal row have a separation from and including 5% of the width to and including 50% of the width.

In another aspect of the present disclosure, another medical device configured to be inserted into a physiological lumen of a patient is provided. The medical device includes an elongate bod and an inflatable balloon defining a longitudinal axis, the inflatable balloon being attached to and partially surrounding at least a section of the elongate body. The inflatable balloon further includes a first textured surface portion including a first plurality of protrusions, a second textured surface portion including a second plurality of protrusions, and an untextured surface portion extending between the first textured surface portion and the second textured surface portion.

In some implementations, when the inflatable balloon is in an unstrained state, each protrusion of the first plurality of protrusions extends in a first transverse direction relative to the longitudinal axis and each protrusion of the second plurality of protrusions extends in a second transverse direction relative to the longitudinal axis that is different than the first transverse direction.

In other implementations, the inflatable balloon includes an untextured proximal end and an untextured distal end. Each of the first textured surface portion, the second textured surface portion, and the untextured surface portion are disposed between the untextured proximal end and the untextured distal end. In such implementations and when in a collapsed state, each of the untextured proximal end and the untextured distal end may extend to a radius and each of the first textured surface portion and the second textured surface may not extend beyond the maximum radius.

In still other implementations, when in a collapsed state, each of the first textured surface portion and the second textured surface portion are concave. In such implementations, each of the first textured surface portion and the second textured surface portion may be concave about an axis perpendicular to a longitudinal axis of the balloon.

In another aspect of the present disclosure a balloon for use with a medical device is provided. The balloon includes an annular distal end, an annular proximal end, and a body defining a longitudinal axis and disposed between the annular distal end and the annular proximal end. The body includes one or more textured portions, each of the one or more textured portions further comprising a respective plurality of protrusions, wherein, when the inflatable balloon is in an unstrained state, each plurality of protrusions extends in a respective transverse direction relative to the longitudinal axis.

In certain implementations, the one or more textured portions includes a plurality of textured portions and the body further includes an untextured portions extending circumferentially between the plurality of textured portions, and, when the balloon is in a collapsed state, the untextured portions extend to a radius and the textured portions do not extend beyond the radius. In such implementations, when the balloon is in the collapsed state, the untextured portions may be concave.

BRIEF DESCRIPTION OF THE DRAWINGS

Example implementations of the present disclosure are illustrated in referenced figures of the drawings. It is intended that the implementations and corresponding figures disclosed herein are to be considered illustrative rather than limiting.

FIG. 1A is a side elevation view of a first medical device according to the present disclosure including a balloon in a deflated state.

FIG. 1B is a cross-sectional view of the medical device of FIG. 1A.

FIG. 1C is a side elevation view of the medical device of FIG. 1A in which the balloon is in an at least partially inflated state.

FIG. 1D is a cross-sectional view of the medical device of FIG. 1C.

FIGS. 6A-6B are more detailed illustrations of the cross-sectional views of FIGS. 4B and 5B.

FIGS. 20A-20B are schematic illustrations of another example balloon in accordance with the present disclosure in each of an at least partially inflated state and a collapsed state, respectively.

DETAILED DESCRIPTION

Figure 1E:
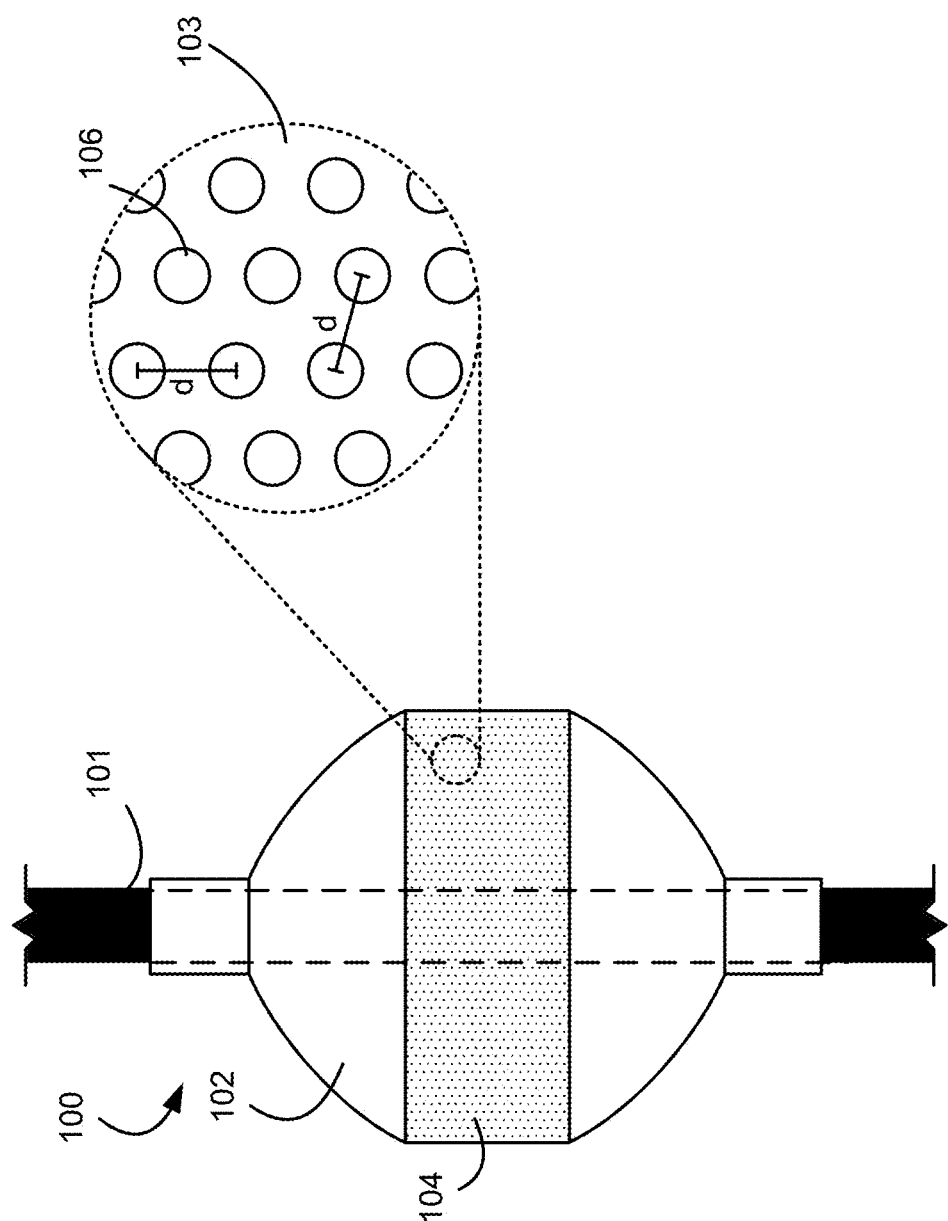
FIG. 1E is a side elevation view of the medical device of FIG. 1A in the at least partially inflated state and further including a detail view illustrating protrusions disposed on the balloon.

The current disclosure relates in part to balloon designs that can be incorporated into medical devices, such as endoscopes. In particular, the current disclosure relates to balloons having exterior surfaces that are at least partially textured. Texturing of the balloons is achieved by the inclusion of multiple pillar-like protrusions extending from the surface of the balloon. In at least one application of the current disclosure, a medical device including the balloon is disposed within a physiological lumen with the balloon in a substantially deflated state. The physiological lumen may be a portion of a patient's GI tract, but more generally may be any vessel, airway, duct, tract, stricture, sphincter, biliary stricture, or similar physiological structure. Once positioned within the physiological lumen, the balloon may be inflated such that the protrusions contact the lumen wall, thereby engaging the balloon and medical device with the lumen wall. The balloon may be subsequently deflated to facilitate disengagement of the protrusions from the wall of the lumen, thereby permitting movement of the medical device. Accordingly, the balloons (or similar structures) disclosed herein include textured/patterned surfaces that provide increased friction and adhesion with biological tissue as compared to conventional smooth balloons. As a result of such increased friction and adhesion, balloons in accordance with the present disclosure more reliably engage biological tissue as compared to conventional balloon designs.

As described below in further detail, the shape and distribution of the protrusions may vary in applications of the present disclosure to provide varying degrees of traction between the balloon and the biological tissue with which the balloon is in traction. In certain implementations, the protrusions may also be configured to deform in response to a strain applied to the balloon. Such deformation alters the adhesive and frictional properties of the protrusions. As a result, a physician may control the relative traction of the balloon to the biological tissue by selectively inflating or deflating the balloon. For example, a physician may apply a first strain to the balloon (e.g., by inflating the balloon to a first extent) resulting in a first degree of deformation of the protrusions and a corresponding first engagement level of the balloon (e.g., a first level of engagement based on the adhesive and frictional properties of the protrusions when in a first shape). Subsequently, the physician may apply a second strain (e.g., by modifying the degree to which the balloon is inflated) resulting in a second degree of deformation of the protrusions and a corresponding second engagement level of the balloon.

Although discussed herein primarily in the context of endoscopic balloons for use in the GI tract, the present disclosure may be used in a variety of medical and non-medical applications. Accordingly, to the extent that any particular applications of the present disclosure are discussed herein, such applications should not be viewed as limiting the scope of the present disclosure. Nevertheless example implementations of the present disclosure are discussed below to provide additional details regarding aspects of the present disclosure.

FIGS. 1A-1E are various views of an example medical device 100 including an inflatable balloon 102 in accordance with the present disclosure. More specifically, FIG. 1A is a side elevation view of the medical device 100 with the balloon 102 in deflated or collapsed state, FIG. 1B is a cross-sectional view along cross-section A-A of the balloon 102 of FIG. 1A, FIG. 1C is a side elevation view of the medical device 100 in an at least partially inflated state, FIG. 1D is a cross-sectional view along cross-section A'-A' of the balloon 102 of FIG. 1C, and FIG. 1E is a side elevation view of the medical device 100 including an inlay illustrating a textured portion 104 of the balloon 102.

For purposes of the present disclosure, balloons disclosed herein are described as being in various states corresponding to various stages of inflation and deflation. An "unstrained state", for example, refers to a state in which in which the corresponding balloon may be partially inflated but not yet subject to strain and, as a result, generally corresponds to the "as-molded" shape of the balloon. A "strained state" generally refers to a state in which a balloon is inflated beyond the extent necessary to achieve the unstrained state. A "collapsed state", in contrast, generally refers to a state of the balloon in which at least a portion of the balloon constricts or is otherwise reduced as compared to the unstrained state. In certain implementations, balloons in accordance with the present disclosure may be biased into a collapsed state. Alternatively, balloons in accordance with the present disclosure may transition into the collapsed state in response to air (or other gas) being removed from the balloon or in response to the balloon being otherwise deflated from the unstrained state. Balloons herein may also be described as being "at least partially inflated", which generally refers to a state of the balloon including the unstrained state and any degree of inflation beyond the unstrained state. Similarly, the "collapsed" state may generally refer to balloons that are in any degree of collapse up to but excluding the unstrained state.

During use, the medical device 100 may be inserted into and located within a physiological lumen of a patient. Such insertion may generally be performed while the balloon 102 is in the deflated state illustrated in FIG. 1A. Once properly located, air or a similar fluid medium may be provided to the balloon 102 to inflate the balloon, as shown in FIG. 1B. When such inflation is performed with the balloon 102 within the physical lumen, at least a part of the textured portion 104 may be made to abut an inner wall of the physiological lumen, thereby causing frictional and adhesive engagement between the textured portion 104 and the physiological lumen and mucosal lining.

Various arrangements for the balloon 102 on the medical device 100 are feasible. In the specific example of FIGS. 1A-1E, the balloon 102 has a cylindrical body capped by hemispherical ends. In another non-limiting example, the balloon 102 is disposed around an endoscope 101 or similar tubular body of the medical device 100 such that the balloon 102 forms a toroidal or spherical shape having a central lumen. In another non-limiting example, the balloon 102 is disposed around the endoscope 101 forming a cylindrical shape having hemispherical rounded ends, wherein the endoscope 101 runs along the major axis of the cylinder. In other implementations, the balloon 102 may be ellipsoid in shape or "pill" shaped. Regardless of the foregoing, balloons in accordance with the present disclosure may be substantially any shape as desired.

The balloon 102 may be made of at least one non-rigid material. For example, in one example implementation the balloon material may include one or more of low-density polyethylene (LDPE), latex, polyether block amide (e.g., PEBAX®), silicone, polyethylene terephthalate (PET/PETE), nylon, polyurethane, and any other thermoplastic elastomer, siloxane, or other similar non-rigid materials. In certain implementations, the balloon 102 may be formed from one material; however, in other implementations the balloon 102 may be formed from multiple materials. For example, the balloon 102 may include a body formed from a first material but may also include reinforcing or structural members formed from a second material.

Material selection for the balloon 102 may also be based, in part, on material hardness. Although material hardness may vary based on application, in at least one specific implementation, the balloon 102 may be formed from a material having a predetermined hardness of Shore 30A such as, but not limited to, Dow Corning Class VI Elastomer C6-530, which is a liquid silicone rubber elastomer.

In general, the balloon 102 has a first diameter or shape when in a collapsed or unstrained state and a second diameter when inflated into an unstrained state, the second diameter being larger than the first diameter. In certain implementations, the balloon 102 may be further inflatable beyond the unstrained state into a strained state. For example, in at least one implementation the balloon 102 can be strained up to about 1,000% relative to its uninflated state, although other maximum strain levels are possible. In other implementations, the balloon 102 does not have a set lower inflation limit. The balloon 102 may also be configured to be inflated to a first turgid state having a defined shape and then be further inflated up to a maximum strain while retaining the defined shape.

The balloon 102 may be structured such that, when deflated or due to biasing, the balloon 102 collapses into a particular shape. For example, as illustrated in FIGS. 1A and 1B, the balloon 102 may be configured to collapse into a star or similar shape. Such controlled collapse of the balloon 102 may achieved in various ways including, without limitation, selectively reinforcing portions of the balloon 102 with additional material and including semi-rigid structural elements coupled to or embedded within the balloon 102. In other implementations, the balloon 102 may form a pill, ovoid, or similar elongated shape when deflated, including a shape that substantially corresponds to the inflated shape of the balloon 102.

As illustrated FIG. 1C, the balloon 102 includes at least one textured portion 104. In general and as illustrated in the inlay of FIG. 1C, the textured portion 104 includes multiple protrusions, such as protrusion 106, extending from a surface 103 of the balloon 102. The protrusions 106 of the textured portion 104 may have any pattern. For example and without limitation, the textured portion 104 may include evenly spaced protrusions arranged in a regular geometric pattern, such as a grid. The balloon 102 illustrated in FIG. 1C, for example, includes protrusions arranged in a triangular grid pattern. In other implementations, other grid patterns may be used including, without limitation, square, rectangular, hexagonal, and octagonal grid patterns or any other suitable grid pattern based on a tessellation of geometric shapes. In certain implementations, the textured portion 104 may include multiple areas of protrusions, with each area having a different protrusion density or protrusion pattern. In still other implementations, the protrusions may be arranged in a random or semi-random pattern across the textured portion 104. More generally, textured portions in accordance with implementations of the present disclosure may include any suitable arrangement of protrusions.

In certain implementations, the protrusions 106 may be evenly spaced such that the center-to-center dimension between adjacent protrusions is constant in a given state of the balloon 102 (e.g., the unstrained state). For example, in one implementation the center-to-center spacing between protrusions (as indicated in the inlay of FIG. 1E by dimension "d") may be about 20 µm to about 1,000 µm in the unstrained state. In other implementations, the protrusions may be evenly spaced with a center-to-center spacing from and including about 50 µm to and including about 750 µm apart from one another. In yet another implementation, the protrusions may be evenly spaced with a center-to-center spacing from and including about 100 µm to and including about 600 µm apart from one another. In still other implementations, the center-to-center spacing between protrusions may be greater than 1000 µm.

The inset of FIG. 1E illustrates the protrusions 106 arranged in longitudinally extending rows with adjacent rows being offset but equally spaced. It should be appreciated, however, that in other implementations of the present disclosure, aspects of the arrangement of the protrusions 106 may vary. For example, in certain implementations, protrusions of adjacent longitudinal rows may be aligned with each other. Similarly, all rows may be spaced uniformly (e.g., all rows may be spaced 1000 µm apart). Alternatively, spacing between all rows may vary or may only be uniform for a subset of adjacent rows. As yet another example, rows of the protrusions may extend along varying lengths of the textured portion 104. Moreover, in at least certain implementations, the protrusions 106 may not be arranged in longitudinal rows. Rather, the protrusions may be arranged in any suitable pattern including, without limitation, circumferential rows, biased rows (e.g., rows extending both longitudinally and circumferentially), or in a random or pseudo-random pattern.

The protrusions 106 may be formed in various ways. For example and without limitation, the protrusions may be integrally formed with the balloon 102 (e.g., by simultaneously molding the balloon 102 and the protrusions), may be separately formed from and subsequently attached to the balloon 102 (e.g., by first extruding the balloon and then adhering the protrusions to the balloon 102), or may be formed directly onto the balloon 102 (e.g., by a co- or over-molding process in which the balloon 102 is first molded and then the protrusions are molded onto the balloon 102).

As previously discussed, balloons according to the present disclosure may be configured to inflate or deflate in a particular manner. For example, as illustrated in FIG. 1A, the balloon 102 is configured to collapse into a star- or clover-shape when deflated. More specifically, the balloon 102 is configured such that certain longitudinal sections of the balloon 102 are collapsed to a greater degree than others when air is removed from the balloon 102. Such selective collapse may be achieved, for example, by increasing the thickness of the balloon 102 in the longitudinal portions that are to remain protruding when the balloon 102 is deflated.

A similar design is illustrated in FIGS. 20A-20B. More specifically, FIG. 20A illustrates a balloon 2002 in an at least partially inflated state while FIG. 20B illustrates the balloon 2002 in a collapsed state. Similar to the balloon 102 of FIGS. 1A-1B, the balloon 2002 is configured to selectively collapse when deflated. More specifically, and as illustrated in FIG. 20B, the balloon 2002 is generally divided into alternating axial bands configured to have different diameters when collapsed. For example, a first band 2010 is configured to collapse to a lesser degree than a second band 2012. As previously noted, such selective collapse may be achieved by increasing the thickness of the first band 2010 or by otherwise reinforcing the first band 2010. In other implementations, the shape of at least some of the bands when in the deflated state may be dictated by a mandrel or similar body disposed within the balloon 2002 and about which the balloon 2002 collapses when deflated.

Varying the degree to which the balloon collapses, as illustrated in the examples of FIGS. 1A-1B and 20A-20B, facilitates insertion and transportation of the balloon when in the deflated state. In particular, by reducing the proportion of protrusions that are outwardly/radially facing or otherwise disposed at a maximum diameter, the overall adhesion and friction provided by the balloon is reduced. As a result, the likelihood and amount of contact between the balloon and a wall of a physiological lumen is significantly reduced. Referring to FIGS. 20A-20B, for example, the balloon 2002 includes a textured portion 2004 having protrusions according to the present disclosure. When in the at least partially inflated state (as shown in FIG. 20A), each of the protrusions is directed substantially outwardly/radially and, as a result, is able to readily contact and engage the wall of the physiological lumen. However, when in the collapsed state (as shown in FIG. 20B), sections of the textured portion 2004 of the balloon 2002 (such as faces 2006 and 2008) and their respective protrusions are directed at least partially in a longitudinal direction and, as a result, are less likely to directly engage the wall of the physiological lumen. Similarly, sections of the textured portion 2004 (such as the second band 2012) may be recessed when the balloon 2002 is in the deflated state relative to other sections of the textured portion 2004 (such as the first band 2010). As a result the recessed sections are less likely to contact and engage the wall of the physiological lumen.

Figure 21A:
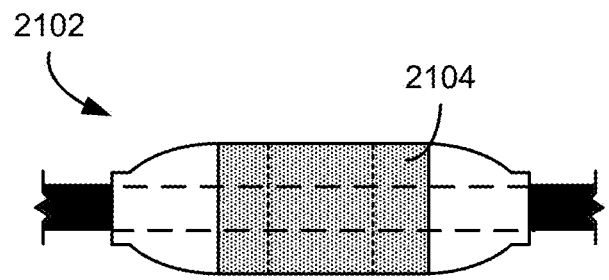
FIGS. 21A-21C are schematic illustrations of yet another example balloon in accordance with the present disclosure in each of a collapsed state, a partially inflated state, and an inflated state, respectively.
Figure 21B:
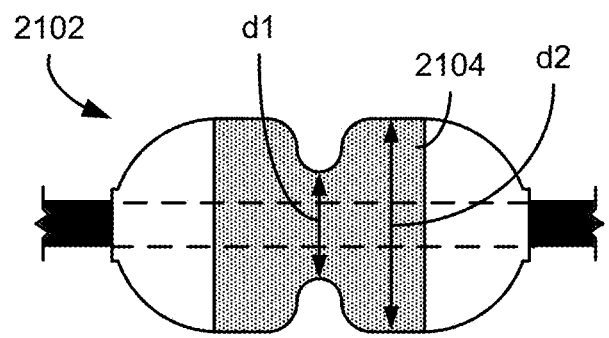
Figure 21C:
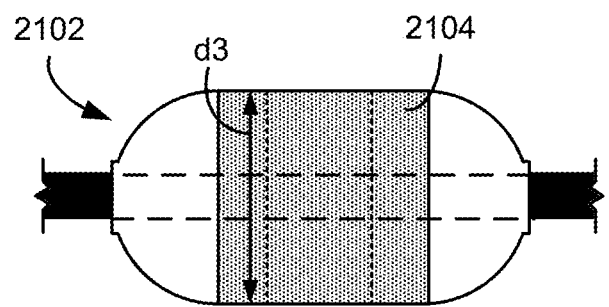

FIGS. 21A-21C illustrates another example balloon 2102 exhibiting non-uniform inflation/deflation. FIG. 21A illustrates the balloon 2102 in a collapsed or unstrained state and in which the balloon 2102 assumes a pill-shaped configuration. As shown in FIG. 21B, the balloon 2102 may be inflated to a first inflation level in which the balloon 2102 assumes an hourglass (or similar shape) in which at least a portion of the balloon 2102 expands to a diameter (d1) that is less than a diameter (d2) of other portions of the balloon 2102. At a second inflation level, the balloon 2102 may expand such that the diameter of the balloon is substantially uniform (d3).

In certain implementations, the controlled inflation of the balloon 2102 may be used to vary the adhesive and frictional force between the balloon 2102 and a wall of a physiological lumen within which the balloon 2102 is disposed. For example, the balloon 2102 includes a textured portion 2104 having protrusions according to the present disclosure. When in the partially inflated state (as illustrated in FIG. 21B), the diameter of the textured portion 2104 varies such that only a limited proportion of the protrusions are each of disposed at the maximum diameter of the balloon 2102 and oriented in an outward/radial direction. As a result, the adhesion and friction between the balloon 2102 and wall of the physiological lumen is reduced as compared to when the balloon 2102 is further inflated (as illustrated in FIG. 21C) such that substantially all of the textured portion 2104 is at the same diameter. Accordingly, a user of the balloon 2102 may inflate the balloon 2102 to the first inflation level to achieve a first degree of engagement and to the second inflation level to achieve a second, greater degree of engagement.

Figure 22A:
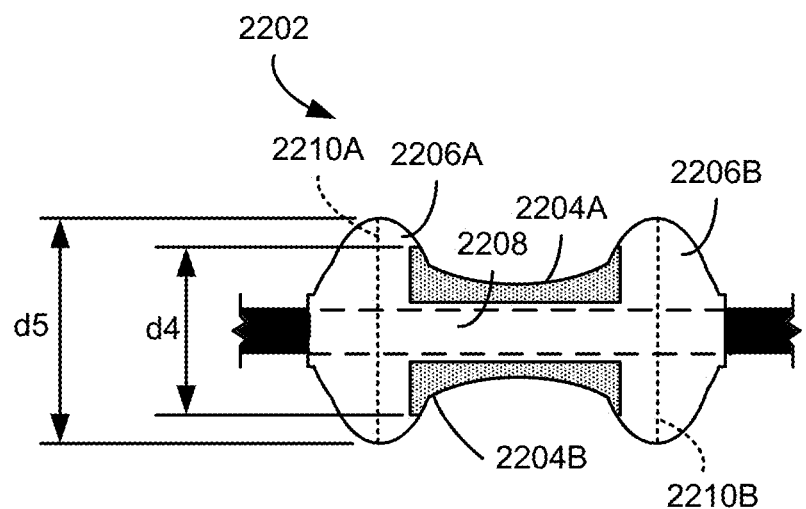
FIGS. 22A and 22B are schematic illustrations of another example balloon in accordance with the present disclosure in each of a collapsed state and an at least partially inflated state, respectively, illustrating controlled collapse of the balloon.
Figure 22B:
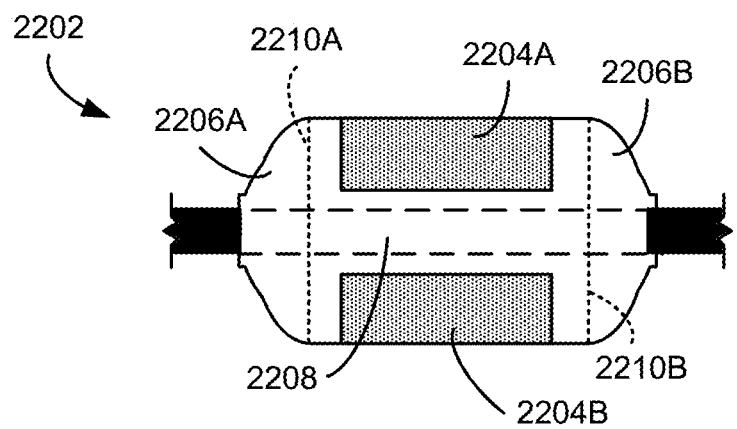

FIGS. 22A and 22B illustrate another example balloon 2202. FIG. 22A illustrates the balloon 2202 in a collapsed state while FIG. 22B illustrates the balloon 2202 in an at least partially inflated state. As shown, the balloon 2202 generally includes textured portions 2204A, 2204B disposed between two untextured ends 2206A, 2206B. The balloon 2202 also includes an untextured portion 2208 disposed between the textured portions 2204A, 2204B.

The textured portions 2204A, 2204B and the untextured ends 2206A, 2206B are structured such that, when in the collapsed state illustrated in FIG. 22A, the textured portions 2204A, 2204B have a maximum diameter (d4) that is less than a maximum diameter (d5) of the untextured ends 2206A, 2206B. In such an arrangement, the outermost surface of the balloon 2202 is provided by the untextured ends 2206A, 2206B while the textured portions 2204A, 2204B are disposed radially inward of the outermost surface. In other words, when in the collapsed state, the textured portions 2204A, 2204B may become concave. As a result, when in the collapsed state illustrated in FIG. 22A, contact between the balloon 2202 and an inner surface of a physiological lumen within which the balloon 2202 may be disposed is primarily between the inner surface of the physiological lumen and the untextured ends 2206A, 2206B.

As the balloon 2202 is inflated, the diameter of the textured portions 2204A, 2204B may expand to at least equal that of the untextured ends 2206A, 2206B, as illustrated in FIG. 22B. As a result, the textured portions 2204A, 2204B may come into contact with the inner surface of the physiological lumen, thereby increasing friction between the balloon 2202 and the inner surface of the physiological lumen.

In light of the arrangement illustrated in FIGS. 22A and 22B, the balloon 2202 may be inserted into and moved along the physiological lumen in the deflated/low-friction state illustrated in FIG. 22A. When the balloon 2202 is at an intended location, the balloon 2202 may then be inflated to expose the textured portions 2204A, 2204B and to cause the textured portions 2204A, 2204B to come into contact with the inner surface of the physiological lumen. Doing so increases friction between the balloon 2202 and the inner surface of the physiological lumen and may be used to anchor or otherwise reduce movement of the balloon 2202 within the physiological lumen.

As illustrated in FIGS. 22A and 22B, in at least some implementations of the present disclosure, an untextured portion 2208 may be disposed between textured portions of the balloon 2202. For example, one or more untextured portions 2208 may extend longitudinally between textured portions of the balloon 2202, such as the textured portions 2204A, 2204B. When in the collapsed state illustrated in FIG. 22A, the untextured portion 2208 may have a diameter similar to that of the untextured ends 2206A, 2206B, thereby providing another low-friction surface that contacts the inner surface of the physiological lumen during insertion and transportation. In such cases, when in the deflated configuration, the textured portions 2204A, 2204B may generally be concave about an axis extending perpendicular to a longitudinal axis of the balloon 2202. Alternatively, the untextured portion 2208 may deflate similar to the textured portions 2204A, 2204B. In such implementations, the untextured portion 2208 may similarly become concave when deflated, giving the balloon 2202 an "hourglass" or similar shape that tapers radially inward from the untextured ends 2206A, 2206B when in the deflated state.

Figure 23A:
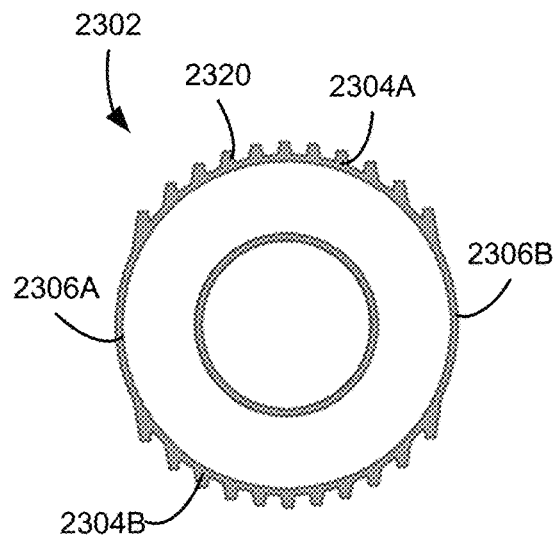
FIGS. 23A-23C are schematic illustrations of still another example balloon in accordance with the present disclosure in each of an unstrained state, a collapsed state, and an inflated/strained state, respectively, illustrating an alternative approach to controlled collapse of the balloon.
Figure 23B:
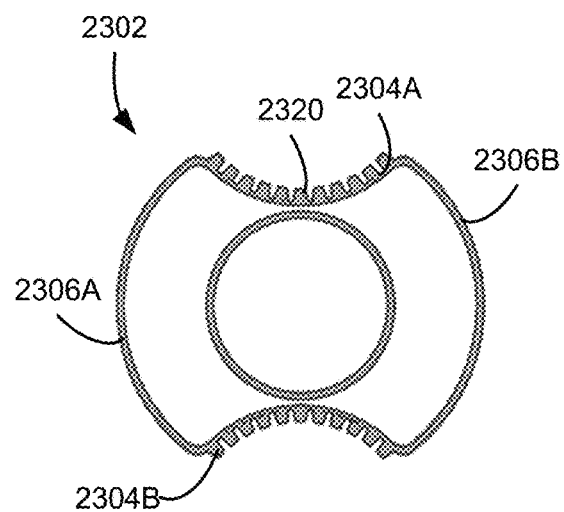
Figure 23C:
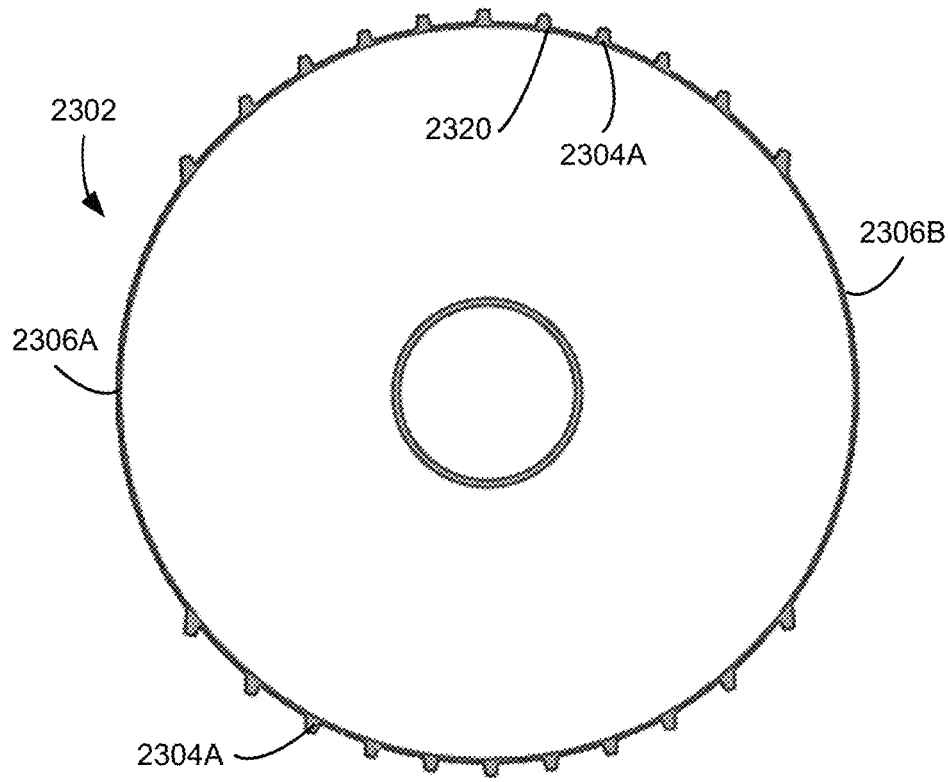

FIGS. 23A-23C are cross-sectional views of a third balloon 2302 including features to selectively collapse portions of the balloon 2302 when in the deflated state. More specifically, FIG. 23A illustrates the balloon 2302 in an unstrained state, FIG. 23B illustrates the balloon 2302 in a collapsed state, and FIG. 23C illustrates the balloon 2300 in a strained inflated state in which the balloon is inflated to a greater extent than as illustrated in FIG. 23A. As shown, the balloon 2302 generally includes textured portions 2304A, 2304B and untextured portions 2306A, 2306B extending circumferentially between the textured portions 2304A, 2304B. In at least certain implementations, the balloon 2302 may also include untextured proximal and distal ends, as included in other implementations of the present disclosure. As illustrated in each of FIGS. 23A-23C, each of the textured portions 2304A, 2304B generally includes a plurality of protrusions, such as protrusions 2320.

In contrast to textured portions 2204A, 2204B of the balloon 2202 of FIGS. 22A and 22B, in which the textured portions 2204A, 2204B becomes concave about an axis perpendicular to a longitudinal axis of the balloon 2202, the balloon 2302 is configured such that the textured portions 2304A, 2304B become concave about an axis parallel to the longitudinal axis of the balloon 2302. As illustrated in FIG. 23B, when in the collapsed state, the concavity of the textured portions is such that the protrusions 2320 are disposed within a maximum radius defined by the untextured portions 2306A, 2306B. As a result, when in the deflated state, the balloon 2302 may be inserted into and/or transported through a physiological lumen with reduced interaction between the textured portions 2304A, 2304B and an inner surface of the physiological lumen. When in an intended position, the balloon 2302 may then be inflated such that the textured portions 2304A, 2304B expand from the concave configuration, thereby causing contact between the protrusions 2320 the inner surface of the physiological lumen. Doing so increases frictional engagement between the balloon 2302 and the inner surface, up to and including frictional engagement sufficient to anchor the balloon 2302 in place within the physiological lumen.

Controlled collapsing/concavity of balloons in accordance with the present disclosure may be achieved in various ways. For example and without limitation, portions of the balloon intended to collapse or become concave (e.g., the textured portions 2204A, 2204B) may have a smaller wall thickness than other portions intended to substantially retain their shape (e.g., the untextured portions 2206A, 2206B). In other implementations, portions of the balloon intended to retain their shape may be selectively reinforced. For example, the balloon 2200 illustrated in each of FIGS. 22A and 22B includes internal ridges 2210A, 2210B disposed within the untextured portions 2206A, 2206B. During inflation and deflation, the internal ridges reinforce the untextured portions 2206A, 2206B such that the untextured portions 2206A, 2206B maintain a more consistent shape as compared to unreinforced portions of the balloon 2200, such as the textured portion 2204A, 2204B.

Figure 24:
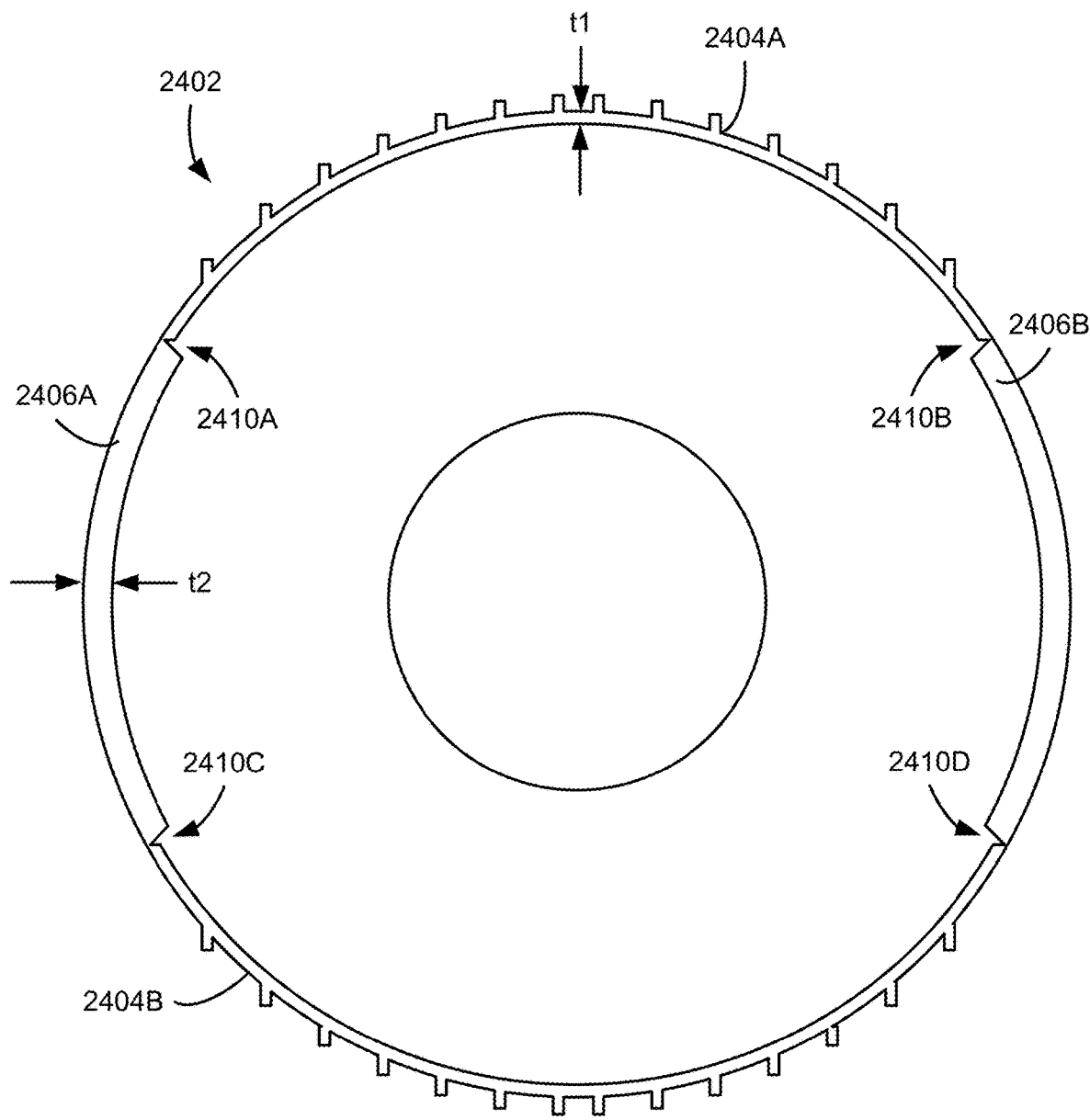
FIG. 24 is a cross-sectional view of an example balloon having varying wall thickness to facilitate controlled collapse of the balloon.

FIG. 24 illustrates an alternative structure for controlling collapse of an example balloon 2402 during deflation. The balloon 2402 includes a pair of textured portions 2404A, 2404B between which are disposed untextured portions 2406A, 2406B. As illustrated, each of the textured portions 2404A, 2404B has a first wall thickness (t1) and each of the untextured portions 2406A, 2406B has a second wall thickness (t2) that is greater than the wall thickness of the textured portions 2404A, 2404B. In one example implementation, the first wall thickness may be from and including about 100 μm to and including about 2000 μm while the second wall thickness may be from and including about 150 μm to and including about 3000 μm.

As a result, as the balloon 2402 collapses, the textured portions 2404A, 2404B will collapse and become concave prior to and to a greater extent than the untextured portions 2406A, 2406B. In certain implementations, the wall thickness of the untextured portions 2406A, 2406B may also be sufficient to prevent or substantially reduce collapse of the untextured portions 2406A, 2406B during deflation. As further illustrated in FIG. 24, controlled collapse of the balloon may also be facilitated by the use of notches 2410A-2410D or similar features that provide localized reduction of the wall thickness of the balloon 2402. For example, the notches 2410A-2410D of the balloon 2402 are formed at the transition between the textured portions 2404A, 2404B and the untextured portions 2406A, 2406B to facilitate collapse of the untextured portions 2404A, 2404B.

The specific ways in which balloons may be inflated/collapsed described above are provided merely as examples. More generally, balloons in accordance with the present disclosure may be configured to collapse and/or inflate in a non-uniform way. By doing so, different states of deflation/inflation may be used to disposed different proportions of the balloon protrusions at a maximum diameter of the balloon and/or to position different proportions of the protrusions in a substantially outwardly/radially extending direction.

Figure 2A:
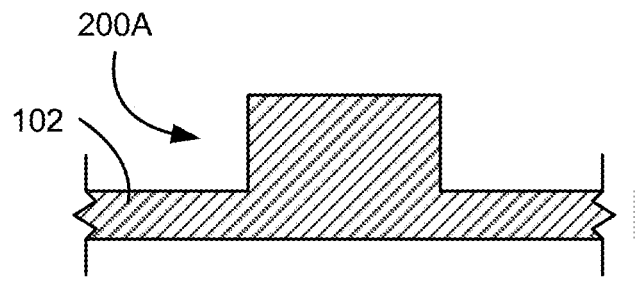
FIGS. 2A-2AD are various views of example protrusions according to the present disclosure.

FIGS. 2A-2AD are various views of example protrusions in accordance with the present disclosure. These example protrusions are shown with the corresponding balloon in an unstrained state. Accordingly, inflation of the corresponding balloons into a strained state will generally alter the shapes of the example protrusions.

Figure 2B:
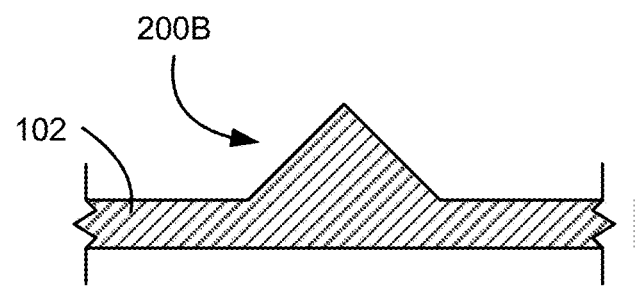
Figure 2C:
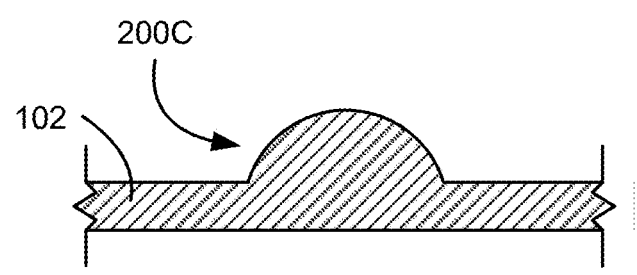
Figure 2D:
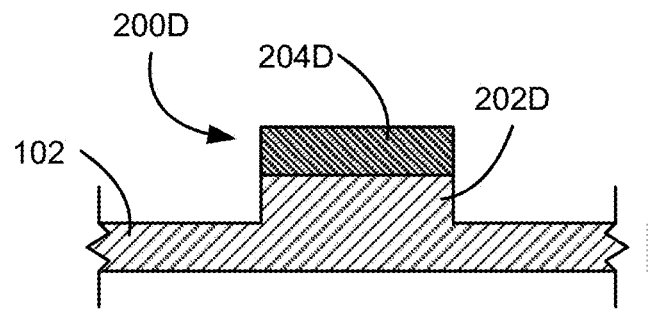

FIG. 2A illustrates a first protrusion 200A extending from the balloon 102 and having a cylindrical or rectangular shape, FIG. 2B illustrates a second protrusion 200B having a triangular or pyramidal shape, and FIG. 2C illustrates a third protrusion 200C having a rounded or hemispherical shape. FIG. 2D is a cross-sectional view of a fourth micropillar 200D composed of multiple materials.

The protrusion shapes illustrated in FIGS. 2A-2D are intended merely as examples and other protrusion shapes are possible. For example and without limitation, other implementations of the current disclosure may include protrusions having any shape, including but not limited to rectangular, square, triangular, pentagonal, heptagonal, hexagonal, pyramidal, mushroom, or spherical shape. These protrusions are solid in one example, while in other embodiments the protrusions may be hollow. The ends of the protrusions distal to the surface of the balloon 102 may also be formed in various shapes. For example and without limitation, the distal ends of the protrusions may be flat, rounded (including either of convex or concave), pointed, or mushroomed. The width/diameter of the protrusions may also vary. For example, the distal end of the protrusions may be larger in diameter than the proximal end, so as to resemble a mushroom. In other implementations, the proximal end of the protrusions may be larger in diameter than the distal end, such that the protrusions distally taper.

As noted above, FIG. 2D illustrates a protrusion 200D formed from multiple materials. More specifically, the protrusion 200D includes a first portion 202D proximal the balloon 102 and a second portion 204D distal the balloon 102. As illustrated, the first portion 202D is integrally formed with the balloon 102. The second portion 204D, on the other hand, forms a cap or tip of the protrusion 200D that may be coupled to or formed onto the first portion 202D after formation of the first portion 202D. In other implementations, each of the first and second portions 202D, 204D may be formed from different materials than the balloon 102.

The specific arrangement illustrated in FIG. 2D is intended merely as an example of a multi-material protrusion and other arrangements are possible. For example and without limitation, multi-material protrusions may be formed by embedding or implanting structural elements of a first within protrusions formed of a second material or at least partially encompassing protrusions formed from a first material with a cap, sheath, or similar element formed from a second material. It should also be appreciated that while FIG. 2D illustrates a two-material protrusion 200D, any suitable number of materials may be used to form protrusions in accordance with the present disclosure.

Figure 2E:
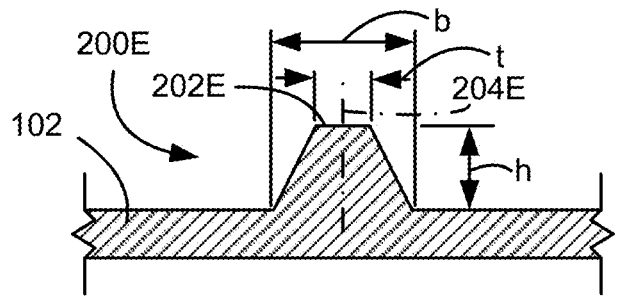
Figure 2F:
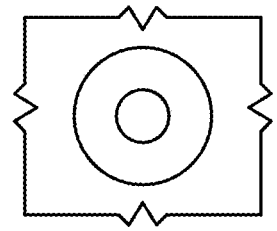

FIGS. 2E-2AD illustrate additional example protrusions that may be implemented in embodiments of the present disclosure. FIGS. 2E and 2F, for example, are a cross-sectional view and a plan view, respectively, of a protrusion 200E extending from the balloon 102 and having a frustroconical shape. As illustrated in FIG. 2E, the shape of the protrusion 200E may be defined by a base diameter b, a height h, and a top diameter t of the protrusion 200E. Although any suitable dimension for b and h may be used, in at least certain implementations, b may be from and including about 50 μm to and including about 3000 μm, h may be from and including about 25 μm to and including about 3000 μm, and t may be from and including about 25 μm to and including about 2500 μm. Moreover, while the protrusion 200E of FIGS. 2E and 2F is illustrated as having a top 202E extending substantially perpendicular to an axis 204E of the protrusion 200E, in other implementations, the top 202E may instead be biased relative to the axis 204E. The performance characteristics of the protrusion 200E may be modified by altering various aspects of the protrusion 200E. For example and without limitation, any of the base diameter, top diameter, or height of the protrusion 200E may be varied to modify the stiffness of the protrusion 200E.

Figure 2G:
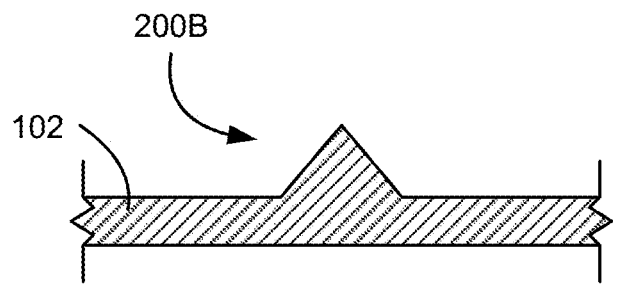
Figure 2H:
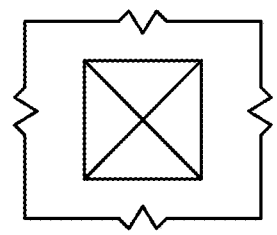
Figure 2I:
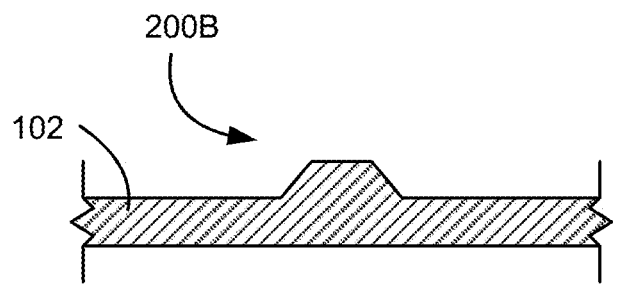
Figure 2J:
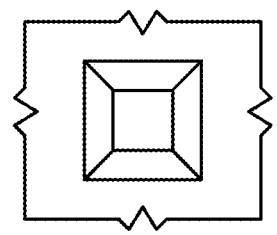
Figure 2K:
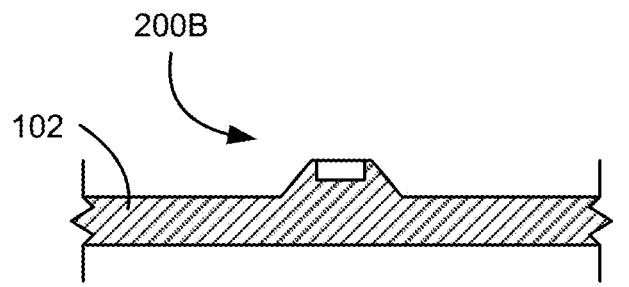
Figure 2L:
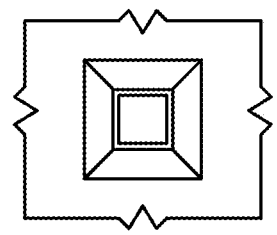
Figure 2M:
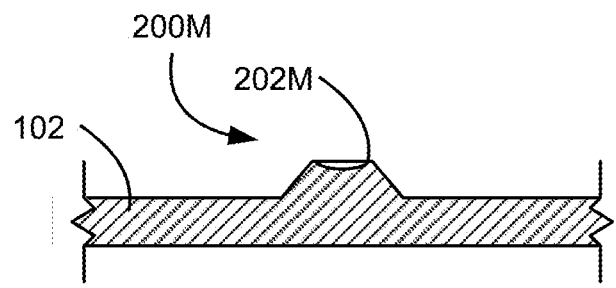
Figure 2N:
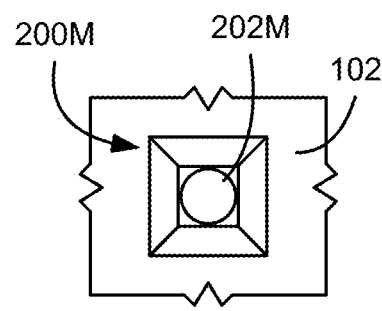

FIGS. 2G-2N illustrate various implementations of pyramidal protrusions. Specifically, FIGS. 2G and 2H are a cross-sectional view and a plan view, respectively, of a protrusion 200G extending from the balloon 102 and having a pointed, square-based pyramid shape. FIGS. 2I and 2J are a cross-sectional view and a plan view, respectively, of a protrusion 200J extending from the balloon 102 and having a truncated, square-based pyramid shape. FIGS. 2K and 2L are a cross-sectional view and a plan view, respectively, of a protrusion 200K extending from the balloon 102 and having a truncated, square-based pyramid shape including a square recess 202K extending into the protrusion 200K from a top surface 204K of the protrusion 200K. Similarly, FIGS. 2M and 2N are a cross-sectional view and a plan view, respectively, of a protrusion 200M extending from the balloon 102 and having a truncated, square-based pyramid shape including a concave top surface 202M.

Figure 2O:
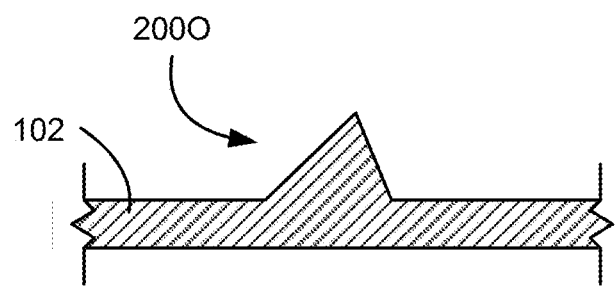
Figure 2P:
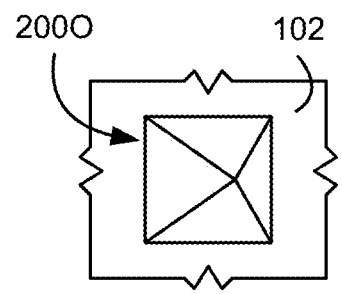
Figure 2Q:
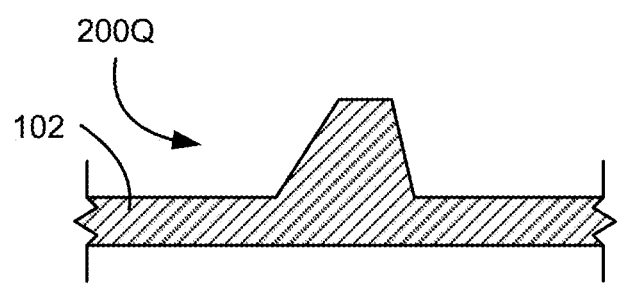
Figure 2R:
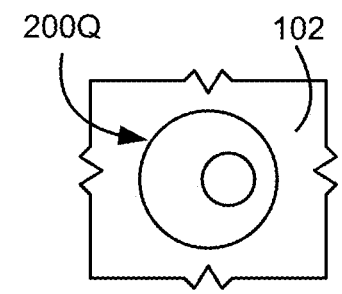

FIGS. 2O-2R illustrated example protrusions having an asymmetrical or "swept" configuration. More specifically, FIGS. 2O and 2P are a cross-sectional view and a plan view of another example protrusion 200O, the protrusion Q having a swept square-based pyramidal shape. Similarly, FIGS. 2Q and 2R are a cross-sectional view and a plan view of yet another example protrusion 200Q, the protrusion 200Q having a swept truncated conical shape. In certain implementations, such swept shapes may be the result of molding process limitations. For example, a mold for producing balloons in accordance with the present disclosure may be formed using electrical discharge machining (EDM). In such cases, a machining electrode is plunged into a mold half to form the protrusions. In applications in which the plunging path is linear and the mold half is curved, the resulting feature will inherently have a shadowed or swept shape. Nevertheless, in other implementations the swept shapes may be specifically controlled to provide improved traction, to otherwise bias the protrusions in a particular direction, to provide reinforcement in a specific direction, and the like.

Figure 2S:
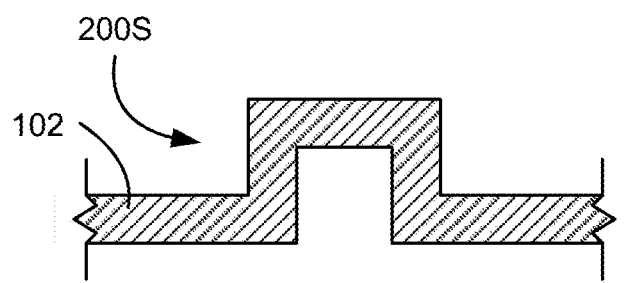

FIG. 2S is a cross-sectional view of still another example protrusion 200S. The protrusion 200S is provided to illustrate that protrusions in accordance with the present disclosure may be hollow. While illustrated in FIG. 2S as being substantially rectangular or cylindrical in shape, it should be understood that any protrusion design discussed herein may be at least partially hollow and such hollow protrusions are not limited to any specific shape or dimensions.

Figure 2T:
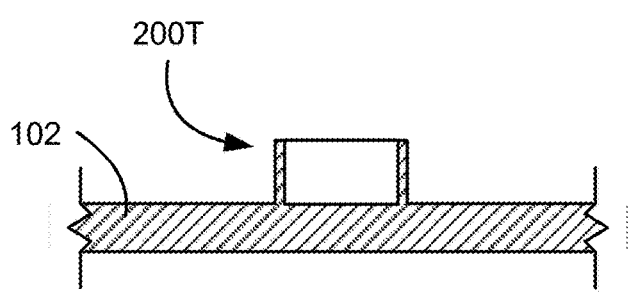
Figure 2U:
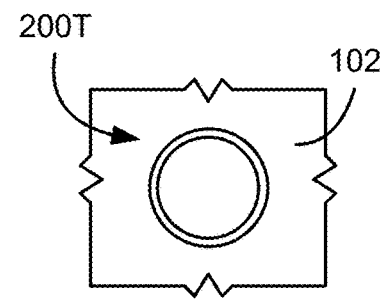

FIGS. 2T and 2U are a cross-sectional view and a plan view of another example protrusion 200T. More specifically, the protrusion 200T has a tubular cylindrical shape and is intended to illustrate an implementation of a protrusion having a tubular or thin-walled construction. Although illustrated as having a cylindrical shape, it should be understood that thin-walled/tubular protrusions similar to that illustrated in FIGS. 2T and 2U are not limited to cylindrical shapes. Rather, thin-walled or tubular protrusions may have any suitable shape.

Figure 2V:
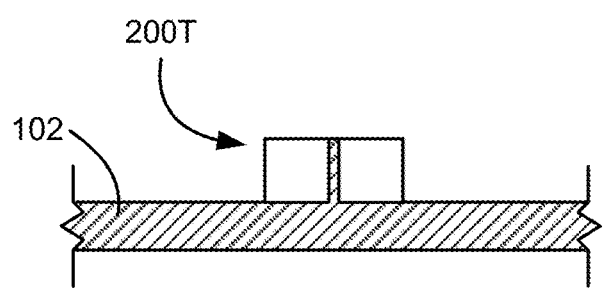
Figure 2W:
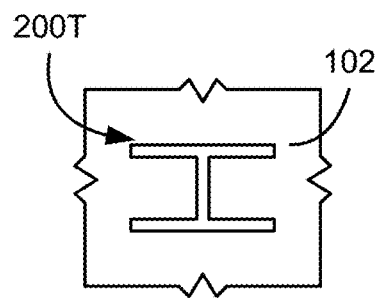

FIGS. 2V and 2W are a cross-sectional view and a plan view of still another example protrusion 200V. More specifically, the protrusion 200V has a barbell-type shape and is intended to illustrate an implementation of a protrusion formed from a series of interconnected ribs, walls, or similar structures extending from the surface of the balloon 102.

Figure 2X:
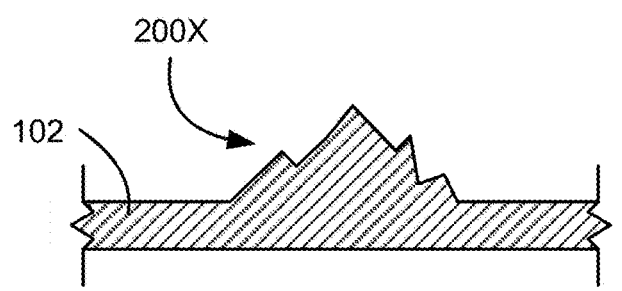

FIG. 2X is a cross-sectional view of a protrusion 200X having a jagged shape. Protrusion 200X is intended to illustrate that protrusions in accordance with the present disclosure are not limited to conventional shapes or surfaces. Rather, protrusions may be implemented having any suitable shape or surface, including random or pseudo-randomly generated shapes or surfaces.

Figure 2Y:
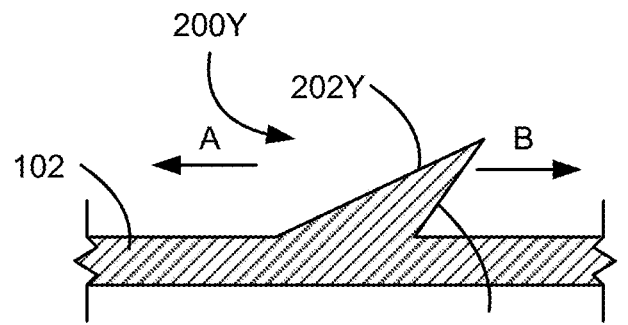

FIGS. 2Y-2AD illustrate various protrusions having a directional design. For purposes of the present disclosure, directional protrusions refer to protrusions that are specifically shaped to provide reduced friction/adhesion or improved aero- or hydrodynamic behavior in a first direction and increased friction/adhesion or reduced aero- or hydrodynamic behavior in a second direction that is generally opposite the first direction. Among other things, such protrusions designs may be beneficial for facilitating translation or movement of a balloon within a lumen in a first direction while providing increased resistance to translation or movement of the balloon in a second opposite direction.

Figure 2Z:
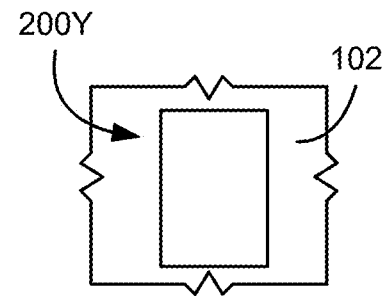
Figure 2A:
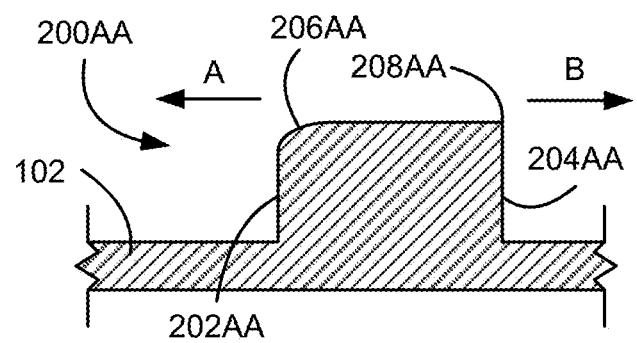
Figure 2A:
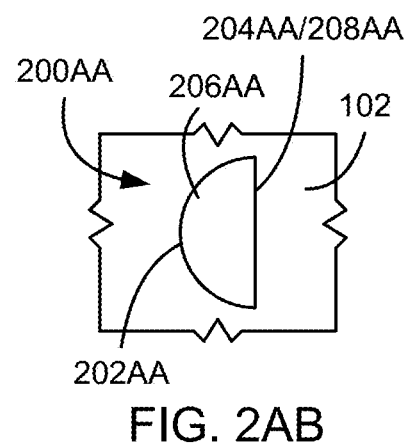
Figure 2A:
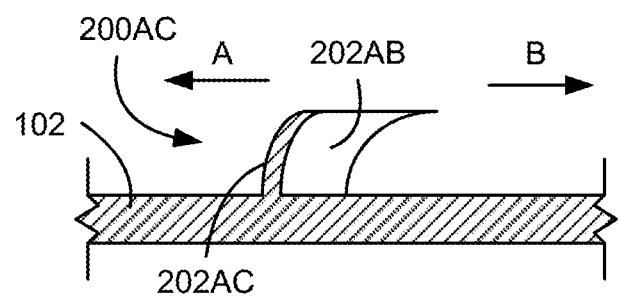
Figure 2A:
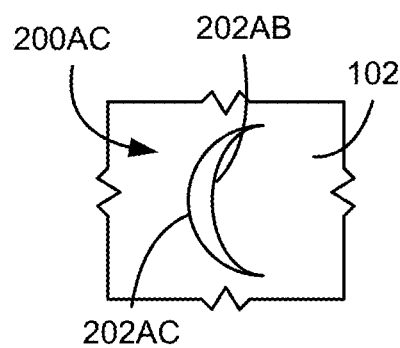

Referring first to FIGS. 2Y and 2Z, a cross-sectional and a plan view of a first directional protrusion 200Y is provided. The protrusion 200Y has a swept or sawtooth shape that provides variable resistance in opposite directions. More specifically, the shallower slope of a leading face 202Y of the protrusion provides reduced friction in a first direction a first direction (indicated by arrow A) as compared to a second, opposite direction (indicated by arrow B). In the specific implementation illustrated in FIG. 2Y, a trailing face of the protrusion 200Y is arranged such that the protrusion 200Y forms a barb or hook-like shape. However, it should be appreciated that variable directional performance may be achieved with a less aggressive design, such as the "swept" protrusions illustrated in FIGS. 2O-2R.

FIGS. 2AA and 2AB are a cross-sectional view and a plan view of a second direction protrusion 200AA having a semi-circular shape. More specifically, the protrusion 200AA includes a curved leading surface 202AA and a substantially flat tailing surface 204AA such that the protrusion 200AA provides reduced friction in a first direction (indicated by arrow A) as compared to a second direction (indicated by arrow B). Additional directional properties of the protrusion 200AA are provided by including a rounded or smoothed leading edge 206AA and a substantially sharper tailing edge 208AA. For example, in at least certain implementations, the tailing edge 208AA may have a radius from and including about 5 µm to and including about 500 µm, for example 75 µm, while the leading edge 206AA may have a radius having that is 1.1-2.0 times or greater than the radius of the tailing edge 208AA.

FIGS. 2AC and 2AD are a cross-sectional view and a plan view of a third direction protrusion 200AA having a scalloped crescent shape. More specifically, the protrusion 200AC includes a convex leading surface 202AC and a concave tailing surface 204AC such that the protrusion 200AC provides reduced friction in a first direction (indicated by arrow A) as compared to a second direction (indicated by arrow B). Similar to the protrusion 200Y illustrated in FIGS. 2Y and 2Z, the crescent shaped protrusion 200AC is also "swept" to further vary resistance between the indicated directions.

It should be understood that the protrusions illustrated in FIGS. 2A-2AD and elsewhere throughout this disclosure are intended merely as examples and should not be viewed as limiting the scope of the present disclosure. Implementations of the present disclosure may include protrusions combining features or characteristics of any of the protrusion designs discussed herein. For example and without limitation, the concave tip illustrated in FIGS. 2M and 2N may be incorporated into protrusions having any suitable base shape. Similarly, "swept" protrusion designs, as illustrated in FIGS. 2O-2R may similarly include any suitable base shape.

While illustrated in FIGS. 2A-2AD as having substantially smooth exterior surfaces, in at least certain implementations, outer surfaces of protrusions in accordance with the present disclosure may instead be selectively roughened or textured to provide additional friction/adhesion. For example and without limitation, such texturing may be applied to the protrusions by grit blasting or otherwise roughening the surfaces of the mold used to produce the protrusions. In such implementations, such additional texturing or roughening of the protrusions surfaces may be about 25 µm or less.

Figure 3:
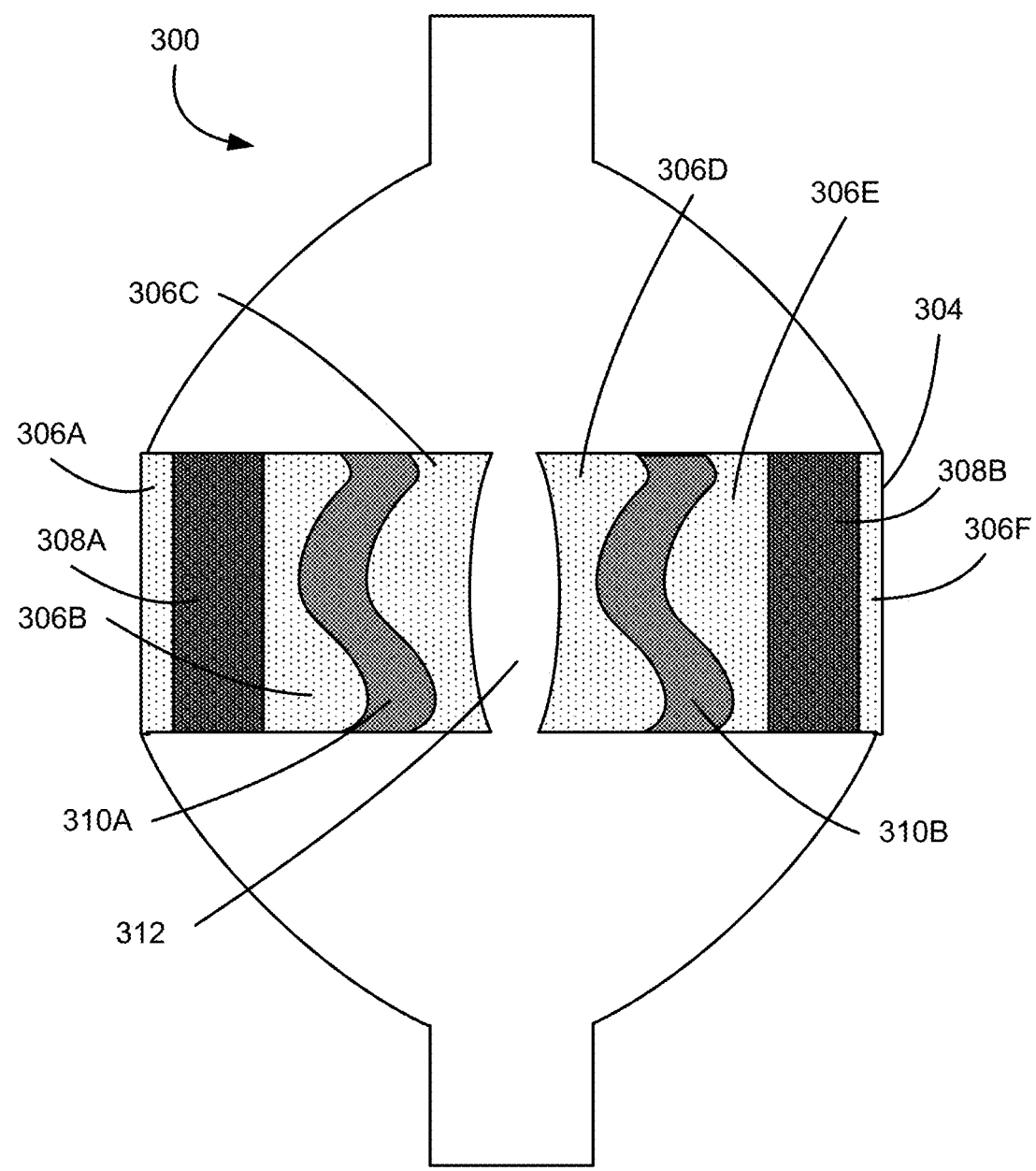
FIG. 3 is a side elevation view of an alternative balloon according to the present disclosure.

The example balloon 102 illustrated in FIGS. 1A-1E included a textured portion 104 having a substantially uniform distribution of protrusions extending therefrom. In contrast, FIG. 3 is a side elevation view of another example balloon 300 in accordance with the present disclosure in a minimally inflated state including a more complicated textured portion 304. More specifically, in contrast to the textured portion 104 of the balloon 102 illustrated in FIG. 1E, which included a substantially uniform pattern and distribution of substantially uniform protrusions, the textured portion 304 includes multiple areas 306A-312 of protrusions. More specifically, the textured portion 304 includes a first set of areas 306A-306F having a relatively low protrusion density; a second set of areas 308A, 308B having a relatively high protrusion density; a third set of areas 310A, 310B having an intermediate protrusion density; and a fourth area 312 that is substantially smooth. Although the areas are described as having different protrusion densities, it should be appreciated that each area may vary in other aspects including, without limitation, one or more of protrusion density, protrusion shape, protrusion rigidity, protrusion distribution pattern, protrusion material, and the like. Similarly, as illustrated in FIG. 3, each area of the textured portion 304 may vary in size and shape.

Referring back to the example medical device 100 of FIGS. 1A-1E, the height of the protrusions 106 may vary in different applications of the present disclosure. For example and without limitation, in at least one implementation the protrusions 106 may be from and including about 5 µm to and including about 700 µm tall when the balloon 102 is in either an uninflated or inflated state. In another implementation, the protrusions may be from and including about 15 µm to and including about 200 µm tall. In yet other implementations, the protrusions may be from and including about 30 µm to and including about 110 µm tall. In at least one specific implementation, the protrusions are from and including about 300 µm to and including about 500 µm to enable the protrusions to penetrate mucosal layers of the physiological lumen. In contrast, in applications in which a mucosal layer may not be present (e.g., cardiac applications), the protrusions may be from and including about 50 µm to and including about 100 µm in height. Although implementations of the present disclosure are not limited to any specific protrusion heights, in at least certain implementations, the protrusions may have an overall height up to and including about 5000 µm or greater. Specific implementations of the present disclosure may also include protrusions having varying heights. Also, individual protrusions may have different portions extending to different heights (e.g., having a crenellated or other top having varying height).

As noted above, protrusion height for a given application may vary depending on the type of physiological lumen within which a balloon is being deployed and, more specifically, the thickness of any fluid layers that may be present. For example and without limitation, the mucosal layer of the colon is generally around 800-900 μm thick while that of the ileum is generally around 400-500 μm thick. Accordingly, to adequately penetrate the respective mucosal layers, balloons intended for deployment in the colon may generally be provided with protrusions of greater length as compared to those of balloons intended for deployment in the ileum. Similar considerations may be made for fluidic layers (e.g., other forms of mucus, sinus fluid, perspiration, etc.) that may be present in other physiological lumens within which balloons according to the present disclosure may be deployed.

Similar to height, the cross-sectional width (e.g., the diameter in the case of protrusions having a circular or ovoid cross-section) of each protrusion may vary. For example and without limitation, in one implementation the protrusions have a cross-sectional width from and including about 5 μm to and including about 1000 μm when the balloon 102 is in either the uninflated or inflated state. In another implementation the protrusions have a cross-sectional width from and including about 25 μm to and including about 300 μm. In yet other embodiments the protrusions have a cross-sectional width from and including about 70 μm to and including about 210 μm. In still another implementation the protrusions have a cross-sectional width from and including about 600 μm to and including about 1000 μm. In yet another implementation the protrusions have a cross-sectional width from and including about 300 μm to and including about 500 μm. In another implementation, the protrusions have a cross-sectional width from and including about 150 μm to and including about 250 μm. In at least one specific implementation, the protrusions have a cross-sectional width of about 400 μm. Implementations of the present disclosure may also include protrusions having varying diameters. Also, individual protrusions may have different portions having different diameters (e.g., a tapering shape). Although protrusion cross-sectional width for implementations of the present disclosure are not limited to any particular ranges or values, in at least certain implementations, the protrusions may have an overall cross-sectional width up to and including about 5000 μm or greater.

In certain implementations, the overall proportions of a protrusion may instead be defined according to an aspect ratio relating the height of the protrusion to the cross-sectional width/diameter of the protrusion. Although any suitable aspect ratio may be used, in one example implementation, the aspect ratio is less than about 5. In another example implementation, the aspect ratio may be from and including about 0.05 to and including about 10. In yet another example implementation the aspect ratio may be from and including about 0.1 to and including about 5.0. In another example implementation the aspect ratio may be from and including about 0.5 to and including about 1.0. In still another example implementation, the aspect ratio may be from and including about 1.0 to and including about 10.0. In another implementation, the aspect ratio may be from and including about 0.1 to and including about 1. In still another implementation, the aspect ratio may be from and including about 1 to and including about 2. In yet another example implementation, the aspect ratio may be about 0.5, about 1.0, or about 2.0. It should also be appreciated that the aspect ratio for protrusions within a given implementation of the present disclosure may vary such that a first set of protrusions of a balloon conforms to a first aspect ratio while a second set of protrusions for the same balloon conforms to a second aspect ratio. Moreover the cross-sectional width/diameter of the protrusion for purposes of determining an aspect ratio may be any measure of cross-sectional width/diameter. For example, the cross-sectional width/diameter may be the maximum cross-sectional width/diameter of the protrusion, the minimum cross-sectional width/diameter of the protrusion, an average cross-sectional width/diameter of the protrusion, or the cross-sectional width/diameter of the protrusion at a particular location along the length of the protrusion.

The protrusions may also be configured to have a particular stiffness to avoid inadvertent bending or deformation while still allowing engagement of the protrusions with biological tissue. In at least certain implementations, the protrusions are formed such that they have a stiffness that is at least equal to the tissue with which the protrusions. For example, in certain implementations, the stiffness of the protrusions is from and including about 1.0 to and including 2.0 times that of the tissue with which it is to engage. The stiffness may also be expressed as a modulus of elasticity of the material from which the protrusions are formed. For example, in at least some implementations, the protrusions are formed from a material having a modulus of elasticity from and including about 50 kPa to and including about 105 kPa. In other implementations including stiffer protrusions, the protrusions may be formed of a material having a modulus of elasticity from and including about 0.8 MPa to and including about 2.0 MPa.

In certain implementations, protrusions of balloons in accordance with the present disclosure may be configured to deform in response to a strain being applied to the balloon. Such deformation may then be used to dynamically control and adjust traction between the balloon and biological tissue.

Figure 4A:
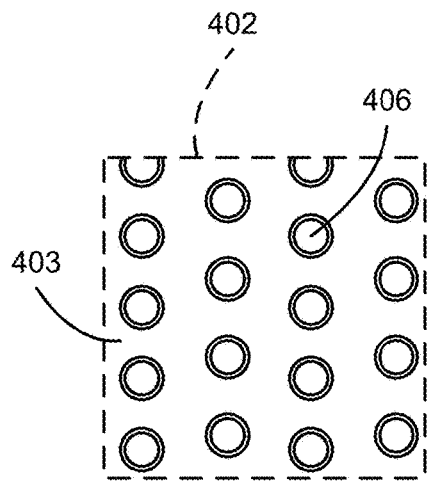
FIG. 4A is a schematic illustration of a textured portion of a balloon according to the present disclosure in a first state of strain.
Figure 4B:
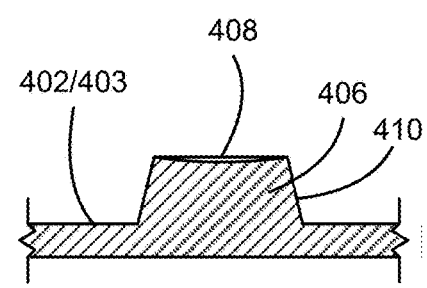
FIG. 4B is a cross-sectional view of a protrusion of the balloon of FIG. 4A.
Figure 5A:
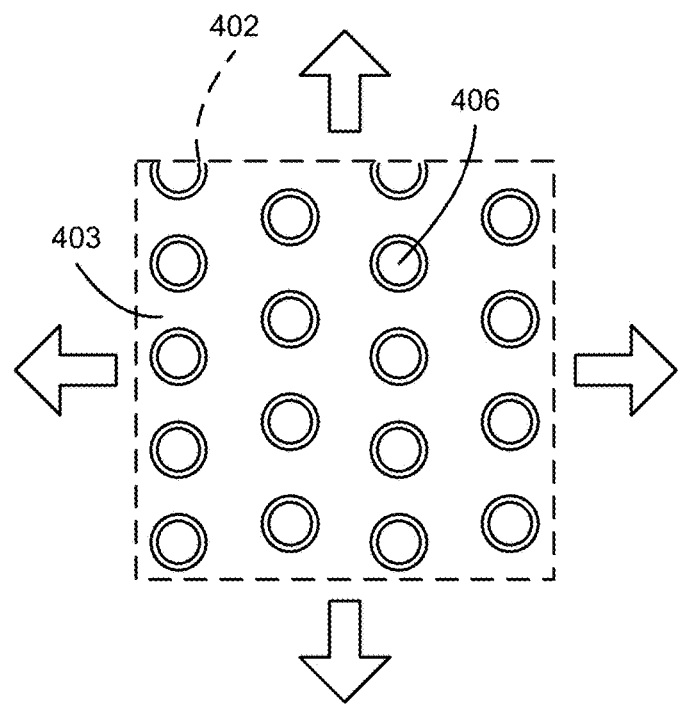
FIG. 5A is a schematic illustration of the textured portion of the balloon of FIG. 4A in a second state of strain.
Figure 5B:
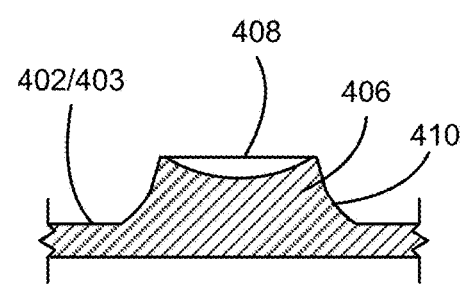
FIG. 5B is a cross-sectional view of the protrusion of FIG. 4B when the balloon of FIG. 4A is in the second state of strain.

FIG. 4A illustrates a portion of a balloon 402 or similar structure in a first state of strain. In certain applications, the first state of strain may correspond to an unstrained state or, alternatively, may correspond to a state in which a first strain is applied to the balloon 402. As shown, the balloon 402 includes multiple protrusions, such as protrusion, 406 distributed across and extending from a surface 403 of the balloon 402. As illustrated in FIG. 4B, the protrusions 406 may, in certain implementations, have a frustoconical shape. FIG. 5A illustrates the portion of the balloon 402 in a second state of strain, in which a strain greater than that of the first state of strain is applied to the balloon 402. As shown in FIG. 5A, in at least some applications, the applied strain when in the second state of strain may be biaxial. Such strain may result, for example, from inflation of the balloon 402. As illustrated in FIG. 5A, the application of strain generally results in both the distance between adjacent protrusions increasing as well as a stretching/deformation of the protrusions. FIG. 5B is a cross-sectional view of the protrusion 406 when a biaxial strain is applied to the balloon 402. As illustrated, the frustoconical shape of the protrusion 406 deforms under the biaxial strain. In particular, each of a top surface 408 and side wall 410 of the protrusion 406 become increasingly concave in response to the application of biaxial strain.

The term "biaxial strain" is generally used herein to refer to a strain applied along two axes which, in certain implementations, may be perpendicular to each other. In certain cases, the biaxial strain may be approximately equal along each axis. For example, strain applied to the balloon may be equal in each of a longitudinal direction and a transverse direction. However, in other implementations, strain may be applied unequally along the axes, including strain resulting in non-uniform deformation of the protrusions (e.g., elongation of compression primarily along a single axis). Moreover, sufficient deformation of the protrusions may also be achieved by application of a uniaxial strain or a multiaxial strain other than a biaxial strain. Accordingly, while the examples described herein are primarily discussed with reference to a biaxial strain resulting in variations in frictional and adhesive engagement resulting from deformation of the protrusion, implementations of the present disclosure are more generally directed to variations in frictional and adhesive engagement from deformation of the protrusions in response to any applied strain.

FIGS. 6A and 6B are cross-sectional views of the protrusion 406 illustrating further details of the protrusion in a strained and unstrained state, respectively. As illustrated in FIG. 6A, when in the unstrained state, the protrusion 406 has a top diameter (D1) corresponding to the top surface 408 of the protrusion and a base diameter (D2) corresponding to a base 412 of the protrusion 406. The top surface 408 of the protrusion 406 is shown as being disposed at a maximum height (H). The top surface 408 is also shown as being concave and having a concavity defined by a radius of curvature (R). The top surface 408 of the protrusion reaches a height (H) relative to the surface 403 of the balloon 402. It should be appreciated that while the top surface 408 of the protrusion is shown in FIG. 6A as being concave, in other implementations, the top surface 408 may be substantially flat. Also, while the top diameter D1 and base diameter D2 are illustrated in FIG. 6A as being different, in other implementations D1 and D2 may be equal such that the protrusion 406 is substantially cylindrical in shape.

As shown in FIG. 6B, the protrusion 406 may deform in response to a strain applied to the balloon 402. In particular, each of the top diameter (D1) and the base diameter (D2) may expand to a second base diameter (D1') and a second base diameter (D2'), respectively. The radius of curvature (R) of the top surface 408 may also decrease to a second radius of curvature (R'), thereby causing the top surface 408 to become increasingly concave. In addition to the foregoing dimensional changes, the overall height of the protrusion 406 may change from the initial height (H) to a second height (H').

As illustrated in FIGS. 6A and 6B, in at least some implementations of the present disclosure, each protrusion may include a lip or edge 414 at the transition between the side wall 410 and the top surface 408. In general, a relatively sharp lip or edge 414 may allow the protrusions to more readily engage the wall of the physiological lumen and may also facilitate penetration of mucosal or other layers that may be present on the wall. Accordingly, in at least some implementations, the edge/lip 414 may have a radius of no more than about 3 µm.

The initial dimensions of the protrusion 406 may vary. For example, in certain implementations the unstrained upper diameter (D1) of the protrusion may be from and including about 100 µm to and including about 700 µm; the unstrained lower diameter (D2) of the protrusion may be from and including about 100 µm to and including about 750 µm; the unstrained height (H) of the protrusion may be from and including about 100 µm to and including about 700 µm; and the unstrained radius of curvature (R) of the top surface 408 of the protrusion may be from and including about 1 mm to and including about 2 mm. Similarly, in certain implementations, the strained upper diameter (D1') of the protrusion may be from and including about 375 µm to and including about 750 µm; the strained lower diameter (D2') of the protrusion may be from and including about 405 µm to and including about 825 µm; the strained height (H') of the protrusion may be from and including about 200 µm to and including about 400 µm; and the strained radius of curvature (R') of the top surface 408 of the protrusion may be from and including about 500 µm to and including about 750 µm. In one specific example, the D1 may be about 250 µm, D2 may be about 270 µm, H may be about 500 µm, and R may be about 1.5 mm. In the same example, the balloon 402 may be configured to be strained such that D1' can be up to about 375 µm, D2' can be up to about 400 µm; H' may be decreased down to about 450 µm, and R' may be decreased down to about 500 µm. In other implementations, deformation of the protrusion 406 in response to a strain applied to the balloon 402 may instead be based on a change in the surface area of the protrusion 406. For example and without limitation, the balloon 402 may be configured such that the surface area of the protrusion 406 may increase up to about 25%.

During experimental testing, it was observed that separation force between a piece of material including protrusions similar to the protrusion 406 of FIGS. 6A and 6B and a flexible probe simulating biological tissue varied with the degree of biaxial stain applied to the material. More specifically, the probe was first made to contact the material sample, causing the probe to adhere to the material sample. The probe was then withdrawn from contact with the material sample. The force required to affect such separation was measured and observed to vary non-linearly with the degree of biaxial strain applied to the material sample.

As indicated in FIG. 6A, the protrusion 406 may be further characterized by the sharpness of the edge 414 at the transition between the side wall 410 and the top surface 408 of the protrusion 406. Although the edge 414 is not limited to specific degrees of sharpness, testing has indicated that particular sharpness ranges can be advantageous in fixing balloons in accordance with this disclosure within a physiological lumen, particular in the presence of mucus and other similar fluids that may be secreted or disposed along the inner surface of the physiological lumen. More specifically, sufficient sharpness of the edge 414 appears to facilitate penetration through layers of mucus (or similar fluids) to facilitate engagement between the balloon and inner wall of the lumen. Accordingly, in at least certain implementations, the edge 414 between the side wall 410 and the top surface 408 may have a radius from and including about 25 µm to and including about 500 µm, for example 75 µm. In other implementations, the radius is not greater than about 25 µm.

Figure 7:
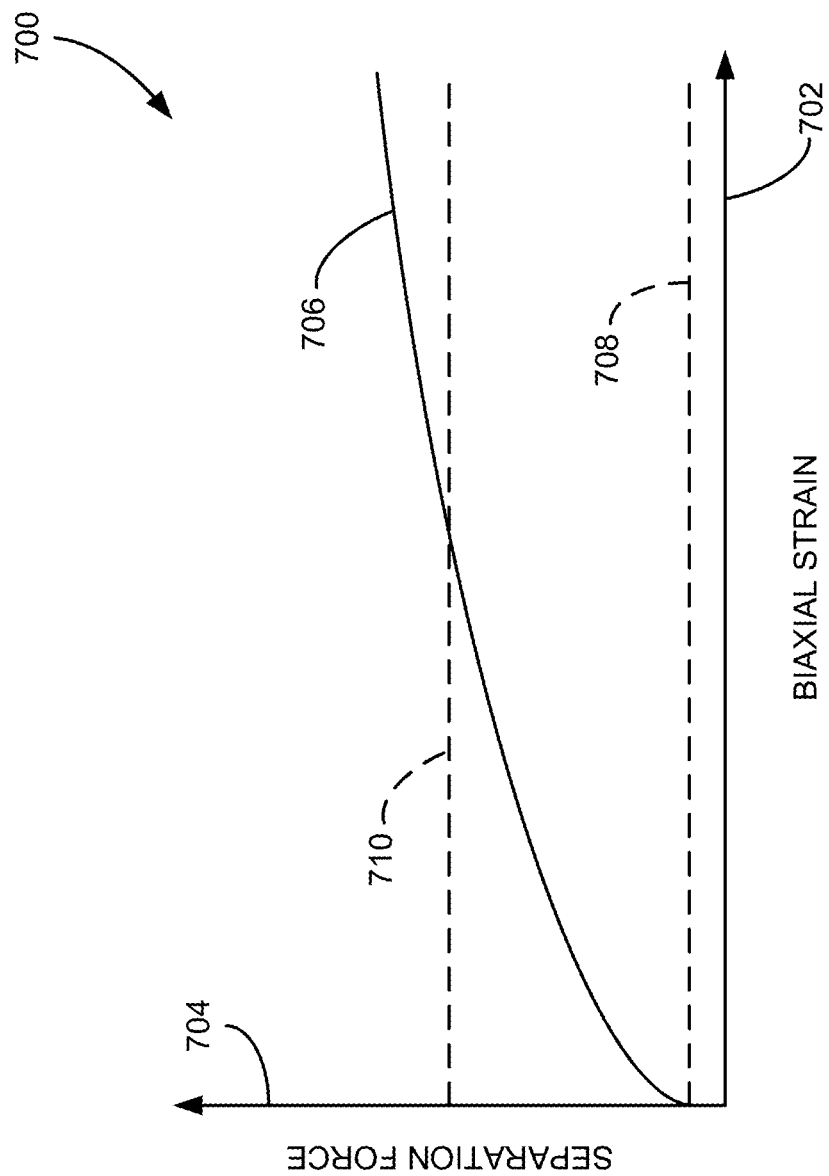
FIG. 7 is a graph illustrating an example relationship between separation force and a strain applied to a balloon in accordance with the present disclosure.

FIG. 7 is a graph 700 summarizing the experimental findings regarding the relationship between separation force and biaxial strain. More specifically, the graph 700 includes a first axis 702 corresponding to biaxial strain and a second axis 704 corresponding to the measured separation force when separating the probe and material sample. As indicated by line 706, the separation force varied in a non-linear fashion in response to changes in biaxial strain.

The graph 700 further indicates a base separation force line 708 corresponding to the separation force when the material sample is unstrained. The graph further includes a "flat" separation force line 710 corresponding to a second material sample substantially similar to the tested material sample but lacking any protrusions.

As illustrated in the graph 700, the separation force for the material having the protrusions may be varied to have a range of values by changing the biaxial strain applied to the material. For example, by applying no or relatively low biaxial strain, the material with protrusions may actually be made to have less separation force (i.e., be made to be less frictional and/or adhesive) than a flat sheet of the same material. However, as biaxial strain is increased friction and adhesion also increase such that, at a certain level of biaxial strain, the separation force of the material including protrusions may be made to exceed that of a flat sheet of the same material.

As shown in the graph 700, this may, in certain implementations, reduce the separation force when unstrained as compared to separation force of a flat material sheet. However, as strain is increased, the separation force may increase above that of the flat sheet. In other words, by selectively applying biaxial strain to the material sample, separation force may be varied, providing physicians with increased control and more reliable engagement for medical devices incorporating balloons in accordance with the present disclosure.

The specific example discussed in FIGS. 4A-7 generally includes protrusions having a flat or partially concave top surface that, when a strain is applied, causes the protrusions to become increasingly concave, thereby increasing their surface area. In other implementations of the present disclosure, the protrusions may instead include a rounded/convex or similar top surface such that when a strain is applied, the top surfaces of the protrusions at least partially flatten. Such flattening may result in a reduction of the surface area and, as a result, a change (generally a reduction) in the separation force between the protrusions and the physiological lumen. Accordingly, whereas in the previous examples a strain is applied to increase protrusion surface area to increase separation force, strain may also be used to decrease protrusion surface area and, as a result, decrease separation force. In either case, however, strain is used as the primary mechanism for altering the shape and the result separation force of the protrusions.

The separation force between the balloon and the physiological lumen may vary across different implementations of the present disclosure and across different states of inflation for any given implementation. However, in at least some implementations, the balloon may be configured to have a separation force less than about 5 N when the balloon is in its deflated state (e.g., as illustrated in FIGS. 1A-1B) to facilitate translation of the balloon along the physiological lumen with minimal adhesion and friction. In other implementations, the separation force when in the deflated state may be less than about 3 N. In a specific example, the separation force in the deflated state may be about 1 N. The balloon may also be configured to have a particular separation force in a minimally inflated state in which the balloon substantially engages the physiological lumen. For example, in at least some implementations, the separation force in the minimally inflated state may be from and including about 10 N to and including about 30 N. In other implementations, the separation force in the minimally inflated state may be from and including about 15 N to and including about 25 N. In one specific implementation, the separation force in the minimally inflated state may be about 20 N.

As previously discussed, in at least some implementations, a strain on the balloon may be applied or modified (e.g., by inflating or deflating the balloon) to modify the adhesive and frictional characteristics of the balloon and, as a result, the separation force between the balloon and physiological lumen. In one implementation, the separation force relative to a minimally inflated state may be reduced to 1% or lower by deflating the balloon and up to and including 200% by overinflating and straining the balloon. In another implementation, the deflated balloon may have a separation force of less than about 5% of the minimally inflated state and a maximum of about 150% by straining the balloon. In still another example implementation, the balloon may have a lower bound separation force of less than about 5% of the minimally inflated state and a maximum of about 125% by straining the balloon. Accordingly, in at least one specific example, the balloon may have a separation force of about 20 N in the inflated state, about 1 N in the deflated state, and about 25 N in a maximum strained state.

Figure 8:
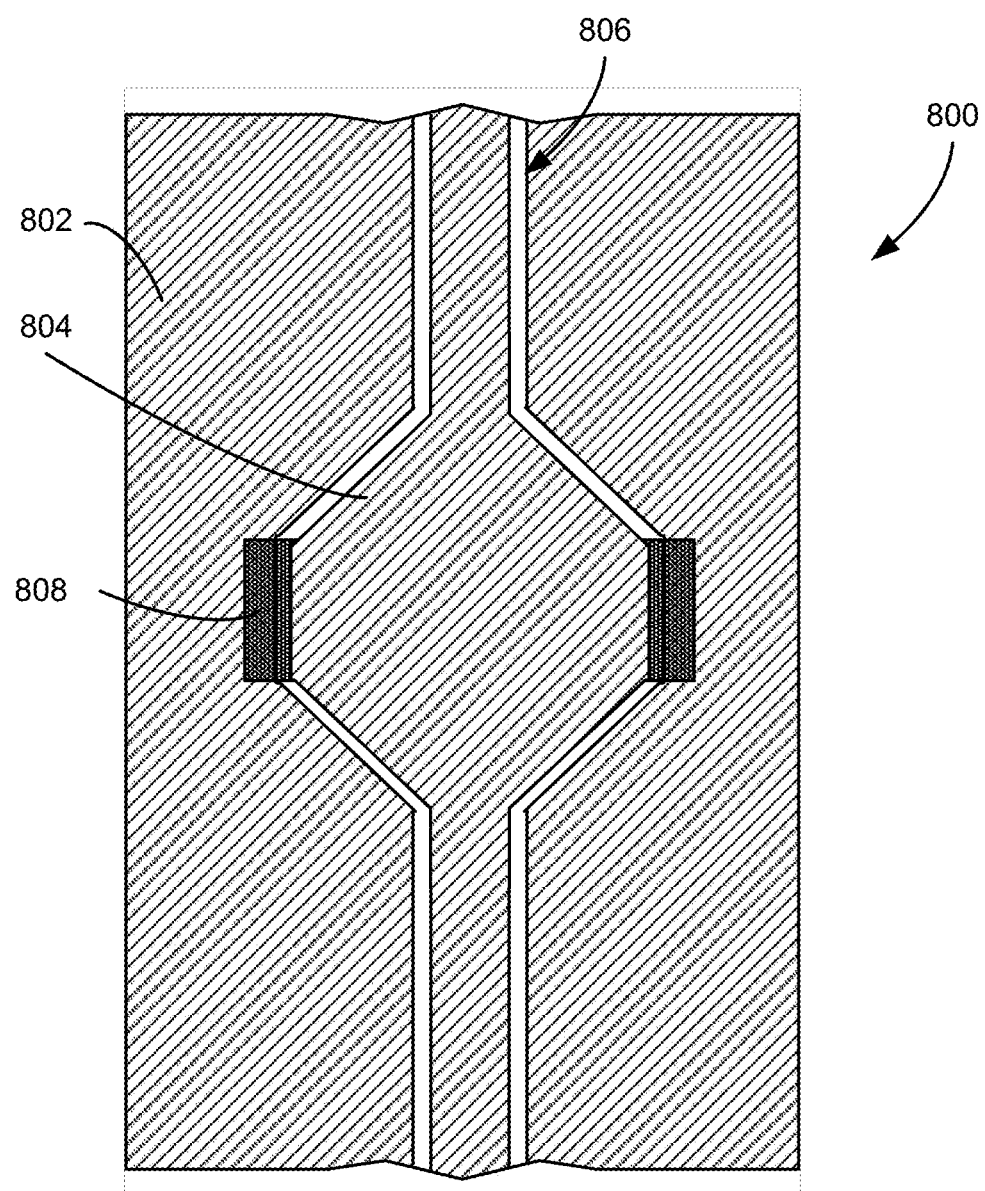
FIG. 8 is a cross-sectional view of a first mold for manufacturing balloons in accordance with the present disclosure.

As previously noted, balloons in accordance with the present disclosure may be manufactured in various ways. For example, in at least one implementation, balloons including protrusions as discussed above may be manufactured through a casting process. FIG. 8 illustrates an example mold 800 for use in such a casting process. As illustrated the mold 800 includes an outer mold piece 802 within which an inner mold piece or core 804 is disposed. The combination of the outer mold piece 802 and the core 804 defines a cavity 806 providing the general shape of the balloon to be molded.

In addition to the outer mold piece 802 and the core 806, the mold 800 includes an insert 808 for forming protrusions on the balloon during casting. The insert 808 is separately formed to have the pattern and distribution of protrusion to be included on the final balloon. The insert 808 may be manufactured in various ways including, without limitation, machining, 3D printing, microlithography, or any other similar manufacturing process. Once formed, the insert 808 may be disposed within and coupled to the outer mold piece 802. In certain implementations, the insert 808 may be formed from a semi-rigid material such as, but not limited to, Kapton® or other polyimide material, silicone, latex, or rubber.

During the casting process, balloon material (such as but no limited to ECOFLEX® 50) is poured into the cavity and allowed to set. In certain implementations, a vacuum is also applied to the mold 800 to remove air from the mold cavity 806 and to facilitate the material poured into the cavity 806 to take on the shape of the mold cavity 806, including the protrusions defined by the mold insert 808.

In certain implementations, the overall thickness of the balloon may be modified by changing the thickness of the cavity 806. For example, the outer mold piece 802 may be configured to receive cores of varying sizes such that the thickness of the cavity 806 defined between the outer mold piece 802 and the core 804 may be modified by swapping cores into the mold 800.

Although illustrated in FIG. 8 as having a substantially uniform width, the cavity 806 defined between the outer mold piece 802 and the core 804 may also be non-uniform such that the cavity 806 is wider at certain locations within the mold 800. Accordingly, any balloon formed using the mold 800 will have corresponding variations in its thickness. By varying the thickness of the balloon, various characteristics may be imparted to the balloon. For example, the thickness of certain locations of the balloon may be increased to improve the overall durability and strength of the locations. In other cases, the thickness of the balloon may be varied such that reinforced regions of the balloon are formed that cause the balloon to collapse and/or expand in a particular way. Such reinforced regions may also cause the balloon to assume a particular shape in any of a deflated state, partially inflated state, or fully inflated state.

Figure 9:
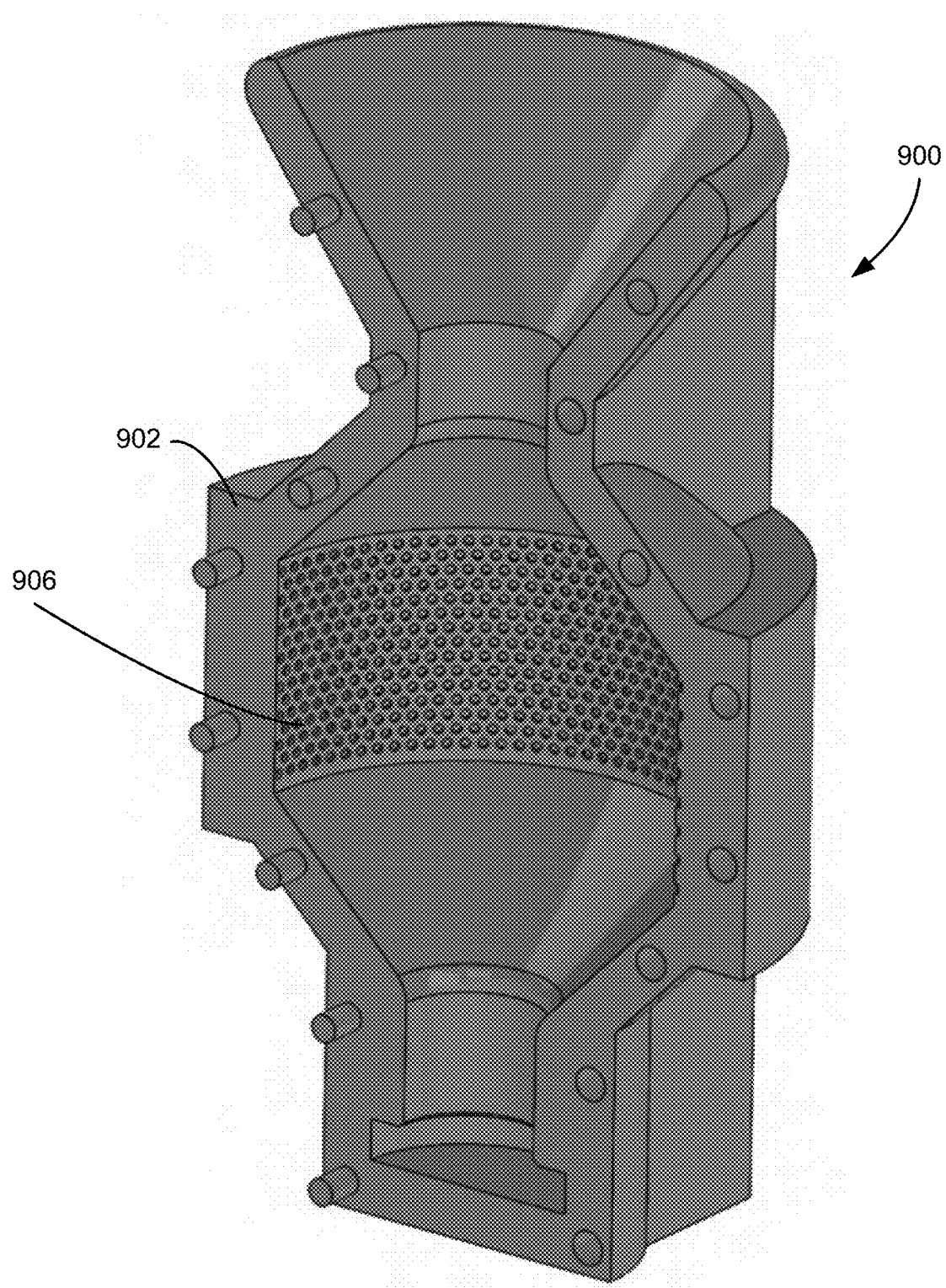
FIG. 9 is an isometric view of a second mold for manufacturing balloons in accordance with the present disclosure.

FIG. 9 is an isometric view of an alternative mold 900 for use in manufacturing balloons in accordance with the present disclosure. The mold 900 includes an outer mold piece 902 within which an inner mold piece or core (not shown) may be disposed. In contrast to the mold 800 of FIG. 8 in which a removable insert 808 is used to form the balloon protrusions, the outer mold piece 902 includes voids 906 formed directly into an inner surface 908 of the outer mold piece 902 that are used to form the protrusions during the casting process.

As discussed above, in at least some implementations, balloons in accordance with the present disclosure may be formed using a casting process. Such casting processes may include piece casting, slush casting, drip casting, or any other similar casting method suitable for manufacturing a hollow article. In a slush casting process, for example, an amount of material may be added to the mold and slushed to coat the internal surface of the mold prior to the material setting. Other fabrication methods may also be implemented including, without limitation, various types of molding (e.g., injection molding) and extrusion processes.

While previous fabrication methods included integrally forming the protrusions with the balloon, in other implementations the protrusions may instead be formed onto a previously formed balloon. For example, in at least one other fabrication method, a base balloon may first be formed. The protrusions may then be formed or coupled to the balloon using a subsequent process. In one example fabrication method, the base balloon is extruded and then the protrusions are then added to the base balloon using a spray method. In another example fabrication method, the base balloon is formed using a first casting or molding process and, once the base balloon is set, a second casting or molding process (e.g., an over-molding process) is applied to form the protrusions on the exterior surface of the base balloon.

As previously discuss in the context of FIGS. 1A-1E, balloons in accordance with the present disclosure may be implemented for use in various medical devices. FIGS. 10-16 are schematic illustrations of various example medical devices and configurations of such medical devices including balloons of the present disclosure. It should be appreciated that the medical devices provided are merely example devices and are therefore non-limiting. More generally, balloons in accordance with the present disclosure may be used in conjunction with any medical device adapted to be inserted into a physiological lumen. In certain implementations, the medical device may include a lumen running its length. The device lumen may serve as a tool or catheter port such that tools and/or catheters can be threaded down the length of the medical device and out of a distal end of the device. Alternatively, the device may be threaded onto tools or catheters already disposed within the physiological lumen.

Figure 10:
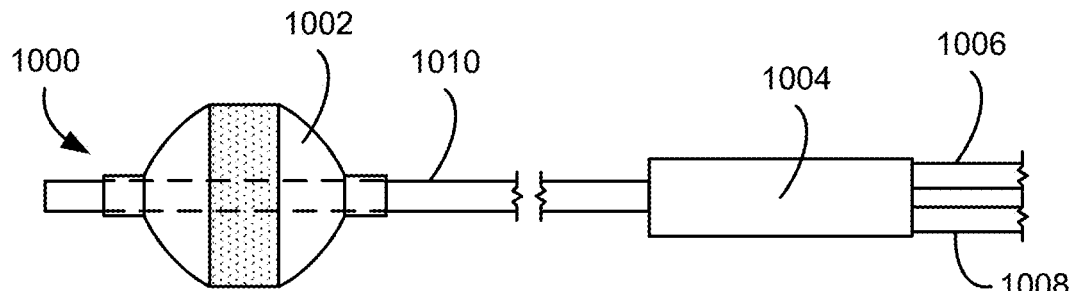
FIG. 10 is a schematic illustration of a medical device in the form of a catheter delivery tool in accordance with the present disclosure.

FIG. 10 is a schematic illustration of a first medical device 1000 in the form of a catheter delivery tool. As illustrated, the medical device 1000 includes a proximal hub 1004 from which each of a catheter tool channel 1006 and a balloon insufflation channel 1008. A distal portion 1010 of the catheter tool channel 1006 extends from the hub 1004 and includes a balloon 1002 that may be selectively inflated and deflated by providing air to or allowing air to escape from the balloon 1002 via the balloon insufflation channel 1008, respectively. Accordingly, the distal portion 1010 may be inserted into a physiological lumen of a patient with the balloon deflated. Once located at a point of interest within the physiological lumen, air may be provided to the balloon 1002 via the balloon insufflation channel 1008 to cause the balloon 1002 to expand and engage the wall of the physiological lumen. When so engaged, the catheter tool channel 1006 may be used to provide a clear and direct pathway to the location of interest.

The medical device 1000 is described above as being used in conjunction with or to guide a catheter or guide wire within the physiological lumen; however, in other implementations of the present disclosure, balloons in accordance with the present disclosure may be incorporated into catheters or guide wires. For example and without limitation in at least one implementation of the present disclosure an inflatable balloon as described herein may be disposed along a guide wire or catheter (e.g., at or near distal end of the guide wire or catheter). In such implementations, the guidewire or catheter may be inserted into a physiological lumen with the balloon in the deflated state. The balloon may be subsequently inflated to engage the physiological lumen and at least partially anchor the guide wire or catheter within the physiological lumen.

Figure 11:
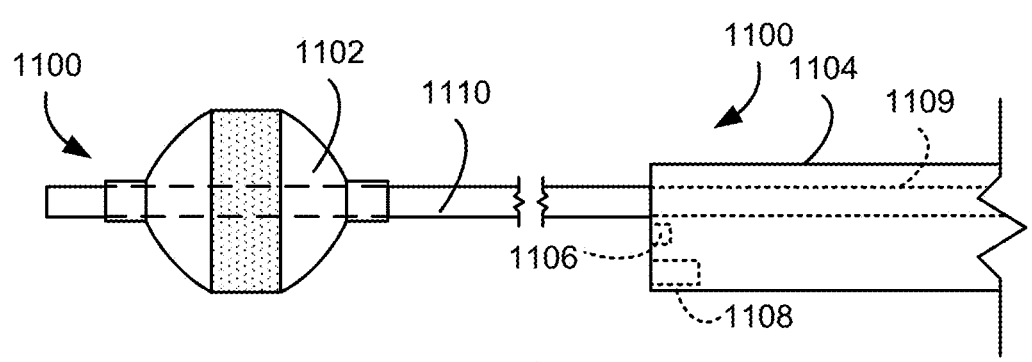
FIG. 11 is a schematic illustration of an example endoscopic medical device in accordance with the present disclosure and including a catheter-mounted balloon.

FIG. 11 is a schematic illustration of a second medical device 1100, which may be an endoscopic device. The second medical device 1100 includes an endoscope body 1104 that may include, for example and without limitation, a light emitting diode (LED) 1106 and a camera 1108. The endoscope body 1104 may also define a catheter channel 1109 through which a catheter 1110 may be inserted. As illustrated in FIG. 11, the catheter 1110 may include a distal balloon 1102 that may be used to at least partially secure the catheter 1110 within a physiological lumen.

In one example application of the medical device 1100, the catheter 1110 may be used as a guide for the endoscope body 1104. More specifically, during a first process the catheter 1110 may be delivered to a point of interest along a physiological lumen with the balloon 1102 in an uninflated state. Once located, the balloon 1102 may be inflated to engage the balloon 1102 with the lumen and at least partially secure the catheter within the lumen. The endoscope body 1104 may then be placed onto the catheter 1110 such that the endoscope body 1104 may be moved along the catheter 1110, using the catheter as a guide.

Figure 12:
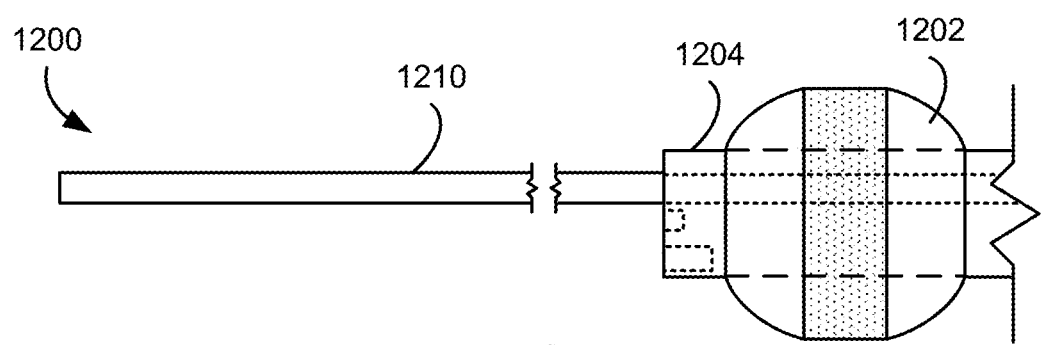
FIG. 12 is a schematic illustration of a second example endoscopic medical device in accordance with the present disclosure and including an endoscope-mounted balloon.

FIG. 12 is a schematic illustration of a third medical device 1200. Similar to the medical device 1100 of FIG. 11, the medical device 1200 includes an endoscope body 1204 (or body of a similar tool) that may be configured to receive a catheter 1210. However, in contrast to the medical device 1100 of FIG. 11 in which the balloon 1102 was coupled to the catheter 1110, the medical device 1200 includes a balloon 1202 coupled to the endoscope body 1204 and which may be used to at least partially secure the endoscope body 1204 within a physiological lumen of a patient.

Figure 13:
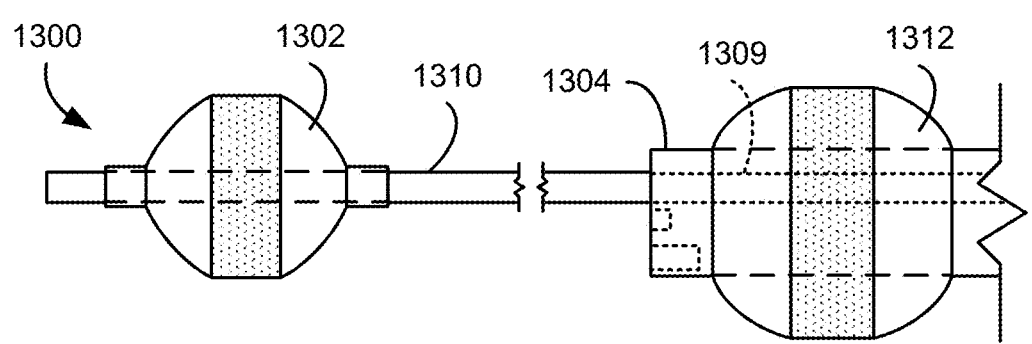
FIG. 13 is a schematic illustration of a third example endoscopic medical device in accordance with the present disclosure and including each of a catheter-mounted balloon and an endoscope-mounted balloon.

FIG. 13 is a schematic illustration of a fourth medical device 1300 that combines aspects of both the medical device 1100 of FIG. 11 and the medical device 1200 of FIG. 12. More specifically, the medical device 1300 includes an endoscope body 1304 that defines a catheter channel 1309 through which a catheter 1310 may be inserted. Like the medical device 1100 of FIG. 11, the catheter 1310 includes a distal balloon 1302 that may be used to at least partially secure the catheter 1310 within a physiological lumen. Also, like the medical device 1200 of FIG. 12, the endoscope body 1304 also includes a balloon 1312.

Figure 17:
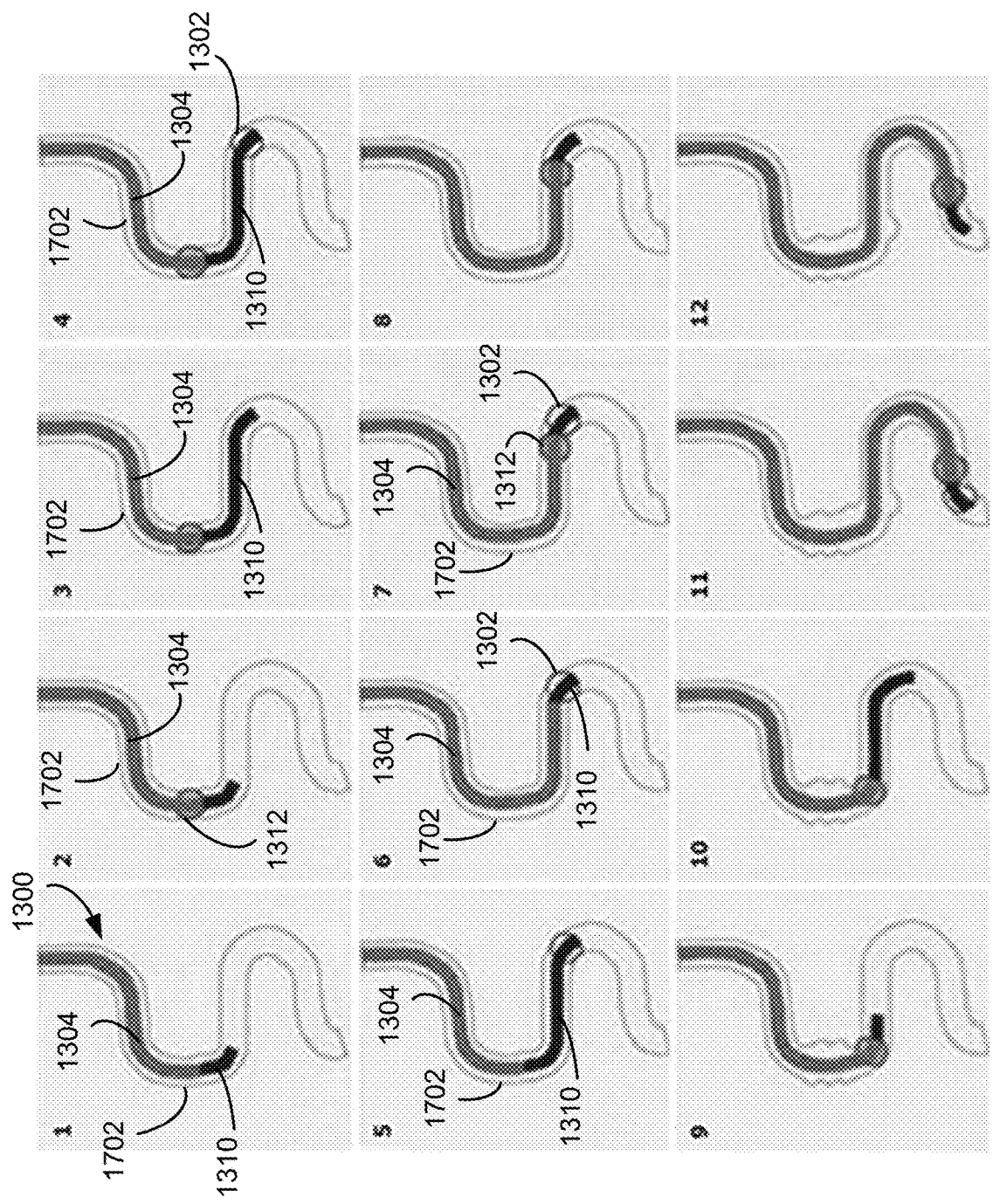
FIG. 17 is a graphical illustration of an example medical procedure performed using the medical device of FIG. 13.

The two-balloon configuration of the medical device 1300 may be used to progress the medical device 1300 along the physiological lumen. For example, FIG. 17 provides a series of illustrations depicting progression of the medical device 1300 along a physiological lumen 1702 (indicated in Frame 1). As illustrated, the medical device 1300 may first be inserted into the physiological lumen in an uninflated/ disengaged configuration (Frame 1). The endoscope balloon 1312 may then be inflated to engage the balloon 1312 with the lumen 1702 and to at least partially secure the endoscope body 1304 within the lumen 1702 (Frame 2). With the endoscope body 1304 secured, the catheter 1310 may then be extended from the endoscope body 1304 along the lumen (Frame 3) and the catheter balloon 1302 may be engaged with the lumen 1702 at a second location by inflating the catheter balloon 1302 at the second location (Frame 4). The endoscope balloon 1312 may then be deflated (Frame 5) and the endoscope body 1304 may be progressed along the lumen 1702 using the anchored catheter 1310 as a guide (Frame 6). When the endoscope body 1304 reaches the catheter balloon 1302, the endoscope body 1304 may again be secured within the lumen 1702 by inflating the endoscope body balloon 1312 (Frame 7). As illustrated in Frames 8-12, this process may be repeated to progress the medical device 1300 along the physiological lumen 1702.

In certain implementations, the medical device may be a double balloon endoscope comprising a flexible overtube, as described in PCT Application Publication WO 2017/ 096350, wherein at least a portion of the outer surface of one or both of the first and second inflatable balloons comprises a micro-patterned surface as described herein. In other embodiments, the endoscope does not comprise an overtube.

Figure 14:
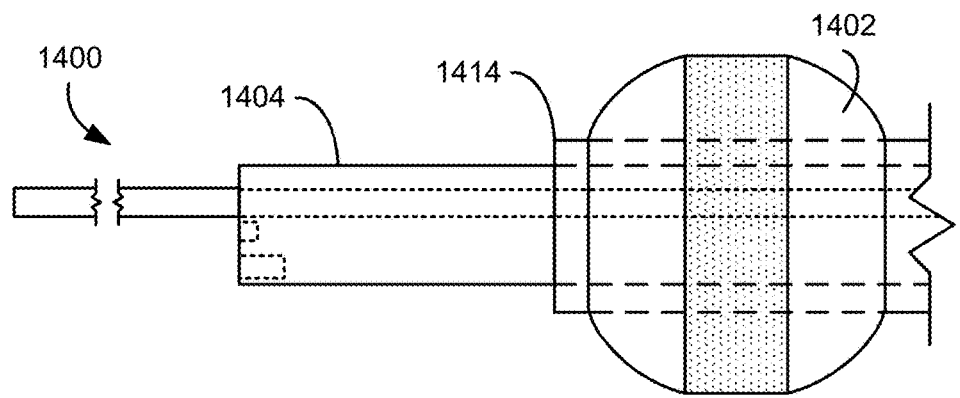
FIG. 14 is a schematic illustration of a fourth example endoscopic medical device in accordance with the present disclosure and including an overtube-mounted balloon.
Figure 15:
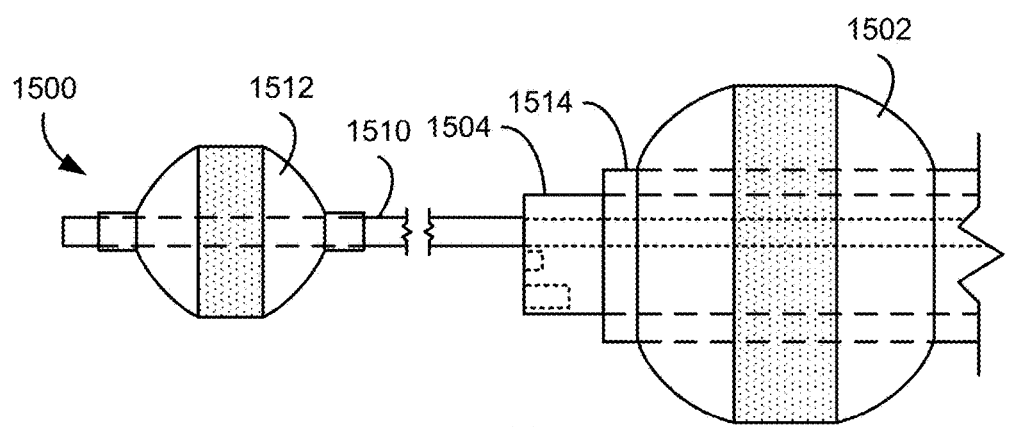
FIG. 15 is a schematic illustration of a fifth example endoscopic medical device in accordance with the present disclosure and including each of a catheter-mounted balloon and an endoscope-mounted balloon.
Figure 16:
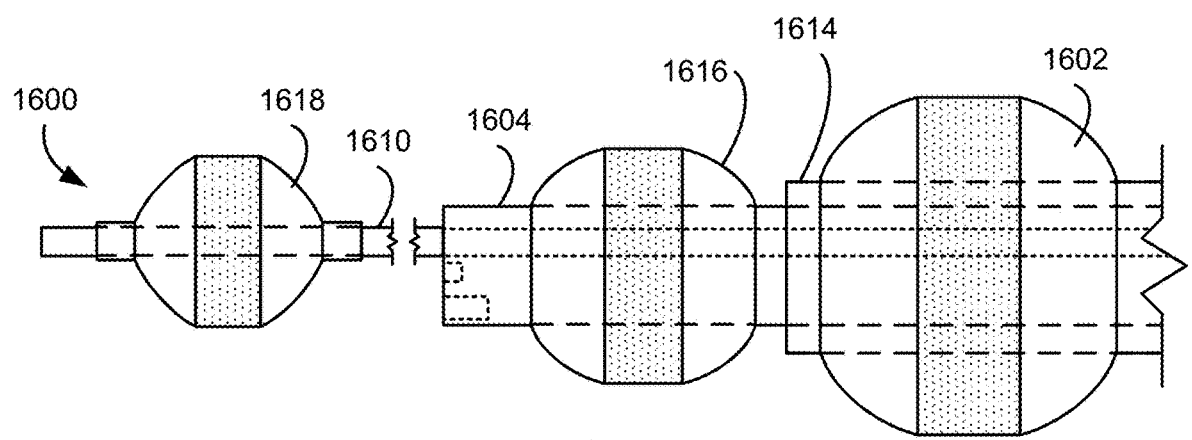
FIG. 16 is a schematic illustration of a sixth example endoscopic medical device in accordance with the present disclosure and including each of a catheter-mounted balloon, an endoscope-mounted balloon, and an overtube-mounted balloon.

FIGS. 14-16 illustrate additional variations of the foregoing example medical devices. FIG. 14 is a schematic illustration of a medical device 1400 in which a balloon 1402 is coupled to an overtube 1414 through which an endoscope device 1404 may be inserted. FIG. 15 is a schematic illustration of a medical device 1500 similar to that of FIG. 14 in that it includes a balloon 1502 coupled to an overtube 1514 through which an endoscope body 1504 extends. In addition to the overtube balloon 1502, the medical device 1500 includes a catheter balloon 1512 coupled to a distal end of a catheter 1510 extending through the endoscope body 1504. An example double balloon endoscope device similar to that of FIG. 15 and including a flexible overtube is described in detail in PCT Application Publication WO 2017/096350, which is incorporated herein by reference in its entirety. Finally, FIG. 16 is another schematic illustration of a medical device 1600 including three distinct balloons. Specifically, the medical device 1600 includes a first balloon 1602 coupled to an overtube 1614, a second balloon 1616 coupled to an endoscope body 1604 extending through the overtube 1614, and a third balloon 1618 coupled to a catheter 1610 extending from the endoscope body 1604.

In each of the medical tools, it is assumed that the described devices include suitable channels for delivering air or other fluid to the disclosed balloons to inflate the balloons and for removing air/fluid from the balloons to deflate the balloons. For example, each device may include a proximal manifold or coupling that may be connected to a pump or other fluid supply and that further includes a vent or return channel through which fluid may be removed from the balloons. In certain implementations, the medical device includes tubing that is in fluidic communication with one or more balloons of the device, the tubing allowing for controlled inflation and/or deflation of one or more of the balloons. In implementations in which the medical device includes multiple balloons, the tubing used to inflate one or more of the multiple balloons. Alternatively, different sets of tubing may be used to independently control inflation and deflation of respective subsets of the balloons of the medical device.

It should also be appreciated that in implementations of the present disclosure having multiple balloons, only one balloon need to have protrusions in accordance with the present disclosure. In other words, medical devices in accordance with the present disclosure my include one textured balloon as described herein, but may also include any number of non-textured balloons or balloons having designs other than those described herein. Moreover, while the example medical devices of FIGS. 10-17 illustrate balloons located near the distal end of components of the medical devices (e.g., catheters, endoscope bodies, overtubes), in other implementations, balloons may be disposed at any location along such components, including at multiple locations along a given component.

Figure 18:
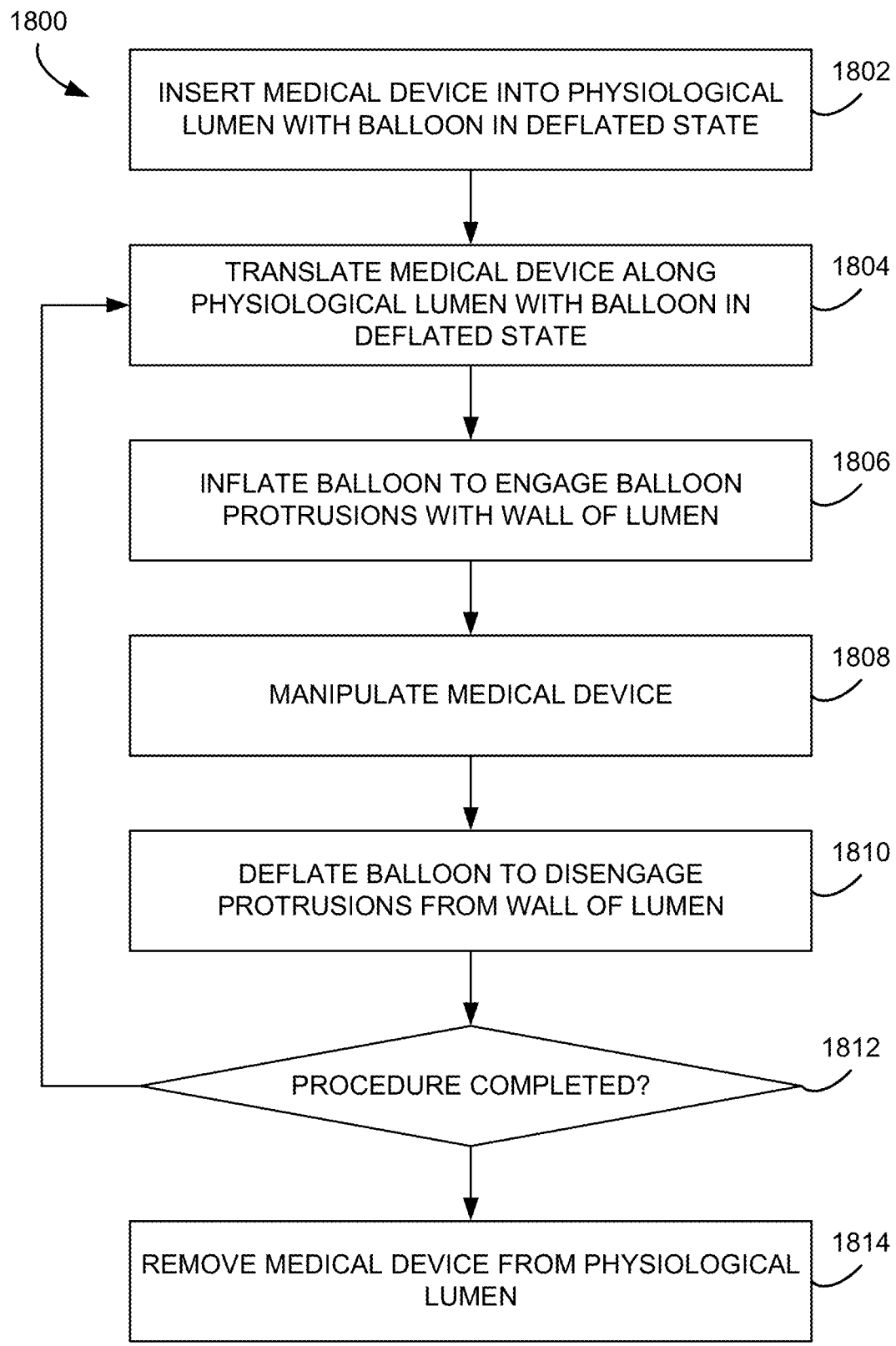
FIG. 18 is a flowchart illustrating an example method of performing a procedure using a medical device according to the present disclosure.

The current disclosure further provides methods of performing endoscopy or similar medical procedures within a body cavity. FIG. 18 is a flowchart illustrating an example method 1800 of such procedures which may be generally performed using medical devices in accordance with the present disclosure, including but not limited to the medical devices discussed in the context of FIGS. 1A-1E and 10-17.

At operation 1802, the medical device is introduced into a physiological lumen or body cavity at least with a balloon of the medical device in a deflated state. As previously discussed, in at least one application of the present disclosure, the physiological lumen may include (but is not limited to) a portion of a patient's GI tract. For example, in the context of a small bowel endoscopy, the physiological lumen may correspond to a portion of a patient's lower digestive system and the medical device may include distal components, such as a light and/or camera, adapted to facilitate examination of the physiological lumen.

Once inserted into the physiological lumen, at least a portion of the medical device is translated along the physiological lumen to an engagement location while the balloon is in the deflated state (operation 1804). For example, in certain implementations, the portion of the medical device may be a catheter including the balloon and translating the portion of the medical device may include extending the catheter and balloon along the physiological lumen while a second portion of the medical device (e.g., an endoscope body) remains at the initial insertion location. In another example implementation, translating the portion of the medical device may include moving an endoscope or similar portion of the medical device along a guide wire or catheter extending along the physiological lumen.

Following translation of the portion of the medical device, the balloon of the medical device is inflated such that protrusions of the balloon as described herein engage with the wall of the physiological lumen (operation 1806).

Once at least partially secured within the lumen, the medical device may be manipulated to perform various functions (operation 1808). In one example, the secured portion of the medical device may include a catheter and the medical device may be manipulated by translating an unsecured portion of the medical device along the physiological lumen using the secured catheter as a guide. In another implementation, the medical device may be manipulated to remove a foreign object or tissue from the physiological lumen. For example, manipulation of the medical device may include insertion and operation of one or more tools of the medical device configured to capture, excise, ablate, biopsy, or otherwise interact with tissue or objects within the physiological lumen. In one specific example, the balloon may be disposed distal a foreign object or tissue of interest within the lumen during operation 1804. The balloon may then be inflated in operation 1806 to obstruct the lumen. In one implementation, the balloon may then be moved proximally through the lumen to remove the foreign object. In another implementation, the balloon may instead be disposed within the lumen and moved distally to remove a foreign object distal the balloon. In another implementation, tools may be inserted through the medical device such that the tools may be used in a portion of the lumen proximal the inflated balloon. The foregoing examples may be useful for removing kidney stones from urinary ducts, removing gall stones from bile ducts, or clearing other foreign or undesirable matter present within the physiological lumen.

In another example medical procedure, a second balloon in accordance with the present disclosure may be disposed and inflated within the physiological lumen such that the protrusions of the second balloon partially engage the wall of the physiological lumen but otherwise remains at least partially movable within the physiological lumen. For example, the second balloon may be disposed on a guide wire or catheter that is then inserted through a medical device previously disposed within the physiological lumen (e.g., during operations 1804 and 1806). With the protrusions of the second balloon partially engaged, the second balloon may be translated along the physiological lumen to rub or scrape the wall of the physiological lumen.

Following manipulation of the medical device, the balloon is deflated to disengage the balloon from the physiological lumen (operation 1810) and an evaluation is conducted to determine when the medical procedure is complete (operation 1812). If so, the medical device is removed from the physiological lumen (operation 1814). Otherwise, the medical device may be repositioned within the physiological lumen for purposes of conducting any additional steps of the procedure (e.g., by repeating operations 1804-1812).

Figure 19:
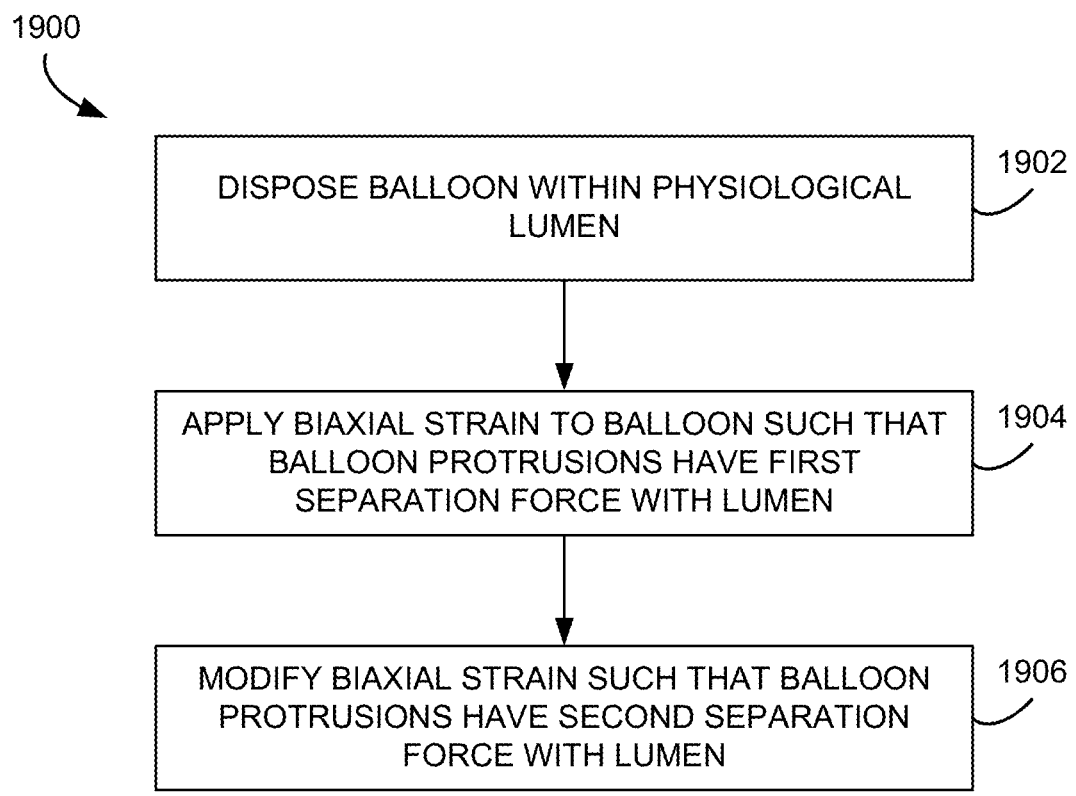
FIG. 19 is a flowchart illustrating a method of modifying engagement between a balloon in accordance with the present disclosure and a physiological lumen.

FIG. 19 is a second flowchart illustrating a method 1900 of modifying engagement between a balloon in accordance with the present disclosure and a physiological lumen. As previously discussed in the context of FIGS. 4A-7, the protrusions of balloons in accordance with the present disclosure may be configured to have adhesive and frictional properties that vary based on the biaxial strain applied to them. More specifically, applying strain to the balloon (e.g., by selectively inflating or deflating the balloon) causes deformation of the protrusions on the balloon's surface which in turn modifies adhesion and friction between the balloon and adjacent tissue. As previously discussed, by modifying the strain applied to the balloon, the adhesive and frictional properties may be dynamically manipulated by a physician to allow for improved control and flexibility during medical procedures.

With the foregoing in mind, the method 1900 begins with disposing a balloon having protrusions in accordance with the present disclosure within a physiological lumen (operation 1902). At operation 1904, a biaxial strain is applied to the balloon, such as by inflating the balloon, such that protrusions of the balloon interact with a wall of the physiological lumen and have a first separation force with the wall. At operation 1906 the biaxial strain is modified such that a second separation force different from the first separation force is achieved between the balloon and the wall of the physiological lumen.

With respect to the foregoing, modifying the biaxial strain in operation 1906 may include either of increasing or decreasing the biaxial strain on the balloon. Increasing the biaxial strain may include, for example, inflating the balloon beyond the extent to which the balloon was inflated during operation 1904. As discussed in the context of FIG. 7, increasing strain on the balloon in such a manner may generally result in an increase in the force required to separate the balloon from the wall of the physiological lumen (i.e., increase friction and/or adhesion). Decreasing the biaxial strain may include, for example, at least partially deflating the balloon to decrease the force required to separate the balloon from the wall of the physiological lumen (i.e., decrease friction and/or adhesion).

Figure 25A:
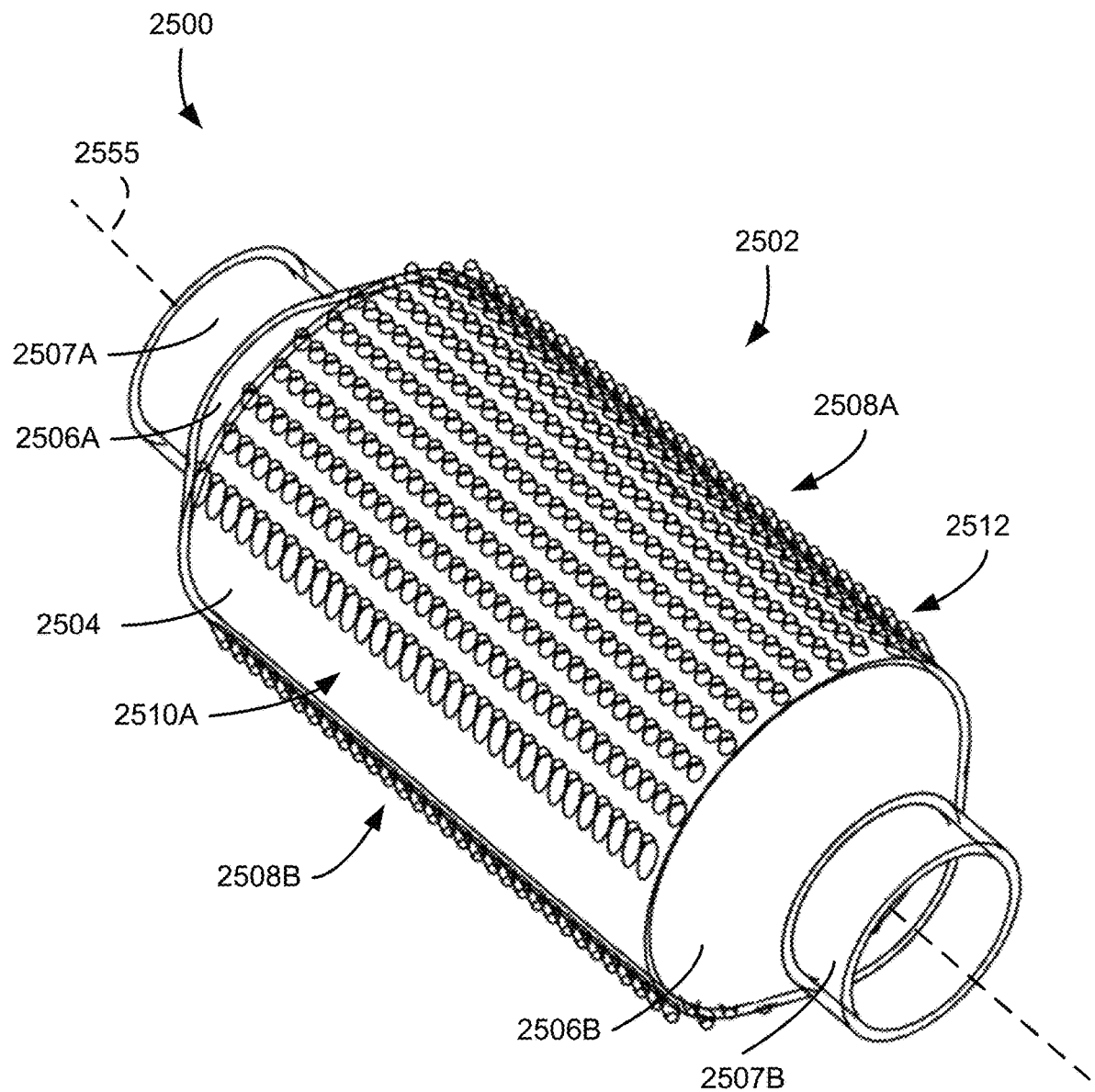
FIGS. 25A-25D are isometric, plan, end, and partial cross-sectional views of an example balloon having textured portions including transverse protrusions.
Figure 25B:
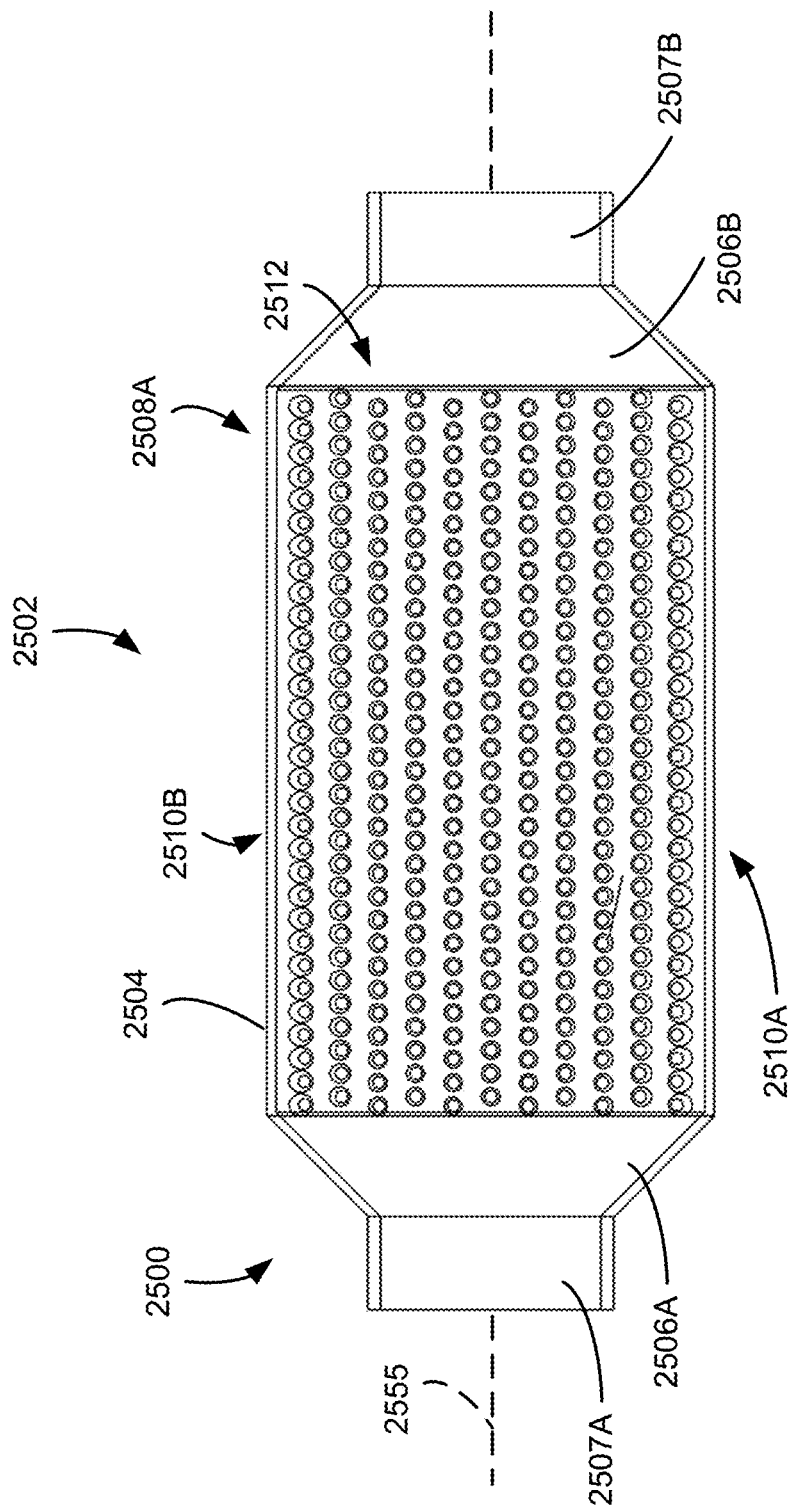
Figure 25C:
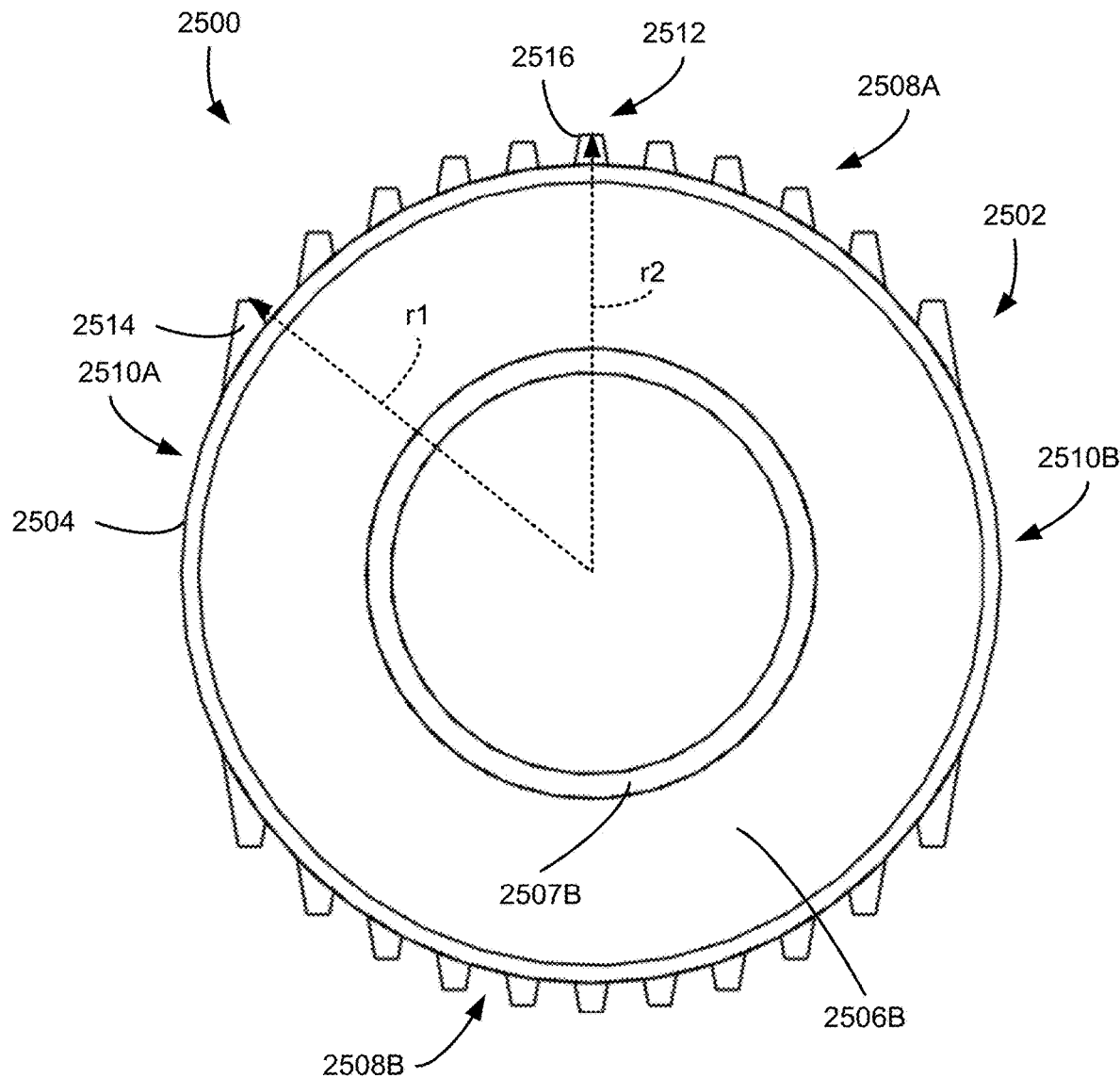

FIGS. 25A-25D illustrate one example implementation of a balloon 2500 in accordance with the present disclosure in an unstrained state. More specifically, FIG. 25A is an isometric view of the balloon 2500, FIG. 25B is a plan view of the balloon 2500, FIG. 25C is an end view of the balloon 2500, and 25D is a cross-sectional view of a textured surface of the balloon 2500.

Referring first to FIGS. 25A-25C, the balloon 2500 includes an elongate body 2502 extending along a longitudinal axis 2555. The elongate body 2502 generally includes a middle portion 2504 and tapering end portions 2506A, 2506B, each of which terminates in a respective annulus 2507A, 2507B. The middle portion 2504 of the balloon 2500 includes oppositely disposed textured portions 2508A, 2508B. Extending between the textured portions 2508A, 2508B are untextured portions 2510A, 2510B. In other implementations, the surface of the middle portion 2504 of the balloon 2500 may be divided into more than two textured portions and/or more than two untextured portions. Similarly, balloons in accordance with the present disclosure may include only one textured portion.

As best seen in FIG. 25B, the textured portions 2508A, 2508B of the balloon 2500 include uniformly distributed longitudinal rows of protrusions (e.g. protrusions rows 2512). As discussed below in further detail, the protrusions of the balloon 2500 have a truncated cone shape, although other protrusion shapes may be used in other implementations. Also, as visible in FIG. 25B, adjacent rows of protrusions of the balloon 2500 are offset relative to each other such that every other row is aligned. In other implementations other row configurations may be implemented. For example, all rows may be aligned or multiple offsets may be used between different pairs of rows.

In at least certain implementations, the frictional and adhesive properties of the protrusions within a given row may vary based on the longitudinal spacing between the protrusions. For example, if spacing between protrusions is relatively narrow (e.g., from around 25 µm to around 400 µm, or from around 5% to 50% of the width of the protrusions), traction in a collapsed or unstrained state is generally reduced as compared to implementations including wider spacing. Testing suggest that such variable traction is the result of narrowly spaced protrusions in a given row more closely approximating the drag and traction provided by a continuous structure (e.g., a rib) as opposed to a series of independent protrusions. For example, during certain tests, it was observed that when in a partially deflated state, traction for a given balloon having twenty rows of approximately forty protrusions each approximated the traction provided by twenty continuous ribs extending along the length of the balloon. However, as the spacing between the protrusions was increased (e.g., by inflating and expanding the balloon) traction was observed to increase significantly. Among other things, the increase in traction was attributable to substantially all of the leading edges of the 400 protrusions being exposed and able to fully engage and interact with the inner wall of the physiological lumen when in the expanded state as compared to when the protrusions were more closely spaced.

The protrusions are configured such that when in a partially inflated state, each protrusion of each respective textured portion 2508A, 2508B extends in a common transverse direction relative to the longitudinal axis. In other words, the protrusions of the textured portion 2508A extend parallel to each other in a first transverse direction while the protrusions of the textured portion 2508B extend parallel to each other in a second transverse direction that is opposite the first lateral direction. In other implementations, the textured portions 2508A, 2508B may not be oppositely disposed but nevertheless including protrusions that extend in respective transverse directions.

As shown in FIG. 25C, the textured portions 2508A, 2508B and the untextured portions 2510A, 2510B collectively extend around the circumference of the middle portion 2504 of the balloon 2500. In the particular example illustrated in FIG. 25C, each textured portion 2508A, 2508B extends around about a third of the surface of the middle portion 2504, while the remaining third of the surface is divided between the untextured portions 2510A, 2510B. It should be appreciated, however, that the distribution of the textured and untextured portions of the balloon 2500 may vary from that which is illustrated in FIGS. 25A-D.

As previously noted, each of the tapering end portions 2506A, 2506B terminate in a respective annulus 2507A, 2507B. In general, each annulus 2507A, 2507B is sized and shaped to be fit onto an overtube, catheter, endoscope, or similar tool. Accordingly, the shape and dimensions of each annulus 2507A, 2507B may vary depending on the specific tool onto which the balloon 2500 is to be disposed. However, in at least certain implementations, each annulus 2507A, 2507B may be reinforced relative to other portions of the balloon 2500 that are intended to expand. For example, in certain implementation, the wall thickness of each annulus 2507A, 2507B may be from and including about 1.25 times to and including about 5 times thicker than the wall thickness of the rest of the balloon 2550. Among other things, thickening each annulus 2507A, 2507B facilitates improved retention of the balloon 2500 on an overtube or other tool, particularly when the balloon 2500 is subjected to inflation and deflation.

As illustrated in FIG. 25C, in at least certain implementations, the height of each protrusion may be defined such that each protrusion extends to a common radius. For example, protrusion 2514 has a height such that a center of the tip of the protrusion 2514 extends to a radius r1 while protrusion 2516 has a height such that a center of the tip of the protrusion 2516 extends to a radius r2 that is substantially the same as the radius r1 of protrusion 2514. An alternative interpretation of this approach to determining protrusion heights is that each protrusion extends from the surface of the balloon 2500 such that the midpoint of a top surface of each protrusion lies on a common circle.

Figure 25D:
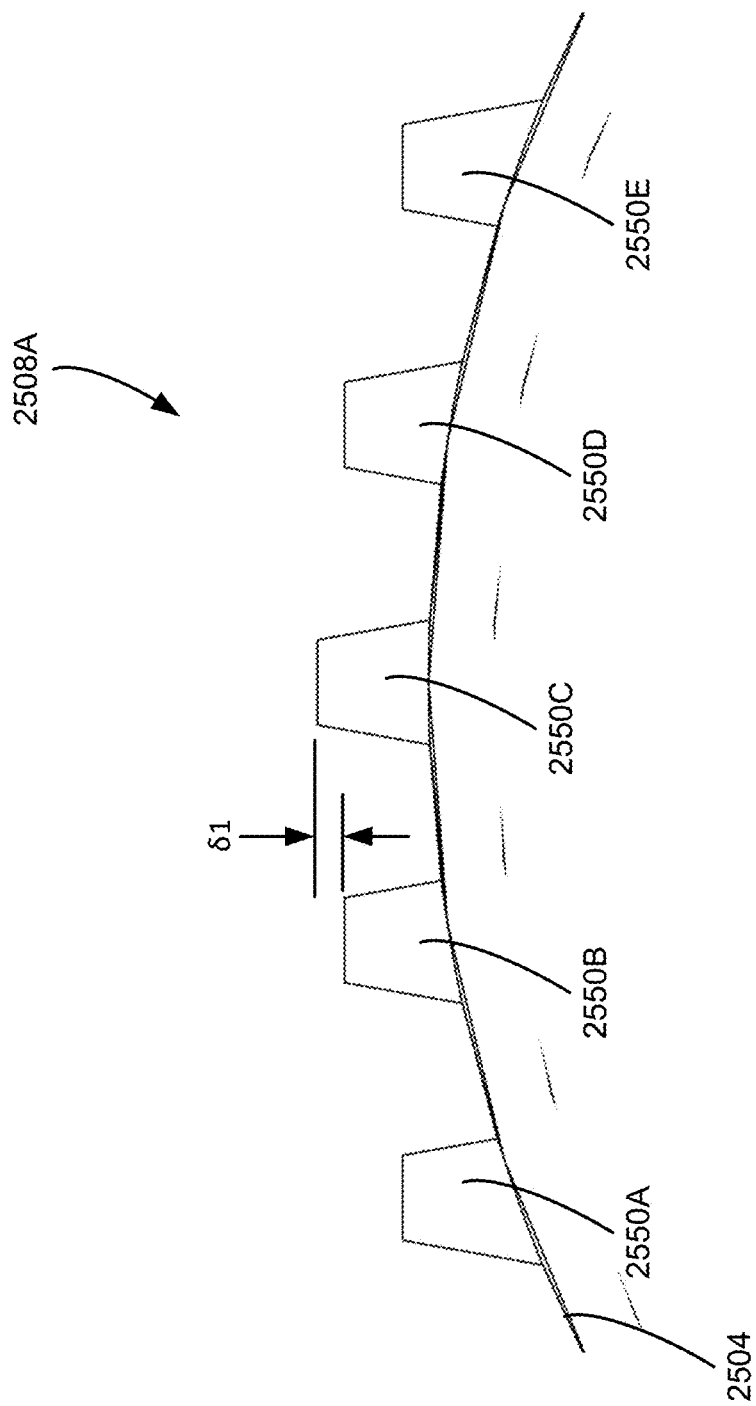

Referring now to FIG. 25D, a partial cross-sectional view of the middle portion 2504 of the balloon 2500 is provided to illustrate further details of the protrusions of the textured portions 2508A, 2508B. In the particular illustrated design, each protrusion (e.g. protrusions 2550A-E) of the balloon 2500 has a truncated conical shape. While illustrated as having flat tops, in at least certain implementations, the top surface of each protrusion may instead be concave, as previously discussed herein.

FIG. 25D illustrates an alternative approach to selecting the height of each protrusion. More specifically, in at least certain implementations, the height of protrusions in each row may be selected such that there is a predetermined height difference between adjacent rows. For example, FIG. 25D includes a dimension δ1 corresponding to the difference in height between adjacent rows. As illustrated, δ1 may be maintained between successive pairs of adjacent rows such that the top surfaces of the protrusions in adjacent rows descend in a step-like manner. Alternatively, δ1 may differ between adjacent rows. Although various values of δ1 may be used in implementations of the present disclosure, in at least certain implementations δ1 may be from and including about 5 μm to and including about 3 mm. The foregoing approach may be used as an alternative to the previously discussed approach in which each protrusion extends such that a midpoint of its tip is at a common radius or lies on a common circle.

Although the specific dimensions of the balloon 2500 may vary based on the particular application of the balloon 2500, in at least certain implementations, the balloon 2500 may have an overall length from and including about 10 mm to and including about 100 mm. In such implementations, the middle portion 2504 of the balloon may be from and including about 5 mm to and including about 90 mm and the end portions 2506A, 2506B may each be from and including about 2 mm to and including about 10 mm. The middle portion 2504 may also have a resting/partially inflated diameter from and including about 2 mm to and including about 50 mm, with the diameter corresponding to the surface of the middle portion 2504 from which the protrusions extend. The middle portion 2504 may also have a wall thickness from and including about 100 μm to and including about 3000 μm. Further in such implementations, each annulus 2507A, 2507B may have an outer diameter from and including 1 mm to and including 20 mm and a wall thickness from and including 100 μm to and including 5000 μm. The foregoing dimensions should be understood to be merely examples and designs in which the foregoing dimensions fall below or exceed the specified ranges should still be regarded as being within the scope of this disclosure.

Referring next to FIGS. 26A-26D, a second balloon 2600 in an unstrained state is provided. Similar to the previously disclosed balloon 2500, the balloon 2600 includes an elongate body 2602 extending along a longitudinal axis 2650, the elongate body including a middle portion 2604 and tapering end portions 2606A, 2606B. Each of the end portions 2606A, 2606B similarly terminates in a respective annulus 2607A, 2607B for coupling the balloon 2600 to an overtube or similar tool. The middle portion 2604 of the balloon 2600 also includes oppositely disposed textured portions 2608A, 2608B and untextured portions 2610A, 2610B extending therebetween.

Figure 26A:
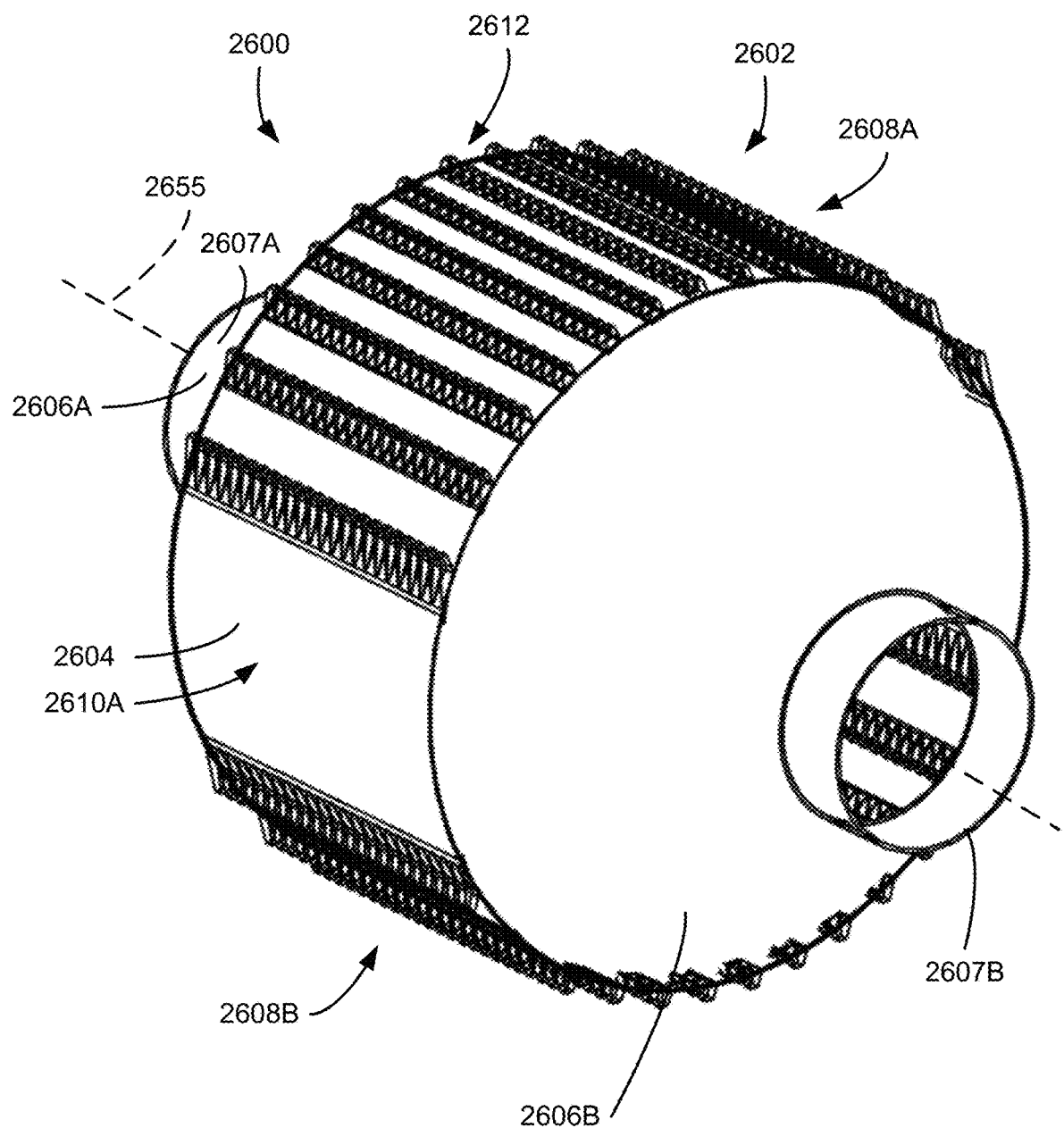
FIGS. 26A-26D are isometric, plan, end, and partial cross-sectional views of another example balloon having textured portions including transverse protrusions.
Figure 26B:
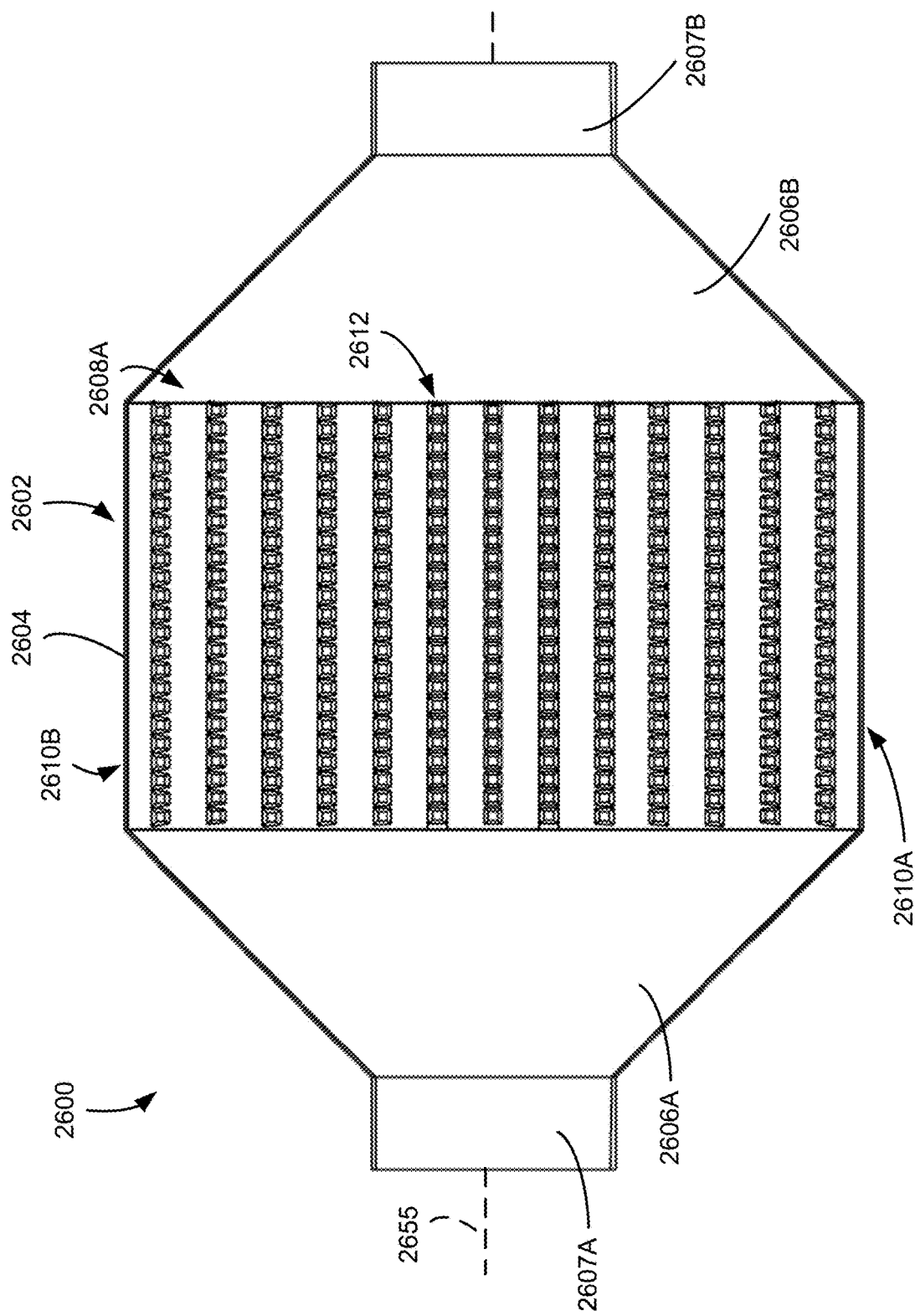
Figure 26C:
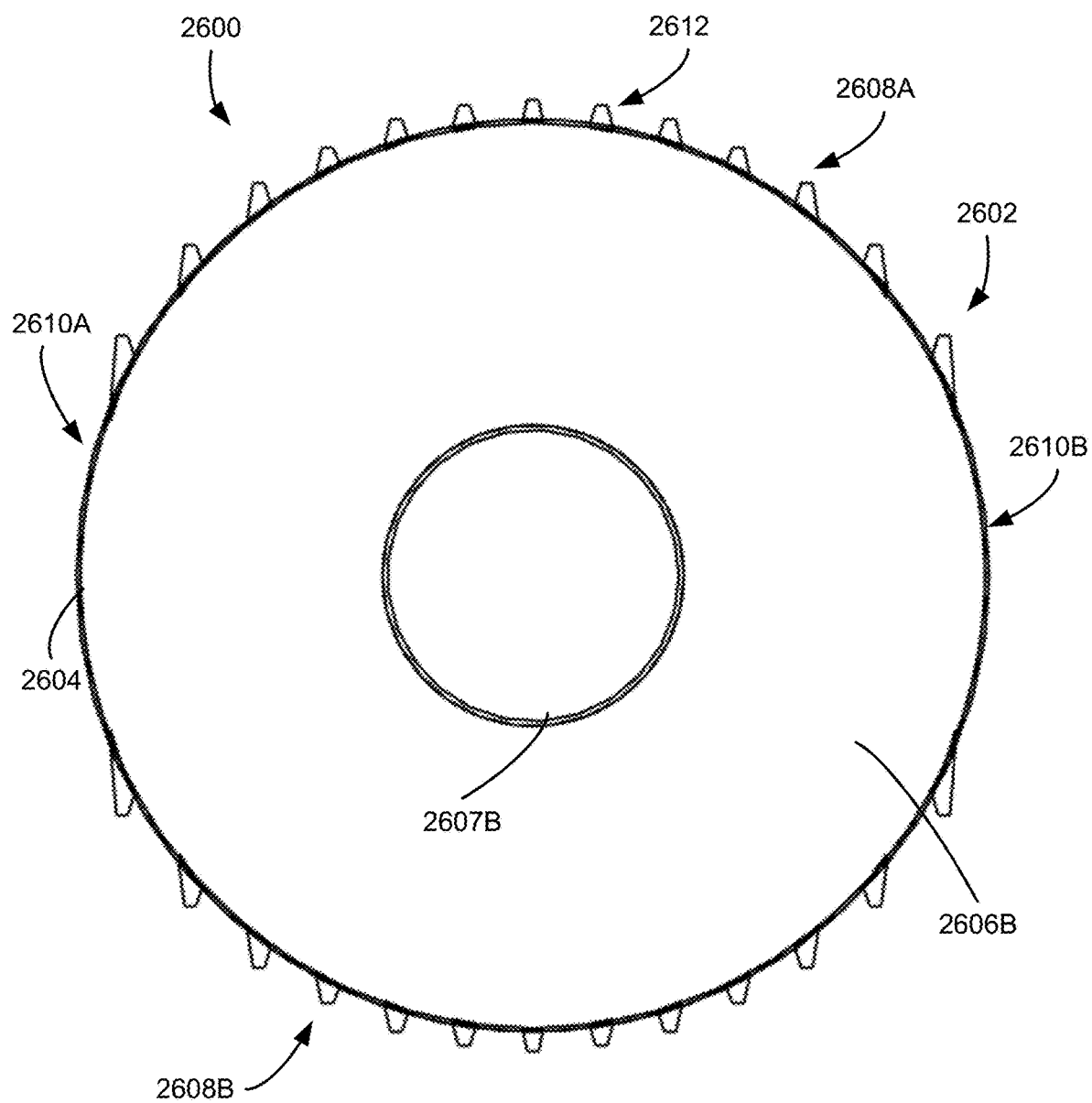

As best seen in FIG. 26B, the textured portions 2608A, 2608B of the balloon 2600 include uniformly distributed rows of protrusions 2612. In contrast to the truncated cone protrusions of the balloon 2500 discussed above, the protrusions of the balloon 2600 have a truncated pyramidal shape. Also, as shown in FIG. 26B, adjacent rows of protrusions of the balloon 2600 are aligned relative to each other, as compared to the offset configuration of the balloon 2500 and adjacent protrusions within a given row of the balloon 2600 are sized and shaped such that they contact each other. This in contrast to the rows of the balloon 2500 in which adjacent protrusions in a row were spaced apart.

Like those of the balloon 2500, the protrusions 2612 of the balloon 2600 are configured such that when in a partially inflated state, each protrusion of each respective textured portion 2608A, 2508B extends in a lateral direction relative to the longitudinal axis. In other words, the protrusions of the textured portion 2608A extend in a first lateral direction while the protrusions of the textured portion 2608B extend in a second lateral direction that is opposite the first lateral direction.

Figure 26D:
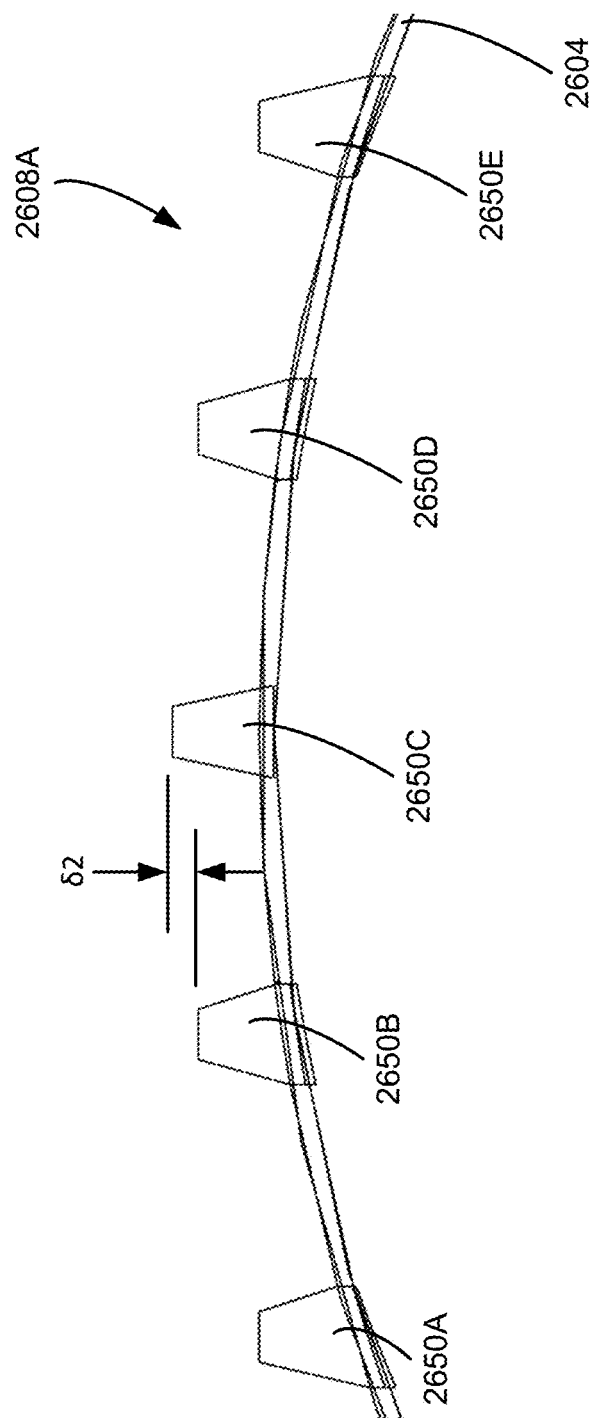

Referring now to FIG. 26D, a partial cross-sectional view of the middle portion 2604 of the balloon 2600 is provided to illustrate further details of the protrusions of the textured portions 2608A, 2608B (e.g., protrusions 2650A-E). As previously noted the protrusions 2650A-E have a truncated square-based pyramid shape having a flat top. Nevertheless, the top surface of each protrusion may instead be concave, as previously discussed herein. Like the protrusions of the balloon 2500, adjacent rows of the protrusions of the balloon 2600 may be configured such that the change in height (indicated as δ2) between adjacent rows of protrusions may be from and including about 5 µm to and including about 3 mm. Alternatively, and as described above in the context of FIG. 25C, each protrusion may have a height such that a midpoint of a tip of each protrusion extends to a common radius/lies on a common circle.

Although the specific dimensions of the balloon 2600 may vary based on the particular application of the balloon 2600, in at least certain implementations, the balloon 2600 may have an overall length from and including about 10 mm to and including about 100 mm. In such implementations, the middle portion 2604 of the balloon may be from and including about 5 mm to and including about 90 mm and the end portions 2606A, 2606B may each be from and including about 2 mm to and including about 10 mm. The middle portion 2604 may also have a resting/partially inflated diameter from and including about 2 mm to and including about 50 mm, with the diameter corresponding to the surface of the middle portion 2604 from which the protrusions extend. The middle portion 2604 may also have a wall thickness from and including about 100 µm to and including about 3000 µm. Further in such implementations, each annulus 2607A, 2607B may have an outer diameter from and including 1 mm to and including 20 mm and a wall thickness from and including 100 µm to and including 5000 µm. The foregoing dimensions should be understood to be merely examples and designs in which the foregoing dimensions fall below or exceed the specified ranges should still be regarded as being within the scope of this disclosure.

Referring next to FIGS. 27A-27D, a third balloon 2700 in an unstrained state is provided. Similar to the previously disclosed balloons, the balloon 2700 includes an elongate body 2702 extending along a longitudinal axis 2750, the elongate body including a middle portion 2704 and tapering end portions 2706A, 2706B. Each of the end portions 2706A, 2706B terminates in a respective annulus 2707A, 2707B for coupling the balloon 2700 to an overtube or similar tool. The middle portion 2704 of the balloon 2700 includes oppositely disposed textured portions 2708A, 2708B and untextured portions 2710A, 2710B extending therebetween.

The textured portions 2708A, 2708B of the balloon 2700 include uniformly distributed rows of protrusions 2712 and, more specifically, pyramidal protrusions. Similar to the rows of protrusions of the balloon 2600, the rows of protrusions 2712 of the balloon 2700 are aligned relative to each other and adjacent protrusions within a given row of the balloon 2700 are sized and shaped such that they contact each other. However, in contrast to the previous two example balloons 2500, 2600, the protrusions 2712 of the balloon 2700 are configured such that when in a partially inflated state, each protrusion of each respective textured portion 2708A, 2708B extends radially.

Figure 27A:
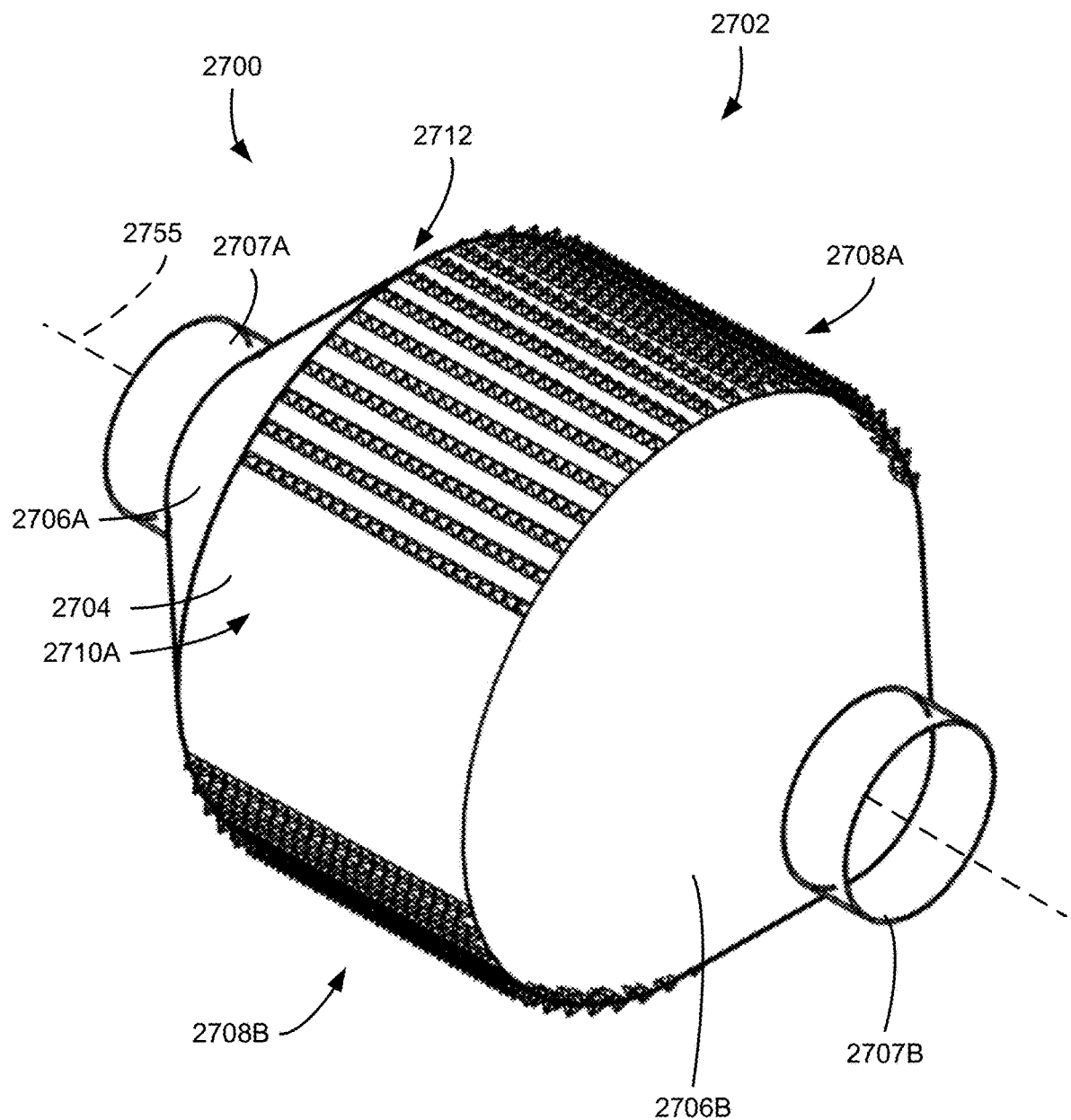
FIGS. 27A-27D are isometric, plan, end, and partial cross-sectional views of an example balloon having texturing portions including radial protrusions.
Figure 27B:
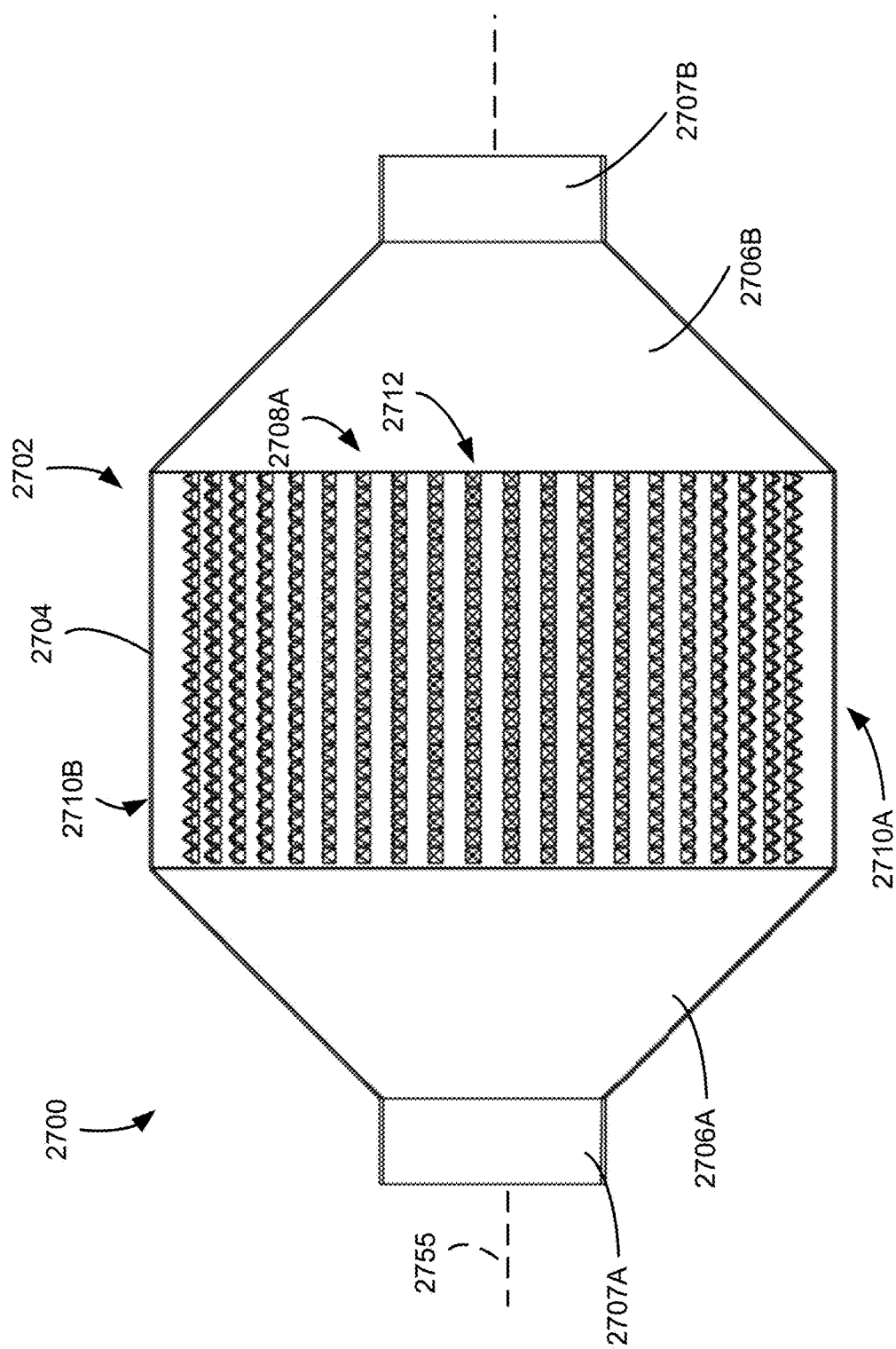
Figure 27C:
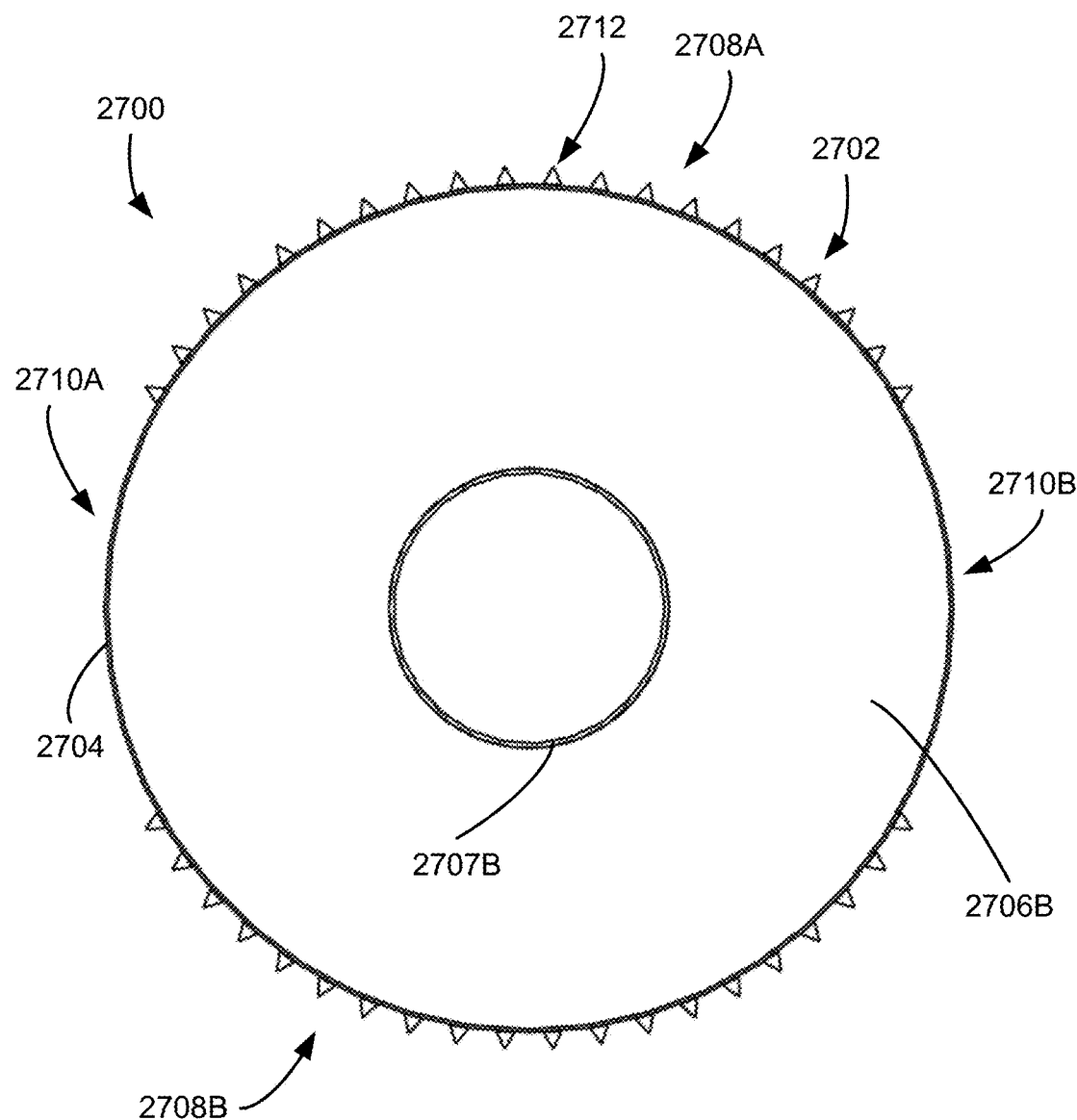
Figure 27D:
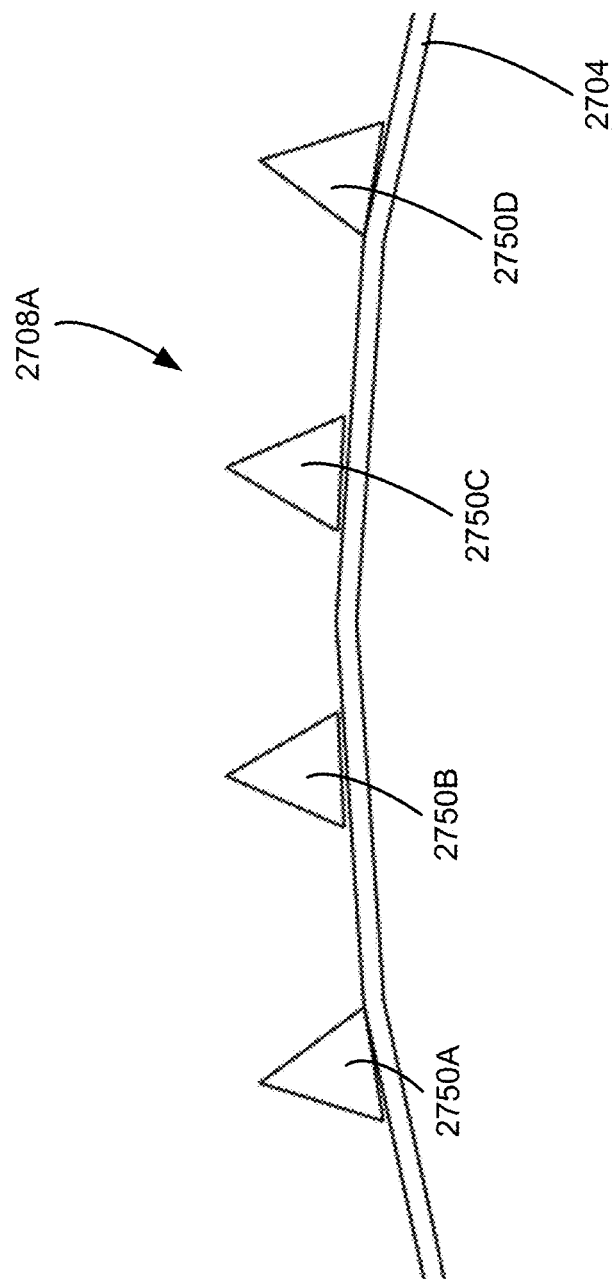

Referring now to FIG. 27D, a partial cross-sectional view of the middle portion 2704 of the balloon 2700 is provided to illustrate further details of the protrusions of the textured portions 2708A, 2708B. As previously noted the protrusions (e.g., protrusions 2750A-D) have a pyramidal shape; however, the pyramidal shaped protrusions may have any other suitable shape discussed herein, including shapes having concave top surfaces.

Although the specific dimensions of the balloon 2700 may vary based on the particular application of the balloon 2700, in at least certain implementations, the balloon 2700 may have an overall length from and including about 10 mm to and including about 100 mm. In such implementations, the middle portion 2704 of the balloon may be from and including about 5 mm to and including about 90 mm and the end portions 2706A, 2706B may each be from and including about 2 mm to and including about 10 mm. The middle portion 2704 may also have a resting/partially inflated diameter from and including about 2 mm to and including about 50 mm, with the diameter corresponding to the surface of the middle portion 2704 from which the protrusions extend. The middle portion 2704 may also have a wall thickness from and including about 100 µm to and including about 3000 µm. Further in such implementations, each annulus 2707A, 2707B may have an outer diameter from and including 1 mm to and including 20 mm and a wall thickness from and including 100 µm to and including 5000 µm. The foregoing dimensions should be understood to be merely examples and designs in which the foregoing dimensions fall below or exceed the specified ranges should still be regarded as being within the scope of this disclosure.

Figure 28A:
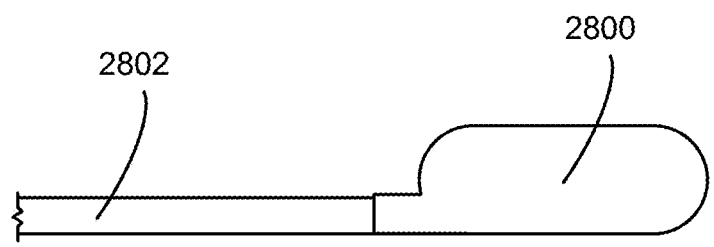
FIGS. 28A and 28B are schematic illustrations of a first directional balloon in a collapsed state and an at least partially inflated state, respectively.
Figure 28B:
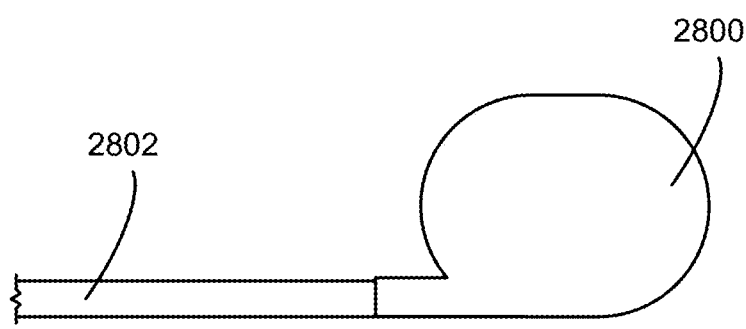

Previous implementations discussed herein generally include balloons that are mounted coaxially with an overtube or similar medical tool and expand in a substantially uniform, radial direction about the tube. Nevertheless, it should be appreciated that in at least certain implementations, such balloons may instead be configured to expand directionally. For example, 28A and 28B illustrates a first example balloon 2800 eccentrically mounted to an overtube 2802. Accordingly, as the balloon 2800 is inflated and expands (as illustrated in the transition from FIG. 28A to 28B), the balloon 2800 is biased to one side of the overtube 2802.

Figure 29A:
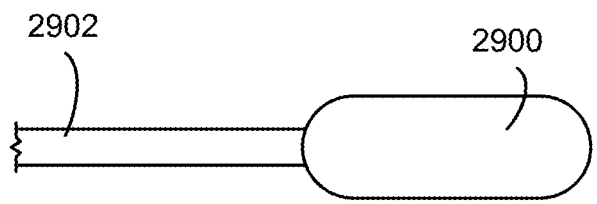
FIGS. 29A and 29B are schematic illustrations of a second directional balloon in a collapsed state and an at least partially inflated state, respectively.
Figure 29B:
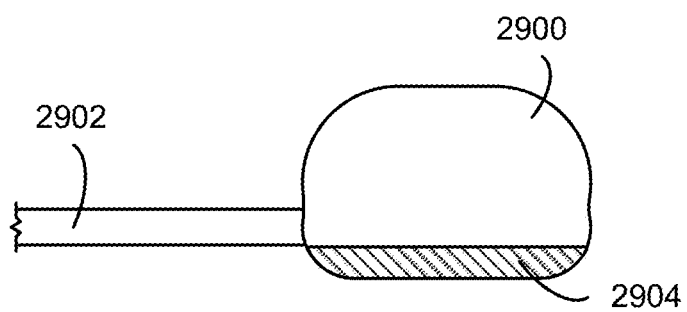

FIGS. 29A and 29B illustrate an alternative implementation in which a balloon 2900 is configured to expand directionally from an overtube 2902 or similar tool on which the balloon 2900 is mounted. Such directional expansion may be achieved, for example, by forming the balloon to have a localized region or side (indicated by hashed area 2904) having increased stiffness or rigidity as compared to other portions of the balloon 2900. Such reinforcement may be achieved, for example, by increasing the wall thickness of the balloon 2900 in the region having reduced expansion; using a stiffer material in the region having reduced expansion; including internal or external ribs, bands, or similar reinforcing structures in the area having reduced expansion; or using any other suitable technique for locally increasing stiffness.

Figure 30A:
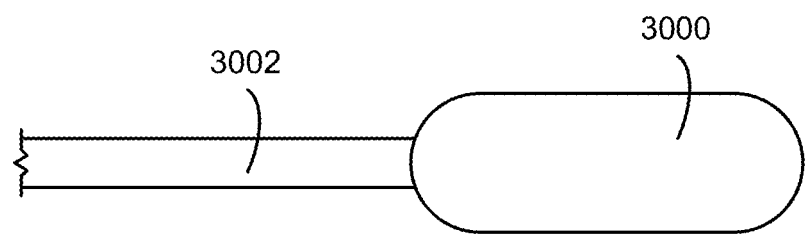
FIGS. 30A and 30B are schematic illustrations of a balloon having non-uniform inflation in a collapsed state and an at least partially inflated state, respectively.
Figure 30B:
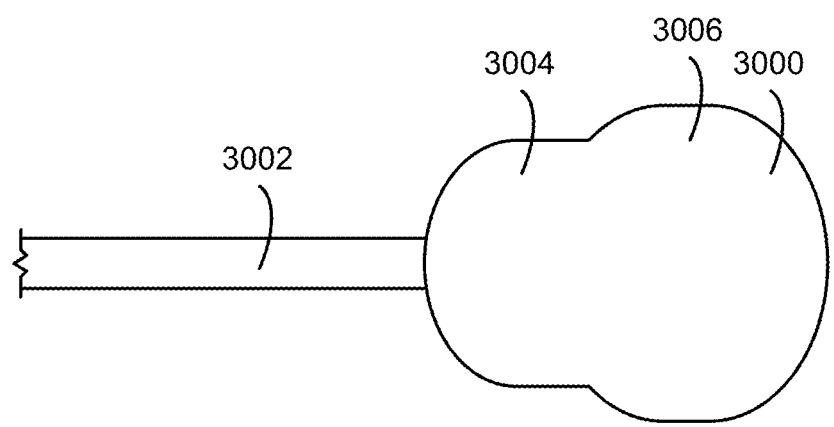

In addition to directional expansion, balloons in accordance with the present disclosure may have variable expansion along their length. For example FIGS. 30A and 30B are schematic illustrations of a balloon 3000 disposed on an overtube 3002 or similar tool. As illustrated in the transition between FIGS. 30A and 30B, when inflated, a proximal portion of the balloon 3004 expands to a lesser extent than a distal portion of the balloon 3006. Similar to the balloon 2900 of FIGS. 29A and 29B, such variable expansion may be achieved by varying material, wall thickness, and reinforcement along the length of the balloon 3000.

Figure 31:
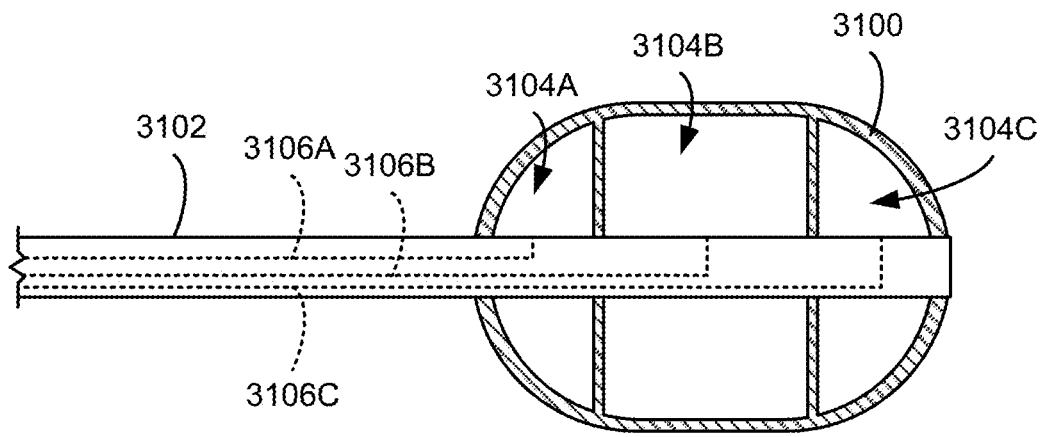
FIG. 31 is a cross-sectional view of a balloon including multiple and independently inflatable internal chambers.

In addition to or as an alternative to selectively reinforcing sections of a balloon to provide variable expansion, balloons in accordance with the present disclosure may include distinct and selectively expandable compartments. For example, FIG. 31 illustrates an example balloon 3100 disposed on an overtube 3102 or similar tool and defining three distinct and isolated internal compartments 3104A-3104C. Each compartment 3104A-3104C is connected to an independently controlled air line 3106A-3106C such that air may be selectively supplied and removed from each of the compartments 3104A-3104C to selectively control their respective expansion and deflation.

Figure 32:
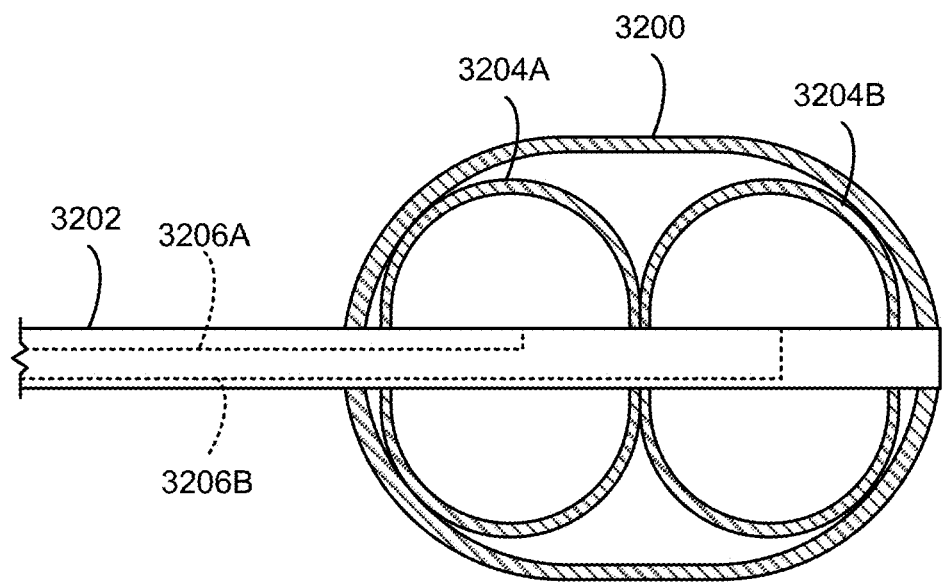
FIG. 32 is a cross-sectional view of a balloon including an outer sheath/balloon and independently inflatable internal balloons disposed within the outer sheath/balloon.

FIG. 32 illustrates an alternative approach to providing a balloon having variably expandable regions. More specifically, FIG. 32 illustrates a sheath or outer balloon 3200 within which multiple and independently inflatable internal balloons 3204A, 3204B may be disposed. Each of the balloons 3200, 3204A, and 3204B may in turn be coupled to an overtube 3202 or similar tool. In such implementations, the outer balloon 3202 may include texturing or protrusions, as described herein, while the internal balloons may be substantially smooth. Similar to the compartmentalized balloon 3100 of FIG. 31, each internal balloon 3204A, 3204B may be in communication with a respective and independently controlled air line 3106A, 3106B to selectively control inflation and deflation of the internal balloons and, as a result, the overall shape of the outer balloon 3202.

Figure 33:
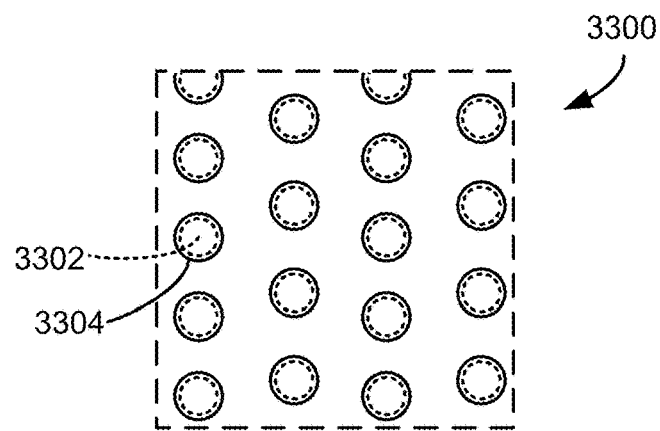
FIGS. 33-35 illustrate various implementations of protrusion reinforcement on internal surfaces of balloons in accordance with the present disclosure.
Figure 34:
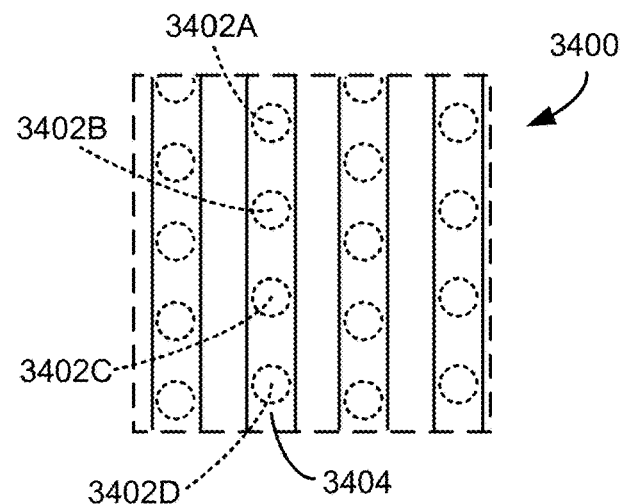
Figure 35:
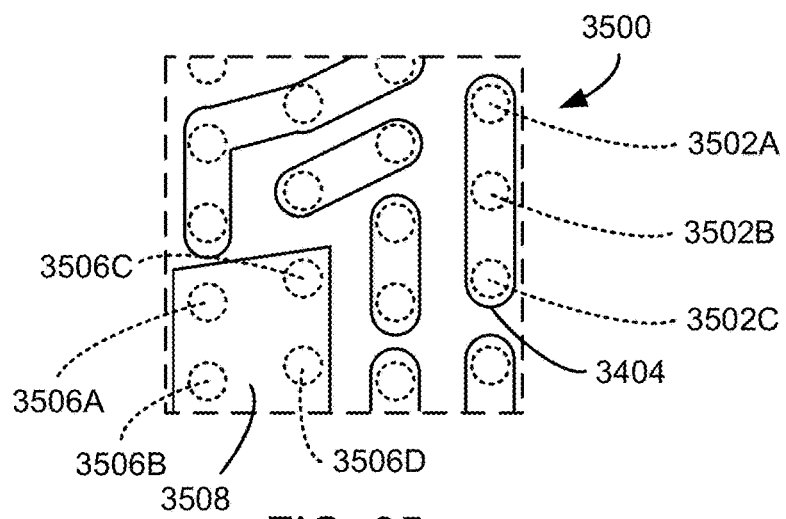

In certain implementations of the present disclosure, protrusions extending from the balloon may be reinforced to increase overall rigidity of the protrusions, thereby preventing or reduce bending or other deformation during transportation of the balloon within a physiological lumen or following anchoring of the balloon within the lumen. In certain implementations, such reinforcement of the protrusions may be provided on the internal surface of the balloon. For example, FIGS. 33-35 each illustrate non-limiting examples of internal reinforcement that may be applied to the protrusions. FIG. 33, for example, illustrates a portion 3300 of an example inner balloon surface in which each protrusion (e.g., protrusion 3302) is individually reinforced by a corresponding bump (e.g., bump 3304 corresponding to protrusion 3302) or similar localized thickening of the balloon wall opposite the protrusion. As another example, FIG. 34 illustrates a portion 3400 of another example inner balloon surface in which multiple protrusions (e.g., protrusions 3402A-3402D) are linked by a corresponding ridge, rib, or similar reinforcing structure (e.g., rib 3404) extending along the inner surface of the balloon. FIG. 35 illustrates another portion 3500 of an example inner balloon surface illustrating that such reinforcement may be non-uniform. For example, while protrusions 3502A-3502C are reinforced using a common and straight rib 3504, protrusions 3506A-3406D are reinforced by a patch 2508 of balloon material.

Figure 36:
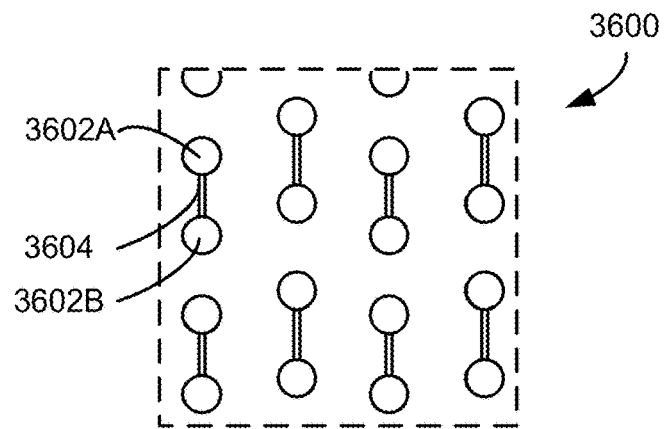
FIGS. 36-38 illustrate various implementations of protrusion reinforcement on external surfaces of balloons in accordance with the present disclosure.
Figure 37:
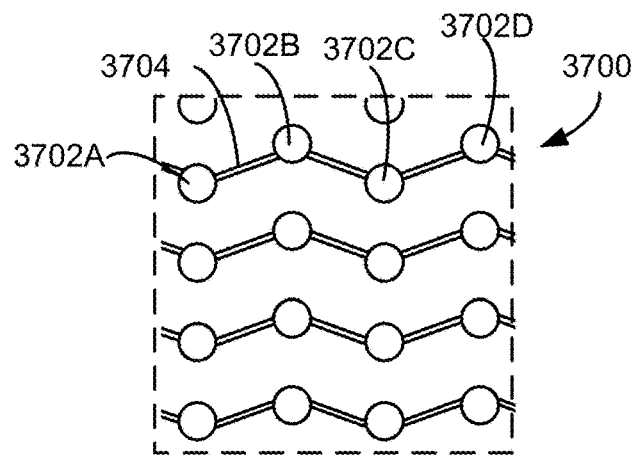
Figure 38:
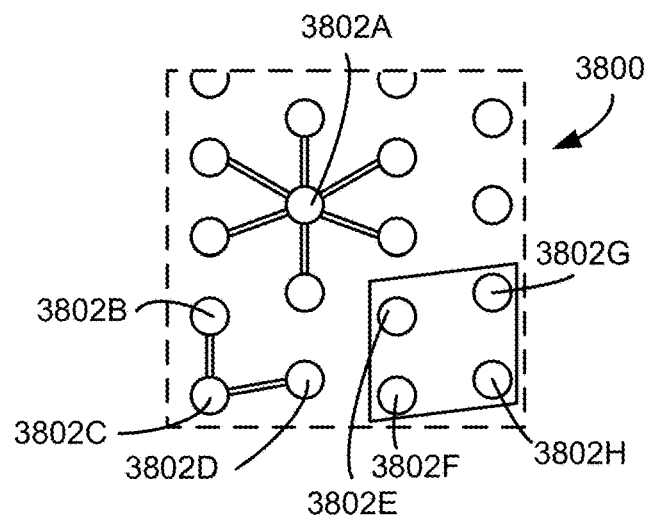

Reinforcement of the protrusions may also be achieved by linking or connecting protrusions on the exterior surface of the balloon. For example, FIG. 36 illustrates a portion 3600 of an external surface of a first example balloon in which adjacent protrusions (e.g., protrusions 3602A, 3602B) are linked or otherwise mutually reinforced by a rib 3604 extending therebetween. FIG. 37 illustrates a portion 3700 of a second example balloon in which protrusions (e.g., protrusions 3702A-3702D) are linked by continuous ribs (e.g., rib 3704). Finally, FIG. 38 illustrates a portion 3800 of a third example balloon having non-uniform protrusion reinforcement. For example, protrusion 3802A is coupled to and reinforced by each of its nearest neighboring protrusions, protrusions 3802-3802D are reinforced to form an "L" shaped pattern, and protrusions 3802E-3802 are reinforced by a patch 3804 or pad extending therebetween.

The foregoing examples of internal and external protrusion reinforcement are intended merely as non-limiting examples. More generally, reinforcement of protrusions in accordance with the present disclosure may be achieved by either or both of providing additional material on the inner surface of the balloon opposite the protrusions, providing additional material on the external surface of the balloon adjacent the protrusions, or forming a mechanical link between protrusions, such as by forming a rib or similar structure extending between protrusions.

The foregoing balloon designs are intended merely as examples and are not intended to limit the scope of the present disclosure. Rather, features of any balloon disclosed herein may be combined in any suitable manner. For example, any size, shape, and arrangement of protrusions may be implemented with any corresponding balloon shape or size. Similarly, other features, such as those related to controlled collapse, may be incorporated into any balloon design disclosure herein. Similarly, any specific dimensions or proportions provided in the context of specific balloon designs are intended merely as examples and should not be construed as limiting. More generally, any particular implementations of balloons discussed or illustrated herein should be regarded as one possible combination of features of balloons in accordance with the present disclosure.

The present disclosure is further directed to kits including medical devices in accordance with the present disclosure. In certain implementations, the kit includes an endoscope or similar medical device including at least one inflatable balloon having protrusions as described herein. In other implementations, the kit further includes a catheter including a balloon having protrusions as described herein. In yet other implementations, the kit includes instructional materials detailing methods of using medical devices in accordance with the present disclosure. In still another implementation, the kit includes each of an endoscope and a catheter, each of which includes a balloon as described herein. In still other implementations, the kit includes instructional materials detailing methods of using the endoscope and the catheter.

As used herein, each of the following terms has the meaning associated with it in this section.

As used herein, unless defined otherwise, all technical and scientific terms generally have the same meaning as commonly understood by one of ordinary skill in the art to which this disclosure belongs. Generally, the nomenclature used herein is those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "instructional material" includes a publication, a recording, a diagram, or any other medium of expression that may be used to communicate the usefulness of the compositions and/or methods of the present disclosure. The instructional material of the kit may, for example, be affixed to a container that contains the compositions of the present disclosure or be shipped together with a container that contains the compositions. Alternatively, the instructional material may be shipped separately from the container with the intention that the recipient uses the instructional material and the compositions cooperatively. For example, the instructional material is for use of a kit; and/or instructions for use of the compositions.

Throughout this disclosure, various aspects of the present disclosure may be presented in a range format. It should be understood that the description in range format is merely for convenience and brevity and should not be construed as an inflexible limitation on the scope of the present disclosure. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Every formulation or combination of components described or exemplified can be used to practice implementations of the current disclosure, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

Although the description herein contains many example implementations, these should not be construed as limiting the scope of the current disclosure but as merely providing illustrative examples.

All references throughout this disclosure (for example, patent documents including issued or granted patents or equivalents; patent application publications; and non-patent literature documents or other source material) are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. In general the terms and phrases used herein have their art-recognized meaning, which can be found by reference to standard texts, journal references, and contexts known to those skilled in the art. Any preceding definitions are provided to clarify their specific use in the context of the present disclosure.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present disclosure.

The disclosures of each and every patent, patent application, and publication cited herein are hereby incorporated herein by reference in their entirety.

While this disclosure includes reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A medical device configured to be inserted into a physiological lumen of a patient, the medical device comprising:
    an elongate body;
    an inflatable balloon defining a longitudinal axis, the inflatable balloon attached to and partially surrounding at least a section of the elongate body; and
    a first longitudinal row of protrusions and a second longitudinal row of protrusions, the second longitudinal row of protrusions being circumferentially adjacent to the first longitudinal row, the protrusions of the first longitudinal row and the second longitudinal row extending from an outer surface of the inflatable balloon,
    wherein, when the inflatable balloon is in an unstrained state, a plane defining a top surface of a first protrusion of the first longitudinal row is parallel to a plane defining a top surface of a second protrusion of the second longitudinal row.

2. The medical device of claim 1, wherein the inflatable balloon comprises at least one material selected from the group consisting of low-density polyethylene, latex, polyether block amide, silicone, poly-siloxane, polyethylene terephthalate, nylon, and polyurethane.

3. The medical device of claim 1, wherein each of the protrusion of the first longitudinal row and the protrusion of the second longitudinal row has a height from and including about 50 µm to and including about 5000 µm tall.

4. The medical device of claim 1, wherein each of the protrusion of the first longitudinal row and the protrusion of the second longitudinal row has a frustoconical shape.

5. The medical device of claim 1, wherein each of the protrusion of the first longitudinal row and the protrusion of the second longitudinal row has a pyramidal shape.

6. The medical device of claim 5, wherein the pyramidal shape is a flat-topped pyramidal shape.

7. The medical device of claim 1, wherein each of the protrusion of the first longitudinal row and the protrusion of the second longitudinal row has a side surface and an edge formed between the top surface and the side surface, the edge having a radius from and including 5 µm to and including 500 µm.

8. The medical device of claim 1, further comprising a third protrusion of a third longitudinal row and a fourth protrusion of a fourth longitudinal row extending from the outer surface of the balloon in a direction different than that of the first protrusion of the first longitudinal row and the second protrusion of the second longitudinal row, wherein, when the inflatable balloon is in the unstrained state, a plane defining a top surface of the third protrusion of the third longitudinal row is parallel to a plane defining a top surface of the fourth protrusion of the fourth longitudinal row.

9. The medical device of claim 1, wherein, when the inflatable balloon is in the unstrained state, the top surface of the protrusion of the first longitudinal row and the top surface of the protrusion of the second longitudinal row are concave.

10. The medical device of claim 1, wherein the inflatable balloon comprises an untextured proximal end and an untextured distal end and each of the protrusion of the first longitudinal row and the protrusion of the second longitudinal row is disposed between the untextured proximal end and the untextured distal end.

11. The medical device of claim 1, wherein, when in a collapsed state, an untextured portion of the inflatable balloon extends to a radius and each of the protrusion of the first longitudinal row and the protrusion of the second longitudinal row does not extend beyond the radius.

12. The medical device of claim 1, wherein each of the protrusion of the first longitudinal row and the protrusion of the second longitudinal row has a width and the first longitudinal row and the second longitudinal row have a separation that is from and including 5% of the width to and including 50% of the width.

13. The medical device of claim 1, wherein, when the inflatable balloon is in the unstrained state, the top surface of the protrusion of the first longitudinal row and the top surface of the protrusion of the second longitudinal row are flat.

14. A medical device configured to be inserted into a physiological lumen of a patient, the medical device comprising:
an elongate body;
an inflatable balloon defining a longitudinal axis extending along a plane, the inflatable balloon attached to and partially surrounding at least a section of the elongate body, the inflatable balloon comprising:
a first textured surface portion including a first longitudinal row of protrusions and a second longitudinal row of protrusions circumferentially adjacent to the first longitudinal row, the protrusions of the first longitudinal row and the second longitudinal row extending from an outer surface of the inflatable balloon;
a second textured surface portion including a third longitudinal row of protrusions and a fourth longitudinal row of protrusions circumferentially adjacent to the third longitudinal row, the protrusions of the third longitudinal row and the fourth longitudinal row extending from an outer surface of the inflatable balloon; and
an untextured surface portion extending circumferentially between the first textured surface portion and the second textured surface portion,
wherein, when the inflatable balloon is in an unstrained state:
a plane defining a top surface of a first protrusion of the first longitudinal row is parallel to a plane defining a top surface of a second protrusion of the second longitudinal row, and
a plane defining a top surface of a third protrusion of the third longitudinal row is parallel to a plane defining a top surface of a fourth protrusion of the fourth longitudinal row.

15. The medical device of claim 14, wherein the inflatable balloon comprises:
an untextured proximal end; and
an untextured distal end, each of the first textured surface portion, the second textured surface portion, and the untextured surface portion disposed between the untextured proximal end and the untextured distal end.

16. The medical device of claim 15, wherein, when in a collapsed state, each of the untextured proximal end and the untextured distal end extend to a radius and each of the first textured surface portion and the second textured surface portion do not extend beyond the radius.

17. The medical device of claim 14, wherein, when in a collapsed state, each of the first textured surface portion and the second textured surface portion are concave.

18. The medical device of claim 17, wherein, when in a collapsed state, each of the first textured surface portion and the second textured surface portion are concave about an axis perpendicular to a longitudinal axis of the balloon.

19. The medical device of claim 14, wherein, when the inflatable balloon is in the unstrained state, the top surface of each of the first protrusion of the first longitudinal row, the second protrusion of the second longitudinal row, the third protrusion of the third longitudinal row, and the fourth protrusion of the fourth longitudinal row are flat.

20. The medical device of claim 14, wherein, when the inflatable balloon is in the unstrained state, the top surface of each of the first protrusion of the first longitudinal row, the second protrusion of the second longitudinal row, the third protrusion of the third longitudinal row, and the fourth protrusion of the fourth longitudinal row are concave.

21. The medical device of claim 14, wherein the top surface of the first protrusion of the first longitudinal row and the top surface of the second protrusion of the second longitudinal row are parallel to the top surface of the third protrusion of the third longitudinal row and the top surface of the fourth protrusion of the fourth longitudinal row.

* * * * *